(12) United States Patent
Mumm

(10) Patent No.: US 12,110,317 B2
(45) Date of Patent: Oct. 8, 2024

(54) DUAL CYTOKINE FUSION PROTEINS COMPRISING IL-10

(71) Applicant: DEKA BIOSCIENCES, INC., Germantown, MD (US)

(72) Inventor: John Mumm, Germantown, MD (US)

(73) Assignee: DEKA BIOSCIENCES, INC., Germantown, MD (US)

( * ) Notice: Subject to any disclaimer, the term of this patent is extended or adjusted under 35 U.S.C. 154(b) by 0 days.

(21) Appl. No.: 18/501,581

(22) Filed: Nov. 3, 2023

(65) Prior Publication Data

US 2024/0076336 A1  Mar. 7, 2024

Related U.S. Application Data

(60) Division of application No. 17/684,229, filed on Mar. 1, 2022, which is a division of application No. 17/199,239, filed on Mar. 11, 2021, now Pat. No. 11,292,822, which is a continuation of application No. 17/110,104, filed on Dec. 2, 2020, now abandoned.

(60) Provisional application No. 63/054,208, filed on Jul. 20, 2020.

(51) Int. Cl.
| | |
|---|---|
| C07K 14/54 | (2006.01) |
| A61K 38/00 | (2006.01) |
| A61K 39/395 | (2006.01) |
| A61P 35/00 | (2006.01) |
| A61P 37/06 | (2006.01) |
| C07K 14/55 | (2006.01) |
| C07K 16/10 | (2006.01) |
| C07K 16/28 | (2006.01) |
| C07K 16/32 | (2006.01) |
| C07K 16/46 | (2006.01) |
| A61K 39/00 | (2006.01) |

(52) U.S. Cl.
CPC .......... *C07K 14/5428* (2013.01); *A61P 35/00* (2018.01); *A61P 37/06* (2018.01); *C07K 14/5406* (2013.01); *C07K 14/55* (2013.01); *C07K 16/10* (2013.01); *C07K 16/1045* (2013.01); *C07K 16/2803* (2013.01); *C07K 16/2863* (2013.01); *C07K 16/2896* (2013.01); *C07K 16/32* (2013.01); *C07K 16/464* (2013.01); *A61K 38/00* (2013.01); *A61K 2039/505* (2013.01); *A61K 2039/545* (2013.01); *C07K 2317/53* (2013.01); *C07K 2317/565* (2013.01); *C07K 2317/622* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,617,135 B1 | 9/2003 | Gillies et al. | |
| 9,139,634 B2 | 9/2015 | Morrison et al. | |
| 9,346,872 B2 | 5/2016 | Duerner et al. | |
| 10,858,412 B2 | 12/2020 | Mumm | |
| 10,975,133 B2 | 4/2021 | Mumm | |
| 10,975,134 B2 | 4/2021 | Mumm | |
| 10,981,965 B2 | 4/2021 | Mumm | |
| 10,981,966 B2 | 4/2021 | Mumm | |
| 11,292,822 B2 * | 4/2022 | Mumm | C07K 16/464 |
| 11,572,397 B2 * | 2/2023 | Mumm | C07K 14/5428 |
| 11,608,368 B2 * | 3/2023 | Mumm | C07K 14/5406 |
| 11,613,563 B2 * | 3/2023 | Mumm | C07K 16/32 424/85.2 |
| 11,618,775 B2 * | 4/2023 | Mumm | C07K 14/55 424/85.2 |
| 11,629,178 B2 * | 4/2023 | Mumm | A61P 37/06 424/85.2 |
| 2002/0054877 A1 | 5/2002 | Knappe et al. | |
| 2004/0072299 A1 | 4/2004 | Gillies et al. | |
| 2010/0055070 A1 | 3/2010 | Mannie | |
| 2011/0256091 A1 | 10/2011 | Neri et al. | |
| 2013/0224202 A1 | 8/2013 | Ohlfest et al. | |
| 2014/0044674 A1 | 2/2014 | Duerner et al. | |
| 2014/0170109 A1 | 6/2014 | Wulhfard | |
| 2015/0218244 A1 | 8/2015 | Emrich et al. | |
| 2015/0314014 A1 | 11/2015 | Lauermann | |
| 2016/0185853 A1 | 6/2016 | Gill et al. | |
| 2016/0200789 A1 | 7/2016 | Hemmerle | |
| 2017/0106051 A1 | 4/2017 | Oh et al. | |

(Continued)

FOREIGN PATENT DOCUMENTS

| | | |
|---|---|---|
| CN | 106349393 A | 1/2017 |
| EA | 201500208 A1 | 7/2015 |

(Continued)

OTHER PUBLICATIONS

U.S. Appl. No. 18/501,561, filed Nov. 3, 2023, Mumm; John.*

(Continued)

*Primary Examiner* — Ilia I Ouspenski

(74) *Attorney, Agent, or Firm* — ArentFox Schiff LLP

(57) ABSTRACT

The application relates to a dual cytokine fusion protein composition, pharmaceutical composition, and/or formulation thereof comprising IL-10 or IL-10 variant molecules fused to a single chain variable fragment scaffolding system and a second cytokine, where the second cytokine is linked in the hinge region of the scFv. The application also relates to methods of using the dual cytokine fusion protein composition for treating cancer, inflammatory diseases or disorders, and immune and immune mediated diseases or disorders.

4 Claims, 25 Drawing Sheets

Specification includes a Sequence Listing.

(56) References Cited

U.S. PATENT DOCUMENTS

| | | |
|---|---|---|
| 2018/0333485 A1 | 11/2018 | Weiner et al. |
| 2019/0016764 A1 | 1/2019 | Bae et al. |
| 2019/0099487 A1 | 4/2019 | Mumm et al. |
| 2019/0125840 A1 | 5/2019 | Berdel et al. |
| 2019/0352384 A1 | 11/2019 | Kaspar et al. |
| 2020/0062851 A1 | 2/2020 | Vrljic et al. |
| 2020/0283489 A1 | 9/2020 | Winston et al. |
| 2020/0306375 A1 | 10/2020 | Lobb et al. |
| 2020/0385436 A1 | 12/2020 | Mumm |
| 2020/0399337 A1 | 12/2020 | Mumm |
| 2021/0040168 A1 | 2/2021 | Mumm |
| 2021/0214782 A1 | 7/2021 | Mumm |
| 2021/0380699 A1 | 12/2021 | Campbell et al. |
| 2022/0106373 A1 | 4/2022 | Mumm |
| 2022/0380427 A1* | 12/2022 | Mumm ............... C07K 16/10 |
| 2022/0380428 A1* | 12/2022 | Mumm ............... C07K 16/32 |
| 2023/0210953 A1* | 7/2023 | Mumm ............ C07K 16/2809 424/85.2 |
| 2023/0287075 A1* | 9/2023 | Mumm ............ C07K 16/1045 |
| 2023/0340052 A1* | 10/2023 | Mumm ............... C12N 5/0636 |
| 2024/0059748 A1 | 2/2024 | Mumm |
| 2024/0059749 A1 | 2/2024 | Mumm |
| 2024/0059750 A1 | 2/2024 | Mumm |
| 2024/0067688 A1 | 2/2024 | Mumm |
| 2024/0067687 A1 | 3/2024 | Mumm |
| 2024/0076335 A1 | 3/2024 | Mumm |
| 2024/0076336 A1 | 3/2024 | Mumm |
| 2024/0076337 A1 | 3/2024 | Mumm |
| 2024/0076338 A1 | 3/2024 | Mumm |
| 2024/0076339 A1 | 3/2024 | Mumm |

FOREIGN PATENT DOCUMENTS

| | | |
|---|---|---|
| JP | 2012504425 A1 | 2/2012 |
| JP | 2014519807 A1 | 8/2014 |
| WO | 01/10912 A1 | 2/2001 |
| WO | 2012045334 A1 | 4/2012 |
| WO | 2014/023673 A1 | 2/2014 |
| WO | 2014055073 A1 | 4/2014 |
| WO | 2016082677 A1 | 6/2016 |
| WO | 2016100788 A1 | 6/2016 |
| WO | 2017091611 A1 | 6/2017 |
| WO | 2017093947 A1 | 6/2017 |
| WO | 2019/201866 A1 | 10/2019 |
| WO | 2020/181235 A1 | 9/2020 |
| WO | 2021207828 A1 | 10/2021 |
| WO | 2022019945 A1 | 1/2022 |
| WO | 2022240360 A1 | 11/2022 |

OTHER PUBLICATIONS

U.S. Appl. No. 18/501,571, filed Nov. 3, 2023, Mumm; John.*
U.S. Appl. No. 18/501,584, filed Nov. 3, 2023, Mumm; John.*
U.S. Appl. No. 18/501,741, filed Nov. 3, 2023, Mumm; John.*
U.S. Appl. No. 18/501,762, filed Nov. 3, 2023, Mumm; John.*
U.S. Appl. No. 18/501,850, filed Nov. 3, 2023, Mumm; John.*
U.S. Appl. No. 18/501,856, filed Nov. 3, 2023, Mumm; John.*
U.S. Appl. No. 18/501,884, filed Nov. 3, 2023, Mumm; John.*
U.S. Appl. No. 18/501,914, filed Nov. 3, 2023, Mumm; John.*
Beasley, Matthew D., et al., "Antibodies that potently inhibit or enchance SARS-COV-2 spike protein-ACE2 interaction isolated from synthetic single-chain antibody libaries" bioRxiv, Jul. 28, 2020.
International Search Report and Written Opinion issued by the International Search Authority corresponding to PCT/US2020/062907, dated Jun. 6, 2021.
Kalnine, N., et al., Interleukin 10, partial [synthetic construct], Genbank entry (online), National Center of Biotechnology Information, https://www.ncbi.nlm.nih.gove/protein/AAV38450.1, Jul. 26, 2016 [retrieved on May 14, 2021].
Latifi, Samir Q., et al., "Interleukin-10 Controls the Onset of Irreversible Septic Shock", Infection and Immunity, vol. 70, No. 8, p. 4441-4446, Aug. 2002.
Qin, et al., Combination of localized radiation therapy and ERB-IL-10 generates abscopal effect by activating CB8+ T cells in tumor microenvironment. Int. J. Radiation Oncol. Biol. * Phys, 99 Supplement, Oct. 1, 2017, p. S162. (Year: 2017).
Dutcher et al., "High dose interleukin-2 (Aldesleukin)-expert consensus on best management practices-2014," Journal for Immuno Therapy of Cancer, 2014, vol. 2, No. 26, pp. 1-23.
Waikar et al., "Imperfect Gold Standards for Kidney Injury Biomarker Evaluation," J Am Soc Nephrol., 2012, vol. 23, No. 1, pp. 13-21.
Steinman et al., "Optimization of current and future therapy for autoimmune diseases," Nature Medicine, Jan. 2012, vol. 18, No. 1, pp. 59-65.
Cherlin et al., "Prediction of treatment response in rheumatoid arthritis patients using genome-wide SNP data," Genetic Epidemiology, 2018, vol. 42, pp. 754-771.
Sieberts et al., "Crowdsourced assessment of common genetic contribution to predicting anti-TNF treatment response in rheumatoid arthritis," Nature Communications, vol. 7, No. 12460, pp. 1-10.
Burgess et al., "Possible Dissocation of the Heparin-binding and Mitogenic Activities of Heparin-binding (Acidic-Fivroblast) Growth Factor-1 from Its Receptor-binding Activities by Site-directed Mutagenesis of a Single Lysine Residue," The Journal of Cell Biology, Nov. 1990, vol. 111, pp. 2129-2138.
Lazar et al., "Transforming Growth Factor a: Mutation of Aspartic Acid 47 and Leucine 48 Results in Different Biological Activities," Molecular and Cellular Biology, Mar. 1988, vol. 8, No. 3, pp. 1247-1252.
Miosge et al., "Comparison of predicted and actual consequences of missense mutations," PNAS, Aug. 12, 2015, pp. E5189-E5198.
Bork, Peer, "Powers and Pitfalls in Sequence Analysis: The 70% Hurdle," Genome Research, 2000, vol. 10, pp. 398-400.
Vajdos et al., "Comprehensive Functional Maps of the Antigen-binding Site of an Anti-ErbB2 Antibody Obtained with Shotgun Scanning Mutagenesis," J. Mol. Biol., 2002, vol. 320, pp. 415-428.
Brown et al., "Tolerance to Single, but not Multiple, Amino Acid Replacements in Antibody VH CDR2," J. Immunol., 1996, vol. 156, pp. 3285-3291.
Ma, Chaoyong, "Animal Models of Disease," Modern Drug Discovery, Jun. 2004, pp. 30-36.
Blumberg et al., "Unraveling the autoimmune translational research process layer by layer," Nat Med., 2015, vol. 18, pp. 35-41.
Koss et al., "Cytokine (TNFa, LTa and IL-10) polymorphisms in inflammatory bowel diseases and normal controls: differential effects on production and allele frequencies." Genes and Immunity. Feb. 8, 2000, vol. 1, No. 3, p. 189-190.
Reich et al., "Promoter Polymorphisms of the Genes Encoding Tumor Necrosis Factor-a and Interleukin-1b are Associated with Different Subtypes of Psoriasis Characterized by Early and Late Disease Onset." The Journal of Investigative Dermatology. Jan. 1, 2002.
Franke et al., "Sequence variants in IL10, ARPC2 and multiple other loci contribute to ulcerative colitis susceptibility." Nature Genetics. Nov. 2008, vol. 40, No. 11, p. 1319-1323.
Mumm et al., "IL-10 Elicits IFNg-Dependent Tumor Immune Surveillance. Cancer Cell." Dec. 1, 2013, vol. 20, No. 6, p. 781-796.
International Search Report and Written Opinion issued in International Patent Application No. PCT/US21/12814 on Jun. 9, 2021.
Wang et al., "Targeting IL-10 Family Cytokines for the Treatment of Human Diseases," Cold Soring Harb Perspect Biol, 2019, vol. 11, a028548, pp. 1-30.
Skolnick et al., "From genes to protein structure and function: novel applications of computational approaches in the genomic era," Trends in Biotechnology, Jan. 2000, vol. 18, pp. 34-39.
Kulmanov et al., "DeepGO: predicting protein functions from sequence and interactions using a deep ontology-aware classifier," Bioinformatics, 2018, vol. 34, No. 4, pp. 660-668.
European Search Report in EP20765677.8, mailed Jul. 25, 2023, 14 pages.
Invitation to Pay Additional Fees in PCT/US2022/081460, mailed Apr. 3, 2023, 3 pages.
International Search Report and Written Opinion in PCT/US2022/081460, mailed Jul. 17, 2023, 17 pages.

(56) References Cited

OTHER PUBLICATIONS

International Search Report and Written Opinion in PCT/US2022/081862, mailed Jun. 15, 2023, 8 pages.
UniProtKB Accession No. Q8FGW4, Interleukin family protein, May 10, 2005, https://www.uniprotkb/Q8FGW4/entry, 7 pages.
International Search Report and Written Opinion in PCT/US2023/063062, mailed Jul. 31, 2023, 23 pages.
Cirulli et al., "Uncovering the roles of rare variants in common disease through whole-genome sequencing," Nature Reviews | Genetics, vol. 11, Jun. 2010, pp. 415-425.
Supplementary European Search Report mailed Jan. 8, 2024, in European Application No. 21738684.6.
Liu et al., "Treatment of B-cell Lymphoma With Chimeric IgG and Single-Chain Fv Antibody—Interleukin-2 Fusion Proteins," Blood, Sep. 15, 1998, vol. 92, No. 6, pp. 2103-2112.
Jog et al., "Epstein Barr virus Interleukin 10 Suppresses Anti-Inflammatory Phenotype in Human Monocytes," Frotiers in Immunology, vol. 9, Oct. 2018, pp. 2-12.
Salek-Ardakani et al., "Epstein-Barr Virus Encoded Interleukin-10 Inhibits HLA-Class I, ICAM-1, and B7 Expression on Human Monocytes: Implications for Immune Evasion by EBV," Virology, Dec. 20, 2002, 304(2), pp. 342-51.
Ding et al., "A Single Amino Acid Determines the Immunostimulatory Activity of Interleukin 10," J Exp Med. Jan. 17, 2000, 191(2), pp. 213-24.
Reich et al., "Response of Psoriasis to Interleukin-10 is Associated with Suppression of Cutaneous Type 1 in ammation, Downregulation of the Epidermal Interleukin-8/CXCR2 Pathway and Normalization of Keratinocyte Maturation," The Journal of Investigative Dermatology, Feb. 1, 2001, pp. 319-329.
Panjaporn et al., "A nonsense mutation in TLR5 is associated with survival and reduced IL-10 and TNF-α levels in human melioidosis," PLOS Neglected Tropical Diseases, May 5, 2017, pp. 1-14.
Chang et al., "Advances and challenges in developing cytokine fusion proteins as improved therapeutics", Expert Opinion on Drug Discovery, vol. 4, No. 2, Feb. 2, 2009, 15 pages.
Extended European Search Report and Search Opinion received for European Application No. 20946024.5, mailed on Jul. 10, 2024, 14 pages.
Hombach et al., "Targeting two co-operating cytokines efficiently shapes immune responses", OncoImmunology, vol. 2, No. 3, Mar. 1, 2013, 4 pages.
Hutmacher et al., "Antibody-cytokine fusion proteins: Biopharmaceuticals with immunomodulatory properties for cancer therapy", Advanced Drug Delivery Reviews, Amsterdam, NL, vol. 141, Sep. 7, 2018, 25 pages.
Schanzer et al., "Antitumor activity of a dual cytokine/single-chain antibody fusion protein for simultaneous delivery of GM-CSF and IL-2 to Ep-CAM expressing tumor cells", Journal of Immunotherapy, Lippincott Williams & Wilkins, Basic Study, US, vol. 29, No. 5, Sep. 1, 2006, pp. 477-488.

* cited by examiner

DUAL CYTOKINE FUSION PROTEINS COMPRISING IL-10

CROSS-REFERENCE TO RELATED APPLICATION

This application is a Divisional application of U.S. patent application Ser. No. 17/684,229 filed Mar. 1, 2022, which is a Divisional application of U.S. patent application Ser. No. 17/199,239, filed Mar. 11, 2021, now U.S. Pat. No. 11,292,822, which is a Continuation of U.S. patent application Ser. No. 17/110,104, filed on Dec. 2, 2020, now abandoned, which claims priority to U.S. Provisional Application No. 63/054,208 filed Jul. 20, 2020, the disclosure of each is incorporated by reference in its entirety.

REFERENCE TO AN ELECTRONIC SEQUENCE LISTING

The contents of the electronic sequence listing (039451-00044-Sequence-Listing-ST26.xml; Size: 138,321 bytes; and Date of Creation: Nov. 3, 2023) is herein incorporated by reference in its entirety.

FIELD OF INVENTION

The present disclosure relates to the field of biotechnology, and more specifically, to a novel dual cytokine fusion protein comprising Interleukin-10 ("IL-10") in combination with other inflammatory and immune regulating cytokines, methods of treating inflammatory and immune disease or conditions, and/or methods of treating cancer.

INTRODUCTION

IL-10, originally named cytokine synthesis inhibitory factor (Malefyt, Interleukin 10 inhibits cytokine synthesis by human monocytes: An autoregulatory role of IL-10 produced by monocytes, 1991), is a pleiotropic cytokine known to both suppress inflammatory response (Fedorak, 2000), and more recently activate CD8+ T cells to induce Interferon γ ("IFNγ") dependent anti-tumor immune responses (Mumm J., 2011). IL-10 is a non-covalent homo-dimeric cytokine with structural similarities to IFNγ. IL-10 binds to the IL-10 receptor, which consists of two subunits of the IL10 receptor 1 (IL10R1) and two subunits of the IL-10 receptor 2 (IL10R2) (Moore, 2001). The IL-10 receptor complex is expressed on the surface of most hematopoietic cells and most highly expressed on macrophages and T-cells. While IL-10 has been reported to be both an immunosuppressive (Schreiber, 2000) and an immunostimulatory cytokine (Mumm, 2011), clinical evaluation of IL-10 treatment of Crohn's patients resulted in an inverse dose response (Fedorak, 2000; Schreiber, 2000), whereas treatment of cancer patients with PEGylated IL-10 resulted in dose titratable potent anti-tumor responses (Naing, 2018). PEGylated IL-10 anti-tumor response requires endogenous CD8+ T cells and IFNγ (Mumm, 2011). Treatment of tumor bearing animals with PEGylated IL-10 results in increased intratumor CD8+ T cells and increased IFNγ on a per cell basis. Most recently, however, cancer patients treated with PEGylated IL-10 lead to evidence of immune stimulation, but no increase in anti-tumor responses (Spigel, 2020).

Interleukin-2 ("IL-2") is a four-helix bundle pleiotropic cytokine known to induce anti-tumor immune responses (Jiang, 2016), but also exhibiting high toxicity due to uncontrolled activation of and secretion of IFNγ by natural killer ("NK") cells and CD4+ T cells and expansion of T regulatory cells (Chinen, 2016). For this reason, many groups have attempted to mutate IL-2 to reduce its binding to the high affinity receptor, in an effort to reduce the toxicity of IL-2 (Chen, 2018). These muteins have not generated substantial clinical success (Bentebibe, 2019). This suggests other mechanisms must be employed to reduce the potentially lethal toxicity of IL-2.

IL-10 has been reported to suppress IL-2 driven IFNγ production secreted by both NK and CD4+ T cells (Scott, 2006), but it has also been reported to act as a cofactor for IL-2 induced CD8+ T cell proliferation (Groux, 1998). It is therefore not known whether IL-2 and IL-10 will co-activate cells of the immune system or cancel each other out.

Interleukin-4 ("IL-4") is a four-helix bundle pleiotropic cytokine considered the quintessential Th2 driving cytokine (McGuirk, 2000), that is mostly associated with driving alternative activation by macrophages (Balce, 2011). IL-4 is predominantly associated with driving inflammation associated with allergic responses and asthma (Steinke, 2001; Ryan, 1997). Furthermore, cancer patients have been treated safely with IL-4 (Davis, 2009), due to IL-4's ability to suppress some cancer cell proliferation (Lee, 2016; Gooch, 1998). While IL-4 has been reported to suppress monocyte secretion of proinflammatory cytokines (Woodward, 2012), it is not considered a potent anti-inflammatory cytokine due to its ability to prime antigen presenting cells and drive proinflammatory cytokine secretion by monocytes exposed to bacteria (Varin, 2010).

It was surprisingly discovered that Epstein-Barr virus ("EBV") IL-10 variants with one or more amino acid substitutions (at amino acid position 31, 75, or both of the mature EBV IL-10 amino acid sequence of SEQ ID No. 3) in key IL-10 receptor binding domain regions, altered the ability of EBV IL-10 to bind to and activate the IL-10 receptor. These modifications included the ability to increase the affinity of EBV IL-10 for the IL-10 receptor. The inventor discovered that EBV IL-10 variant molecules act as IL-10 receptor agonists capable of treating immune diseases, inflammatory diseases or conditions, and in treating cancer. The inventor also discovered that by incorporating monomeric EBV IL-10 variants into a scaffolding system comprising non-immunogenic variable heavy ("VH") and variable light ("VL") regions, the resulting EBV IL-10 variant molecules were half-life extended, properly folded and functionally active. The EBV IL-10 variants incorporated into the scaffolding system showed enhanced IL-10 function on both inflammatory cells (e.g., monocytes/macrophages/dendritic cells) and immune cells (e.g., CD8+ T-cells). See, U.S. Pat. No. 10,858,412; filed on Mar. 6, 2020 as U.S. application Ser. No. 16/811,718, incorporated by reference in its entirety. This application focuses on a modification to the previously described EBV IL-10 scaffolding system to deliver both IL-10 and another cytokine as part of a new fusion protein structure that additively or synergistically enhances IL-10 biology to treat inflammatory diseases, immune diseases, and/or cancer.

SUMMARY OF VARIOUS ASPECTS OF THE INVENTION

The present disclosure generally relates to a dual cytokine fusion protein.

Thus in a first aspect, the present disclosure relates to a dual cytokine fusion protein comprising IL-10 or IL-10 variants as the first cytokine that is fused to an antigen binding fragment or variable heavy ("VH") and variable light ("VL") regions of a monoclonal antibody, and a second cytokine, wherein the second cytokine is linked in between the VH and VL regions of the antigen binding fragment. In certain embodiments, the first cytokine is an IL-10, such as but not limited to human, mouse, cytomegalovirus, ("CMV"), or EBV IL-10 forms or IL-10 variant molecule, wherein the IL-10 variant has one or more amino acid substitution(s) that impact the IL-10 receptor binding domains. The fusion protein also includes a second cytokine, which is a cytokine that is different from the first cytokine, that works in tandem with the IL-10 or IL-10 variant molecule such that there is an additive or synergistic effect when the first and second cytokines are targeted to a specific antigen by the fusion protein or half-life extended by the VH and VL regions of the antigen binding fragment. The fusion protein also includes an antibody, antibody fragment, or antigen binding portion comprising a VH and VL region that directs the dual cytokine fusion protein to a target antigen recognized by the VH and VL region of the antibody, antibody fragment, or antigen binding portion thereof. In certain embodiments, the antigen binding fragment is a scFv.

In yet another aspect, the present disclosure relates to a dual cytokine fusion protein of formula (I):

$$NH_2\text{-(IL-10)-}(X^1)\text{-}(Z_n)\text{-}(X^2)\text{-(IL-10)-COOH;}$$

wherein

- "IL10" is a monomer of IL-10, wherein the IL-10 is human, mouse, CMV, or EBV IL-10, or a variant thereof, more preferably a IL10 is monomer comprising a sequence selected from SEQ ID Nos: 1, 3, 9, 10, 11, 12, 14, or 16;
- "$X^1$" is a VL or VH region obtained from a first monoclonal antibody; "$X^2$" is a VH or VL region obtained from the first monoclonal antibody; wherein when $X^1$ is a VL, $X^2$ is a VH or when $X^1$ is a VH, $X^2$ is a VL;
- "Z" is a cytokine other than IL-10; and
- "n" is an integer selected from 0-2.

In yet another aspect, the present disclosure relates to an IL-10 fusion protein of formula (II)

$$NH_2\text{-(IL10)-(L)-}(X^1)\text{-(L)-}(Z_n)\text{-(L)-}(X^2)\text{-(L)-(IL10)-COOH;}$$

wherein

- "IL-10" is a monomer sequence selected from SEQ ID Nos: 1, 3, 9, 10, 11, 12, 14, or 16;
- "L" is any linker, more preferably the linker is selected from SEQ ID No: 39, 40, or 41;
- $X^1$" is a VL or VH region obtained from a first monoclonal antibody; "$X^2$" is a VH or VL region obtained from the first monoclonal antibody; wherein when $X^1$ is a VL, $X^2$ is a VH or when $X^1$ is a VH, $X^2$ is a VL;
- "Z" is a cytokine selected from IL-6, IL-4, IL-1, IL-2, IL-3, IL-5, IL-7, IL-8, IL-9, IL-15, IL-21 IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13; and
- "n" is an integer selected from 0-2.

In other aspects, the present disclosure relates to nucleic acid molecule that encodes the dual cytokine fusion protein.

In other aspects, the present disclosure relates to methods of making and purifying the dual cytokine fusion protein. In one embodiment, the method of making the dual cytokine fusion protein includes recombinantly expressing the nucleic acid encoding the dual cytokine fusion protein.

In other aspects, the present disclosure relates to a method of treating cancer comprising administering to a subject in need thereof, an effective amount of the dual cytokine fusion protein.

In other aspects, the present disclosure relates to a method of treating inflammatory diseases or conditions comprising administering to a subject in need thereof, an effective amount of the dual cytokine fusion protein. Preferably, the inflammatory disease is Crohn's disease, psoriasis, and/or rheumatoid arthritis.

In other aspects, the present disclosure relates to a method of treating immune diseases or conditions comprising administering to a subject in need thereof, an effective amount of the dual cytokine fusion protein.

In other aspects, the present disclosure relates to method of treating, inhibiting, and/or alleviating sepsis and/or septic shock and associated symptoms thereof.

The above simplified summary of representative aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplarily pointed out in the claims.

BRIEF DESCRIPTION OF THE DRAWINGS

FIG. 1 is a schematic diagram of a IL-10 cytokine fusion protein described in U.S. Pat. No. 10,858,412.

FIG. 2 is a schematic diagram of a dual cytokine fusion protein embodied in the present disclosure, wherein the dual cytokine fusion protein comprises terminally linked IL-10 monomers (or IL-10 variants), where a second cytokine is incorporated into the linker between the VH and VL of a scFv.

FIG. 3 is a schematic diagram of a fusion protein comprising two cytokines in an alternate form (termed "SLP-IL-2") comprising DV07 (a high IL-10 receptor affinity variant of EBV IL-10) linked to a VH and VL of a scFv and an IL-2, wherein the IL-2 is fused to the carboxy terminus of the most C-terminal IL-10 monomer.

FIG. 4 is a titration study comparing SLP-IL-2 to IL-10, IL-2, and a combination of IL-10 and IL-2 on the percent reduction of TNFα secretion from monocytes/macrophages.

FIG. 5 is a titration study comparing $DK2^{10}$ to IL-10 and DegfrDV07 (SLP variant 3; SEQ ID No: 31) on the percent reduction of TNFα secretion from monocytes.

FIG. 6 is a T-cell IFNγ potentiation assay comparing SLP and $DK2^{10}$. The dark gray bar denotes serum trough therapeutic concentrations of both cytokines, and the light gray bar denotes expected therapeutic concentration requirements for $DK2^{10}$.

FIG. 7 is an assay to determine the effects of IL-10 on NK cells, $CD4^+$ T-cells, and $CD8^+$ T-cells on IL-2 mediated induction of IFNγ. The dark gray bar denotes serum trough therapeutic concentrations of both cytokines, and the light gray bar denotes expected therapeutic concentration requirements for $DK2^{10}$.

FIG. 8 is an assay measuring the effects of cytokines on model antigen presentation in T cells.

FIG. 9 is an assay measuring the induction of IFNγ in $CD4^+$ and $CD8^+$ T cells after antigen exposure.

FIG. 10 is an in vivo CT26 ($hEGFR^+$) tumor mouse model study comparing anti-tumor effects in mice treated with Degfr:DV07 or $DK2^{10}$.

FIG. 11 is an in vivo CT 26 (hEGFR$^+$) tumor mouse model study comparing the weight of mice treated with Degfr:DV07 or DK2$^{10}$.

DETAILED DESCRIPTION

Figure 1:
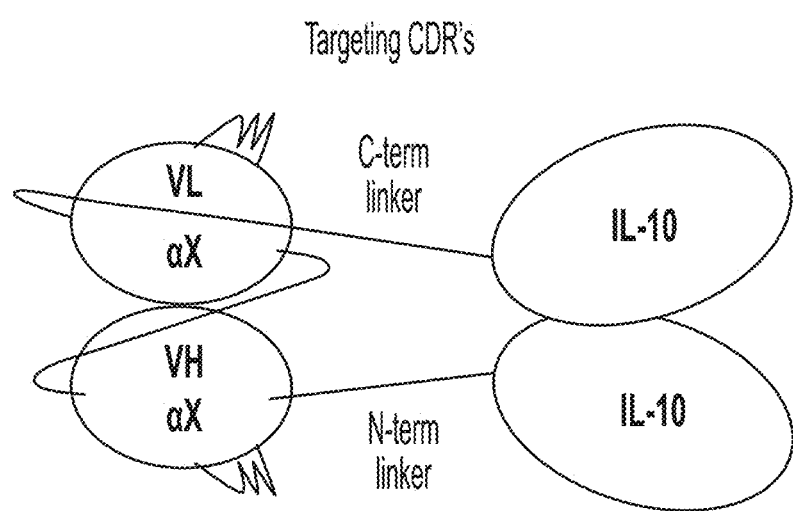

Exemplary aspects are described herein in the context of a dual cytokine fusion protein comprising IL-10, methods of making the dual cytokine fusion protein comprising IL-10, and methods of using the dual cytokine fusion protein comprising IL-10 for treating inflammatory diseases or conditions, immune diseases or conditions, treating and/or preventing cancer. Those of ordinary skill in the art will realize that the following description is illustrative only and is not intended to be in any way limiting. Other aspects will readily suggest themselves to those skilled in the art having the benefit of this disclosure. Reference will now be made in detail to implementations of the exemplary aspects as illustrated in the accompanying drawings. The same reference indicators will be used to the extent possible throughout the drawings and the following description to refer to the same or like items.

Although a number of methods and materials similar or equivalent to those described herein can be used in the practice of the various described embodiments, the preferred materials and methods are described herein.

Unless otherwise indicated, the embodiments described herein employ conventional methods and techniques of molecular biology, biochemistry, pharmacology, chemistry, and immunology, well known to a person skilled in the art. Many of the general techniques for designing and fabricating the IL-10 variants, including but not limited to human, mouse, CMV and/or EBV forms of IL-10, as well as the assays for testing the IL-10 variants, are well known methods that are readily available and detailed in the art. See, e.g., Sambrook, et al., Molecular Cloning: A Laboratory Manual (2nd Edition, 1989); Methods In Enzymology (S. Colowick and N. Kaplan eds., Academic Press, Inc.); Handbook of Experimental Immunology, Vols. I-IV (D. M. Weir and C. C. Blackwell eds., Blackwell Scientific Publications); A. L. Lehninger, Biochemistry (Worth Publishers, Inc., current addition). N-terminal aldehyde based PEGylation chemistry is also well known in the art.

DEFINITIONS

The following terms will be used to describe the various embodiments discussed herein, and are intended to be defined as indicated below.

As used herein in describing the various embodiments, the singular forms "a", "an" and "the" include plural references unless the content clearly dictates otherwise.

The term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers. In a more specific embodiment, the term "about" refers to a difference of 1-25% in terms of nucleotide sequence homology or amino acid sequence homology when compared to a wild-type sequence.

The term "interleukin-10" or "IL-10" refers to a protein comprising two subunits non-covalently joined to form a homodimer, where IL-10 is an intercalated dimer of two six helix bundle (helix A-F). As used herein, unless otherwise indicated "interleukin-10" and "IL-10" refers to any form of IL-10, including but not limited to human IL-10 ("hIL-10"; Genbank Accession No. NP_000563; or U.S. Pat. No. 6,217,857) protein (SEQ ID No: 1) or nucleic acid (SEQ ID No: 2); mouse IL-10 ("mIL-10"; Genbank Accession No: M37897; or U.S. Pat. No. 6,217,857) protein (SEQ ID No: 7) or nucleic acid (SEQ ID No: 8); or viral IL-10, ("vIL-10"). Viral IL-10 homologs may be derived from EBV or CMV (Genbank Accession Nos. NC_007605 and DQ367962, respectively). The term EBV-IL10 refers to the EBV homolog of IL-10 protein (SEQ ID No: 3) or the nucleic acid (SEQ ID No: 4). The term CMV-IL10 refers to the CMV homolog of IL-10 protein (SEQ ID No: 5) or the nucleic acid (SEQ ID No: 6). The term "monomeric" or "monomer of" IL-10, as used herein, refers to the individual subunits of IL-10 or variant IL-10 that, when non-covalently joined, form a homodimer of IL-10 or variant IL-10. The terms "wild-type," "wt" and "native" are used interchangeably herein to refer to the sequence of the protein (e.g. IL-10, CMV-IL10 or EBV IL-10) as commonly found in nature in the species of origin of the specific IL-10 in question. For example, the term "wild-type" or "native" EBV IL-10 would thus correspond to an amino acid sequence that is most commonly found in nature.

The terms "variant," "analog" and "mutein" refer to biologically active derivatives of the reference molecule, that retain a desired activity, such as, for example, anti-inflammatory activity. Generally, the terms "variant," "variants," "analog" and "mutein" as it relates to a polypeptide refers to a compound or compounds having a native polypeptide sequence and structure with one or more amino acid additions, substitutions (which may be conservative in nature), and/or deletions, relative to the native molecule. As such, the terms "IL-10 variant", "variant IL-10," "IL-10 variant molecule," and grammatical variations and plural forms thereof are all intended to be equivalent terms that refer to an IL-10 amino acid (or nucleic acid) sequence that differs from wild-type IL-10 anywhere from 1-25% in sequence identity or homology. Thus, for example, an EBV IL-10 variant molecule is one that differs from wild-type EBV IL-10 by having one or more amino acid (or nucleotide sequence encoding the amino acid) additions, substitutions and/or deletions. Thus in one form, an EBV IL-10 variant is one that differs from the wild type sequence of SEQ ID No.:3 by having about 1% to 25% difference in sequence homology, which amounts to about 1-42 amino acid difference. In one embodiment, an IL-10 variant is an EBV IL-10 comprising a V31L amino acid mutation ("DV05"; SEQ ID No: 12), a A75I amino acid mutation ("DV06"; SEQ ID No: 14), or both V31 L and A75I amino acid mutations ("DV07"; SEQ ID No: 16).

The term "fusion protein" refers to a combination or conjugation of two or more proteins or polypeptides that results in a novel arrangement of proteins that do not normally exist naturally. The fusion protein is a result of covalent linkages of the two or more proteins or polypeptides. The two or more proteins that make up the fusion protein may be arranged in any configuration from amino-terminal end ("NH$_2$") to carboxy-terminal end ("COOH"). Thus for example, the carboxy-terminal end of one protein may be covalently linked to either the carboxy terminal end or the amino terminal end of another protein. Exemplary fusion proteins may include combining a monomeric IL-10 or a monomeric variant IL-10 molecule with one or more antibody variable domains (i.e., VH and/or VL) or single chain variable region ("scFv"). The fusion proteins may also form dimers or associated with other fusion proteins of the same type, which results in a fusion protein complex. The complexing of the fusion protein may in some cases activate or increase the functionality of a fusion protein when compared to a non-complexed fusion protein. For example, a monomeric IL-10 or monomeric variant IL-10 molecule with one or more antibody variable domains may have limited or decreased capacity to bind to an IL-10 receptor; however, when the fusion protein is complexed, the monomeric forms of IL-10 or variant IL-10 molecule become a homodimer and the variable domains associate into a functional diabody.

The term "homolog," "homology," "homologous" or "substantially homologous" refers to the percent identity between at least two polynucleotide sequences or at least two polypeptide sequences. Sequences are homologous to each other when the sequences exhibit at least about 50%, preferably at least about 75%, more preferably at least about 80%-85%, preferably at least about 90%, and most preferably at least about 95%-98% sequence identity over a defined length of the molecules.

The term "sequence identity" refers to an exact nucleotide-by-nucleotide or amino acid-by-amino acid correspondence. The sequence identity may range from 100% sequence identity to 50% sequence identity. A percent sequence identity can be determined using a variety of methods including but not limited to a direct comparison of the sequence information between two molecules (the reference sequence and a sequence with unknown percent identity to the reference sequence) by aligning the sequences, counting the exact number of matches between the two aligned sequences, dividing by the length of the reference sequence, and multiplying the result by 100. Readily available computer programs can be used to aid in the identification of percent identity.

The terms "subject," "individual" or "patient" are used interchangeably herein and refer to a vertebrate, preferably a mammal. Mammals include, but are not limited to, murine, rodent, simian, human, farm animals, sport animals, and certain pets.

The term "administering" includes routes of administration which allow the active ingredient of the application to perform their intended function.

A "therapeutically effective amount" as it relates to, for example, administering the EBV IL-10 variants or fusion proteins thereof described herein, refers to a sufficient amount of the EBV IL-10 variant or fusion proteins thereof to promote certain biological activities. These might include, for example, suppression of myeloid cell function, enhanced Kupffer cell activity, and/or lack of any effect on $CD8^+$ T cells or enhanced $CD8^+$ T-cell activity as well as blockade of mast cell upregulation of Fc receptor or prevention of degranulation. Thus, an "effective amount" will ameliorate or prevent a symptom or sign of the medical condition. Effective amount also means an amount sufficient to allow or facilitate diagnosis.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The following table provides definitions for the various IL-10 fusion proteins and dual cytokine fusions proteins comprising IL-10 referenced in the present disclosure:

| Term | Definition |
|---|---|
| "Debo" | Refers to the base half-life extended IL-10 scaffolding system schematically represented by FIG. 1, wherein monomers of IL-10 (e.g., SEQ ID No. 1, 3, or 5) or IL-10 variant molecules (e.g. SEQ ID No: 9-11, 12, 14, or 16) are linked to a scFv comprising VH and VL regions obtained from a human anti-ebola antibody. Without being bound to any particular theory, the scaffolding system is capable of forming a stable complex due to VH and VL pair formation and the homodimerization of the IL-10 monomers. |
| "DeboWtEBV" or "DeboWt" | Refers to Debo schematically represented by FIG. 1, the molecule comprising monomers of wild type EBV IL-10 (SEQ ID No: 3) linked to a scFv comprising VH and VL regions obtained from a human anti-ebola antibody. |
| "DeboDV06" | Refers to Debo schematically represented by FIG. 1, the molecule comprising monomers of IL-10 variant DV06 (SEQ ID No: 14) linked to a scFv comprising VH and VL regions obtained from a human anti-ebola antibody. |
| "DeboDV07" | Refers to Debo schematically represented by FIG. 1, the molecule comprising monomers of IL-10 variant DV07 (SEQ ID No: 16) linked to a scFv comprising VH and VL regions obtained from a human anti-ebola antibody. |
| "DegfrDV07" | Refers to a Debo schematically represented by FIG. 1, the molecule comprising monomers of IL-10 variant DV07 and where the 3 CDRs in the VH and the 3 CDRs in the VL regions from the human anti-ebola scFv are replaced by 3 CDRs in the VH and 3 CDRs in the VL from an anti-EGFR antibody (Cetuximab). |
| "SLP" | Refers to an optimized variant form (variant #3) of DegfrDV07 that is SEQ ID No: 31. |
| "IL4DeboDV06" or "4DeboDV06" or "DK4$^{10}$DV06" | Refers to a dual cytokine fusion protein schematically represented by FIG. 17, where DeboDV06 includes a wild-type human IL-4 (SEQ ID No: 43) linked between the human anti-ebola derived scFv region. |
| "IL4DeboDV07" or "4DeboDV07" or "DK4$^{10}$DV07" | Refers to a dual cytokine fusion protein schematically represented by FIG. 2, where DeboDV07 includes a wild type human IL-4 (SEQ ID No: 43) linked between the human anti-ebola derived scFv region. |
| "DK2$^{10}$" or "DK2$^{10}$ form" | Refers to a class of dual cytokine fusion protein molecules schematically represented by FIG. 2, the molecule where DeboDV07 includes a human IL-2 (SEQ ID No: 36) linked between the human anti-ebola derived scFv region. DK2$^{10}$ may be made into a targeting molecule by optionally replacing the 6 CDR regions from the human anti-ebola derived scFv with 6 CDR regions (3 CDRs in the VH and 3 CDRs in the VL) from any monoclonal antibody. The nomenclature will follow the format of "DK2$^{10}$(protein target)". For example, if DK2$^{10}$ includes engraftment of 6 CDRs from a human anti-EGFR antibody (cetuximab), the molecule will be termed DK2$^{10}$egfr (SEQ ID No: 35) or if DK2$^{10}$ includes engraftment of the 6 CDRs from a human anti-HER2/Neu antibody (trastuzumab), the molecule will be termed DK2$^{10}$her2 (SEQ ID No: 52-54, or 55), respectively; or if DK2$^{10}$ includes engraftment of 6 CDRs from a human anti-VEGFR1 or anti-VEGFR2 antibody, the molecule will be termed DK2$^{10}$vegfr1 or DK2$^{10}$vegfr2, respectively; or if DK2$^{10}$ includes engraftment of 6 CDRs from a human anti-PDGFR antibody, the molecule will be termed DK2$^{10}$pdgfr. |
| "DK2$^{10}$egfr" | Refers to a DK2$^{10}$ molecule targeting EGFR, where the 6 CDR regions from the human anti-ebola derived scFv region are replaced by the 6 CDR regions (3 CDRs in the VH and 3 CDRs in the VL) from a human anti-EGFR antibody (cetuximab). The molecule is SEQ ID No: 35. The molecule may also include optimized VH (SEQ ID No: 37) and VL (SEQ ID No: 38) regions. |
| "DK2$^{10}$her2" | Refers to a DK2$^{10}$ molecule targeting HER2, where the 6 CDR regions from the human anti-ebola derived scFv region are replaced by the 6 CDR regions (3 CDRs in the VH and 3 CDRs in the VL) from a human anti-HER2 antibody (trastuzumab). The molecule is SEQ ID No: 52-54, or 55. |
| "DK2$^{10}$vegfr1" | Refers to a DK2$^{10}$ molecule targeting VEGFR1, where the 6 CDR regions from the human anti-ebola derived scFv region are replaced by the 6 CDR regions (3 CDRs in the VH and 3 CDRs in the VL) from a human anti-VEGFR1 antibody. |

Figure 2:
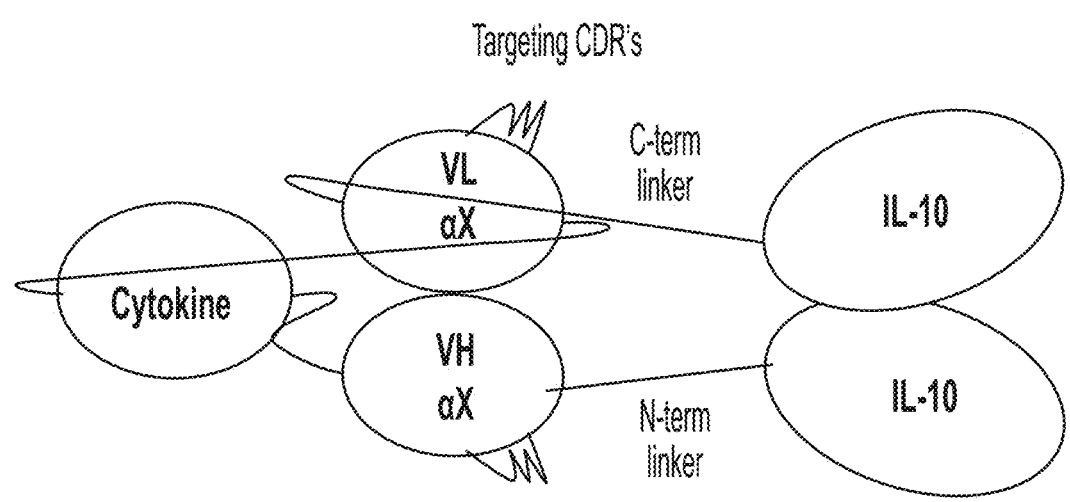
Figure 17:
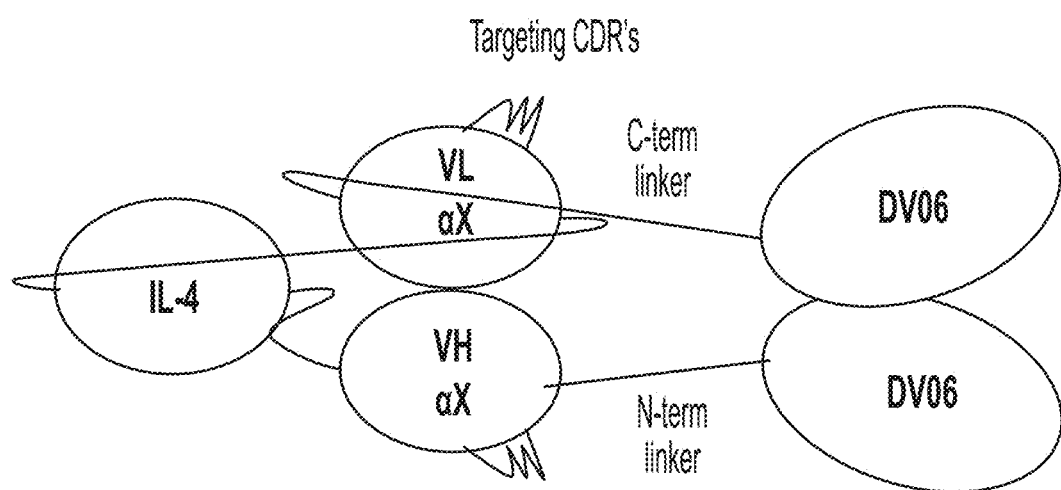
FIG. 17 is a schematic representation of the class of molecules designated as the DK4$^{10}$ form.

| Term | Definition |
| --- | --- |
| "DK2$^{10}$vegfr2" | Refers to a DK2$^{10}$ molecule targeting VEGFR2, where the 6 CDR regions from the human anti-ebola derived scFv region are replaced by the 6 CDR regions (3 CDRs in the VH and 3 CDRs in the VL) from a human anti-VEGFR2 antibody. |
| "DK4$^{10}$" or "DK4$^{10}$ form" | Refers to a class of dual cytokine fusion protein molecules schematically represented by FIG. 2 or FIG. 17, the molecule comprising either DeboDV06 or DeboDV07 in combination with an IL-4 (SEQ ID No: 43) or IL-variants (SEQ ID No: 44 or 45) where the IL-4 or IL-4 variant is linked in the hinge region of a human anti-ebola derived scFv region. DK4$^{10}$ may be made into a targeting molecule by optionally replacing the 6 CDR regions from the human anti-ebola derived scFv with 6 CDR regions (3 CDRs in the VH and 3 CDRs in the VL) from any monoclonal antibody. For example, if DK4$^{10}$ includes engraftment of 6 CDRs from a mouse anti-CD14 antibody in combination with DV06 or DV07, the molecule will be termed DK4$^{10}$mCD14DV06 (SEQ ID No: 49) or DK4$^{10}$mCD14DV07 (SEQ ID No: 50), respectively; or if DK4$^{10}$ includes engraftment of 6 CDRs from a mouse anti-MAdCAM antibody in combination with DV06, the molecule will be termed DK4$^{10}$mMAdCAMDV06 or DK4$^{10}$mMAdCAM (SEQ ID No: 51); or if DK4$^{10}$ includes engraftment of 6 CDRs from a human anti-VEGFR1 or human anti-VEGFR2 antibody, the molecule will be termed DK4$^{10}$vegfr1 or DK4$^{10}$vegfr2, respectively, where the IL-4 moiety is the non-glycosylated form of IL-4 (a N38A IL-4 variant of SEQ ID Nos: 44) and DV06. |
| "DK4$^{10}$ngDV06mCD14" or "DK4$^{10}$mCD14DV06" | Refers to a DK4$^{10}$ molecule (schematically represented by FIG. 17) targeting mouse CD14, the molecule comprising DeboDV06 with an non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a mouse anti-CD14 antibody. This molecule is SEQ ID No: 49. |
| "DK4$^{10}$ngDV07mCD14" or "DK4$^{10}$mCD14DV07" | Refers to a DK4$^{10}$ molecule (schematically represented by FIG. 1) targeting mouse CD14, the molecule comprising DeboDV07 with a non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a mouse anti-CD14 antibody. The molecule is SEQ ID No: 50. |
| "DK4$^{10}$ngDV06mMAdCAM" or "DK4$^{10}$mMAdCAMDV06" or "DK4$^{10}$mMAdCAM" | Refers to a DK4$^{10}$ molecule (schematically represented by FIG. 17) targeting mouse MAdCAM, the molecule comprising DeboDV06 with a non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a mouse anti-CD14 antibody. The molecule is SEQ ID No: 51. |
| "DK4$^{10}$ngDV06CD14" or "DK4$^{10}$CD14DV06" | Refers to a DK4$^{10}$ molecule (schematically represented by FIG. 17) targeting human CD14, the molecule comprising DeboDV06 with an non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a human anti-CD14 antibody. This molecule is SEQ ID No: 56-58, or 59. |
| "DK4$^{10}$ngDV06vegfr1" or "DK4$^{10}$vegfr1DV06" | Refers to a DK4$^{10}$ molecule (schematically represented by FIG. 17) targeting human VEGFR1, the molecule comprising DeboDV06 with an non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a human anti-VEGFR1 antibody. |

| Term | Definition |
|---|---|
| "DK4¹⁰ngDV06vegfr2" or "DK4¹⁰vegfr2DV06" | Refers to a DK4¹⁰ molecule (schematically represented by FIG. 17) targeting human VEGFR2, the molecule comprising DeboDV06 with an non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a human anti-VEGFR2 antibody. |

Dual Cytokine Fusion Protein Structure

The present disclosure provides an improvement on an embodiment of an IL-10 fusion protein previously described in U.S. Pat. No. 10,858,412 (filed as U.S. application Ser. No. 16/811,718), which is incorporated by reference in its entirety. The improvement to the IL-10 fusion protein includes incorporating a second cytokine molecule into the previously described IL-10 fusion protein. FIG. 1 is a schematic diagram representing one of the previously disclosed IL-10 fusion protein constructs described in U.S. Pat. No. 10,858,412. This IL-10 fusion protein is constructed on a VH and VL scFv scaffolding featuring two monomers of IL-10 on each end (i.e., a first IL-10 monomer on the amino terminal end and a second IL-10 monomer on the carboxy terminal end). The primary scaffolding system comprises a scFv obtained from a human anti-ebola antibody. The IL-10 fusion protein described in U.S. Pat. No. 10,858,412 includes 6 complementarity-determining regions ("CDRs") having CDRs 1-3 in the VH and CDRs 1-3 in the VL. Optionally, the VH and VL regions are capable of targeting the IL-10 fusion protein to a specific antigen. This is accomplished by substituting the 6 CDR regions of the VH and VL pair (3 CDRs in the VH and 3 CDRs in the VL) with 6 CDR regions from a VH and VL of a receptor or antigen targeting antibody, or antigen binding fragment thereof. The ability to substitute and optimize the 6 CDR and framework regions and to engraft these CDRs into the scFv scaffolding described herein, is well known and practiced by those of skill in the art. These 6 CDR regions are substitutable with 6 CDRs from any monoclonal antibody, which any person of skill would be capable of determining based on the specific target of interest.

In a first aspect, the present application relates to a dual cytokine fusion protein comprising IL-10 and at least one other cytokine, whereby the dual cytokine fusion protein has a combined or synergistic functionality when compared to the IL-10 fusion protein previously described in U.S. Pat. No. 10,858,412. FIG. 2 is a representative diagram of the improved dual cytokine fusion protein comprising IL-10. In particular, the improved dual cytokine fusion protein adapts the same or substantially same scaffolding system made up of a VH and VL scFv whereby two monomers of IL-10 terminate the dual fusion protein at the amino and carboxy terminal ends. The second cytokine is conjugated to the IL-10 fusion protein by being fused between the VH and VL regions of the scFv, which is the hinge region of the scFv. The dual cytokine fusion protein is capable of forming a functional protein complex whereby the monomers of IL-10 homodimerize into a functional IL-10 molecule and the VH and VL regions form a pair that associate together to form a scFv complex that permits antigen binding and recognition.

In certain embodiments, the dual cytokine fusion protein comprising IL-10 is a structure having formula I $$NH_2\text{-(IL10)-}(X^1)\text{—}(Z_n)\text{-}(X^2)\text{—(IL10)-COOH}$$

wherein
"IL-10" is any IL-10 monomer, such as but not limited to human, mouse, CMV or EBV IL-10, or IL-10 variant molecules;
"$X^1$" is a VL or VH region obtained from a first monoclonal antibody;
"$X^2$" is a VH or VL region obtained from the first monoclonal antibody,
wherein when $X^1$ is a VL, $X^2$ is a VH or when $X^1$ is a VH, $X^2$ is a VL;
"Z" is a second cytokine, wherein the second cytokine is a cytokine other than IL-10; and
"n" is an integer selected from 0-2.

In another embodiment, the dual cytokine fusion protein comprising IL-10 is a structure having formula II $$NH_2\text{-(IL10)-(L)-}(X^1)\text{-(L)-}(Z_n)\text{-(L)-}(X^2)\text{-(L)-(IL10)-COOH}$$

wherein
"IL-10" is an IL-10 monomer;
"L" is a linker, preferably a linker of SEQ ID NO.: 39, 40, or 41;
"$X^1$" is a VL or VH region obtained from a first monoclonal antibody;
"$X^2$" is a VH or VL region obtained from the first monoclonal antibody;
wherein when $X^1$ is a VL, $X^2$ is a VH or when $X^1$ is a VH, $X^2$ is a VL;
"Z" is a second cytokine; and
"n" is an integer selected from 0-2.

In one embodiment, the IL-10 monomer includes any form of IL-10 including human (SEQ ID NO.:1), CMV (SEQ ID NO.: 5), EBV (SEQ ID NO.:3), or mouse (SEQ ID No: 7). In another embodiment, the IL-10 monomer is a modified or variant form of EBV IL-10 (SEQ ID NO.: 3), including those that are described in U.S. Pat. No. 10,858,412. In a preferred embodiment, the EBV IL-10 comprises one or more substitutions in SEQ ID No. 3 at amino acid position 31 (herein termed "DV05"), 75 (herein termed "DV06"), or both (herein termed "DV07"). In yet another embodiment, the IL-10 monomer is a sequence of SEQ ID No: 9, 10, 11, 12, 14, or 16. The first and second monomers of IL-10 or IL-10 variant molecule are each located at the terminal ends of the fusion protein (i.e., the first monomer at the amino terminal end and the second monomer at the carboxy terminal end) as represented by FIG. 1.

In another embodiment, the VH and VL regions are from an antibody, antibody fragment, or antigen binding fragment thereof. The antigen binding fragment includes, but is not limited to, a scFv, Fab, F(ab')$_2$, V-NAR, diabody, or nanobody. Preferably the VH and VL, are from a single chain variable fragment ("scFv").

In another embodiment, the dual cytokine fusion protein comprising IL-10 includes a VH and VL pair from a single antibody. The VH and VL pair act as a scaffolding onto which monomers of IL-10 or variants thereof may be attached such that the monomers of IL-10 or variants thereof may be able to homodimerize into a functioning IL-10 molecule. A person of skill in the art will therefore appreciate that the VH and VL scaffolding used in the fusion protein may be selected based on the desired physical attributes needed for proper homodimerization of the IL-10 monomers or IL-10 monomer variants and/or the desire to maintain VH and VL targeting ability. Likewise, a person of skill will also understand that the 6 CDRs within the VH and VL pair (3 CDRs from the VH and 3 CDRs from VL) may also be substituted with 6 CDRs from other antibodies to obtain a specifically targeted fusion protein. In one embodiment, 3 CDRs from a VH and 3 CDRs from a VL (i.e., a VH and VL pair) of any monoclonal antibody may be engrafted into a scaffolding system comprising SEQ Nos: 18, 20, 21, 23, 24, or 25. It is also envisioned that if the fusion protein is not intended to target any specific antigen, a VH and VL pair may be selected as the scaffolding that does not target any particular antigen (or is an antigen in low abundance in vivo), such as the VH and VL pair from an anti-HIV and/or anti-Ebola antibody. Thus, in an embodiment, the IL-10 fusion protein of the present application may include a VH and VL pair from a human anti-ebola antibody, more preferably a sequence of SEQ ID No: 18, 21, or 25. The fusion protein may comprises a range of 1-4 variable regions. In another embodiment, the variable regions may be from the same antibody or from at least two different antibodies.

In another embodiment, the target specificity of the antibody variable chains or VH and VL pair or the 6 CDRs of the VH and VL pair may include, but not limited to those targeting proteins, cellular receptors, and/or tumor associated antigens. In another embodiment, the CDR regions from any VH and VL pair may be engrafted into the scaffolding system described above, such scaffolding preferably includes a system termed Debo (schematically represented by FIG. 1), whereby IL-10 monomers are linked to a scFv comprising VH and VL regions of a human anti-ebola antibody and the second cytokine is linked in the hinge region of the scFv (schematically represented by FIG. 2). More preferably engraftment into the Debo scaffolding system occurs in a scaffolding comprising a sequence of SEQ ID No: 18, 20, 21, 23, 24, or 25. In yet another embodiment, the variable regions or VH and VL pair or the 6 CDRs of the VH and VL pair are obtained from antibodies that target antigens associated with various diseases (e.g., cancer) or those that are not typically found or rarely found in the serum of a healthy subject, for example variable regions from antibodies directed to EGFR, PDGFR, VEGFR1, VEGFR2, Her2Neu, FGFR, GPC3, or other tumor associated antigens, MAdCam, ICAM, VCAM, CD14 or other inflammation associated cell surface proteins, HIV and/or Ebola. Thus, in one embodiment, the variable regions are obtained or derived from anti-EGFR, anti-MAdCam, anti-HIV (Chan et al, J. Virol, 2018, 92(18): e006411-19), anti-ICAM, anti-VCAM, anti-CD14, or anti-Ebola (US Published Application 2018/0180614, incorporated by reference in its entirety, especially mAbs described in Tables 2, 3, and 4) antibodies, for example. In another embodiment, the variable regions are obtained or derived from antibodies capable of enriching the concentration of cytokines, such as IL-10, to a specific target area so as to enable IL-10 to elicit its biological effect. Such an antibody might include those that target overexpressed or upregulated receptors or antigens in certain diseased regions or those that are specifically expressed in certain impacted areas. For example, the variable regions might be obtained from antibodies specific for epidermal growth factor receptor (EGFR); CD52; CD14; various immune check point targets, such as but not limited to PD-L1, PD-1, TIM3, BTLA, LAG3 or CTLA4; CD20; CD47; GD-2; VEGFR1; VEGFR2; HER2; PDGFR; EpCAM; ICAM (ICAM-1, -2, -3, -4, -5), VCAM, FAPα; 5T4; Trop2; EDB-FN; TGFβ Trap; MAdCam, β7 integrin subunit; α4β7 integrin; a4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-11; and SR-J1 to name a few. A monomer of IL-10 (e.g., human, CMV, or EBV) or variant IL-10 molecule (described herein) is conjugated to either the amino terminal end or the carboxy terminal end of a variable region (VH or VL), such that the monomer IL-10 or variant IL-10 molecule is able to dimerize with one another. In a preferred embodiment, the monomers of IL-10 (or variant IL-10) are fused to the VH and VL pair in accordance to formula I or II, wherein the IL-10 monomer is an EBV IL-10, DV05, DV06, or DV07 form of IL-10.

The dual cytokine fusion protein or dual cytokine fusion protein complex may also have an antigen targeting functionality. The dual cytokine fusion protein or dual cytokine fusion protein complex will comprise a VH and VL pair that is able to associate together to form an antigen binding site or ABS. In some configurations, the IL-10 monomers or IL-10 variant monomers thereof will be covalently linked to the end comprising the antigen binding site. The variable regions may be further modified (e.g., by addition, subtraction, or substitution) by altering one or more amino acids that reduce antigenicity in a subject. Other modifications to the variable region may include amino acids substitutions, deletions, or additions that are found outside of the 6 CDR regions of the VH and VL regions and serve to increase stability and expression of the VH and VL regions of the scFv. For example, the modifications may include modifications that are described in SEQ ID No: 27, 29, 31, or 33 wherein the CDR regions are obtained from the VH and VL regions of an anti-EGFR antibody and the regions outside of the CDRs are optimized to stabilize the scFv and/or optimized to increase expression, which may be used as a basis for linking the second cytokine between the VH and VL regions of the scFv. To demonstrate that these types of modifications are within the purview of a skilled artisan, similar modifications to the CDR regions and regions outside of the CDRs were made to a molecule in $DK2^{10}$ form comprising DV07 and targeting human HER2 (i.e., $DK2^{10}$her2), such as those described in SEQ ID No: 52-54, or 55, more preferably SEQ ID No: 54 (variant 4) or 55 (variant 5). Moreover, modifications to the CDR regions and regions outside of the CDRs were made to a molecule in $DK4^{10}$ form comprising DV06 and targeting human CD14 (i.e., $DK4^{10}$CD14DV06), such as those described in SEQ ID No: 56-58, or 59, more preferably SEQ ID No: 56 (variant 2). These and other modifications may also be made to a molecule in $DK2^{10}$ form comprising DV07 and targeting human VEGFR1 or VEGFR2; or to a molecule in $DK4^{10}$ form comprising DV06 and targeting human VEGFR1 or VEGFR2. A person of skill in the art would be capable of determining other modifications that stabilize the scFv and/or to optimize the sequence for purposes of expression.

The VH and VL pair form a scaffolding onto which CDR regions obtained for a plurality of antibodies may be grafted or engrafted. Such antibody CDR regions include those antibodies known and described above. The CDR regions in the above described VH and VL scaffolding will include the following number of amino acid positions available for CDR engraftment/insertion:

```
Heavy chain CDR1      3-7 amino acids
Heavy chain CDR2      7-11 amino acids
Heavy chain CDR3      7-11 amino acids
Light chain CDR1      9-14 amino acids
Light chain CDR2      5-9 amino acids
Light chain CDR3      7-11 amino acids
```

In a preferred embodiment, the dual cytokine fusion protein comprising IL-10 will include the previously described scaffolding IL-10 fusion protein where the VH and VL pair is derived from an anti-ebola antibody (such as those described in SEQ ID No: 19, 27, 29, 31, and 33) whereby the 6 CDR regions from the anti-ebola antibody are removed and engrafted with a VH and VL pair of a specific targeting antibody, such as but not limited to EGFR; CD52; CD14; various immune check point targets, such as but not limited to PD-L1, PD-1, TIM3, BTLA, LAG3 or CTLA4; CD20; CD47; GD-2; VEGFR1; VEGFR2; HER2; PDGFR; EpCAM; ICAM (ICAM-1, -2, -3, -4, -5), VCAM, CD14, FAPα; 5T4; Trop2; EDB-FN; TGFβ Trap; MAdCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-11; and SR-J1. In an embodiment, the 6 anti-ebola CDR regions are substituted with 6 CDR regions from anti-EGFR, anti-MAdCAM, anti-VEGFR1, anti-VEGFR2, anti-PDGFR, or anti-CD14. In a preferred embodiment, the IL-10 fusion protein is a sequence of SEQ ID No: 18, 20, 21, 23, 24, or 25 to which any of the CDRs from the above described antibodies may be engrafted. In a more preferred embodiment, the IL-10 fusion protein is a sequence of SEQ ID No: 19, 22, or 26. In a preferred embodiment, a second cytokine, such as but not limited to IL-2, IL-4, IFNα, is linked in the hinge region between the VH and VL of the scFv obtained from a human anti-ebola antibody from an IL-10 fusion protein having a sequence of SEQ ID No: 18-27, 29, 31, or 33.

In yet another embodiment, the second cytokine, is fused between the VH and VL of a scFv, as depicted in FIG. 2. The second cytokine is conjugated between the VH or VL region such that the second cytokine retains its functional properties. In one embodiment, the second cytokine is different from the IL-10 monomer. In another aspect the second cytokine is IL-10. In one embodiment, the second cytokine is IL-6, IL-4, IL-1, IL-2, IL-3, IL-5, IL-7, IL-8, IL-9, IL-15, IL-21, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13. In a preferred embodiment, the second cytokine in the dual cytokine fusion protein comprising IL-10 and IL-2 or IL-4. In a more preferred embodiment, the dual cytokine fusion protein is a sequence of SEQ ID No: 35, 46-58 or 59. In yet another embodiment, the dual cytokine fusion protein will comprise an IL-10 variant molecule selected from DV05, DV06, or DV07; the IL-10 variant molecule linked to a scaffolding system comprising the VH and VL regions from a human anti-ebola antibody (i.e., Debo), wherein with the CDRs from an antibody selected from an anti-EGFR, anti-HER2, anti-CD14, anti-VEGFR1, anti-VEGFR2, anti-MAdCAM, or anti-PDGFR are engrafted into Debo; and a second cytokine selected from IL-2, IL-4, IFNα is linked in the hinge region of the VH and VL pair. In a most preferred embodiment, the dual cytokine is a fusion protein of SEQ ID No: 35, 46-58, or 59.

In still other embodiments, the dual cytokine fusion protein comprising IL-10 incorporates linkers. A person of skill in the art knows that linkers or spacers are used to achieve proper spatial configuration of the various fusion protein parts and therefore may select the appropriate linker to use in the formation of the dual cytokine fusion protein comprising IL-10. In a more preferred embodiment, the linker or spacer may be a random amino acid sequence (such as SSGGGGS (SEQ ID No.: 39), GGGGSGGGGSGGGGS (SEQ ID No.: 40) or SSGGGGSGGGGSGGGGS (SEQ ID No. 41)) a constant region of an antibody. The constant region can be derived from, but not limited to IgG1, IgG2, IgG3, IgG4, IgA, IgM, IgD, or IgE. In one embodiment, the linker or spacer is a constant heavy ("CH") region 1, $CH_2$, or $CH_3$. In a more preferred embodiment, the linker or spacer is a random amino acid sequence of SEQ ID No: 40. In another aspect, the linker or spacer may further comprise at least two interchain disulfide bonds.

In other aspects, the present disclosure relates to nucleic acid molecules that encode for the dual cytokine fusion protein comprising IL-10 and a second cytokine. One embodiment therefore includes a nucleic acid sequence that encodes the protein set forth in SEQ ID No: 35, 46-58, or 59. In a preferred embodiment, the nucleic acid sequence includes $DK2^{10}$egfr (SEQ ID No: 60), $DK2^{10}$her2 (SEQ ID No: 62 or 63), $DK4^{10}$CD14DV06 or $DK4^{10}$ngDV06CD14 (SEQ ID No: 61), or nucleic acid sequences that share 70% to 99% sequence homology thereof. In another embodiment, the nucleic acid sequence encodes a $DK2^{10}$ form comprising DV07 and targeting human VEGFR1 or VEGFR2; or to a molecule in $DK4^{10}$ form comprising DV06 and targeting human VEGFR1 or VEGFR2. The polynucleotide sequences that encode for the dual cytokine fusion protein comprising IL-10 and a second cytokine may also include modifications that do not alter the functional properties of the described dual cytokine fusion protein. Such modifications will employ conventional recombinant DNA techniques and methods. For example, the addition or substitution of specific amino acid sequences may be introduced into an IL-10 sequence at the nucleic acid (DNA) level using site-directed mutagenesis methods employing synthetic oligonucleotides, which methods are also well known in the art. In a preferred embodiment, the nucleic acid molecules encoding the dual cytokine fusion protein comprising IL-10 and a second cytokine may include insertions, deletions, or substitutions (e.g., degenerate code) that do not alter the functionality of the IL-10 variant molecule. The nucleotide sequences encoding the IL-10 variant and fusion proteins described herein may differ from the amino acid sequences due to the degeneracy of the genetic code and may be 70-99%, preferably 70%, 75%, 80%, 85%, 90%, 95%, 96%, 97%, 98%, or 99%, homologous to the aforementioned sequences. Accordingly, an embodiment of the present disclosure includes a nucleic acid sequence that encodes a protein of SEQ ID Nos: 35, 46-58, or 59 but differing by 70-99% due to the degeneracy of the genetic code.

The nucleotide sequences encoding the dual cytokine fusion proteins described herein may further comprise well known sequences that aid in, for example, the expression, production, or secretion of the proteins. Such sequences may include, for example a leader sequence, signal peptide, and/or translation initiation sites/sequence (e.g. Kozak consensus sequence). The nucleotide sequences described herein may also include one of more restriction enzyme sites that allow for insertion into various expression systems/ vectors.

In another embodiment, the nucleotide sequences encoding the dual cytokine fusion protein may be used directly in gene therapy. In one embodiment, the variant IL-10 molecules or fusion protein of the present application can be delivered by any method know in the art, including direct administration of the mutant IL-10 protein and gene therapy with a vector encoding the mutant IL-10 protein. Gene therapy may be accomplished using plasmid DNA or a viral vector, such as an adeno-associated virus vector, an adenovirus vector, a retroviral vector, etc. In some embodiments, the viral vectors of the application are administered as virus particles, and in others they are administered as plasmids (e.g. as "naked" DNA).

Other methods for the delivery of the nucleotide sequences include those which are already known in the art. These would include the delivery of the nucleotide sequences, such as but not limited to DNA, RNA, siRNA, mRNA, oligonucleotides, or variants thereof, encoding the IL-10 or IL-10 variant molecules by a cell penetrating peptide, a hydrophobic moiety, an electrostatic complex, a liposome, a ligand, a liposomal nanoparticle, a lipoprotein (preferably HDL or LDL), a folate targeted liposome, an antibody (such as Folate receptor, transferrin receptor), a targeting peptide, or by an aptamer. The nucleotide sequences encoding IL-10 variant molecules may be delivered to a subject by direct injection, infusion, patches, bandages, mist or aerosol, or by thin film delivery. The nucleotide (or the protein) may be directed to any region that is desired for targeted delivery of a cytokine stimulus. These would include, for example, the lung, the GI tract, the skin, liver, brain though intracranial injection, deep seated metastatic tumor lesions via ultrasound guided injections.

In another aspect, the present disclosure relates to methods of preparing and purifying the dual cytokine fusion protein comprising IL-10. For example, nucleic acid sequences that encode the dual cytokine fusion protein described herein may be used to recombinantly produce the fusion proteins. For example, using conventional molecular biology and protein expression techniques, the dual cytokine fusion protein described herein may be expressed and purified from mammalian cell systems. These systems include well known eukaryotic cell expression vector systems and host cells. A variety of suitable expression vectors may be used and are well known to a person skilled in the art, which can be used for expression and introduction of the variant IL-10 molecules and fusion proteins. These vectors include, for example, pUC-type vectors, pBR-type vectors, pBI-type vectors, pGA-type, pBinI9, pBI121, pGreen series, pCAMBRIA series, pPZP series, pPCV001, pGA482, pCLD04541, pBIBAC series, pYLTAC series, pSB11, pSB1, pGPTV series, and viral vectors and the like can be used. Well known host cell systems include but not limited to expression in CHO cells.

The expression vectors harboring the dual cytokine fusion protein may also include other vector componentry required for vector functionality. For example, the vector may include signal sequences, tag sequences, protease identification sequences, selection markers and other sequences regulatory sequences, such as promoters, required for proper replication and expression of the dual cytokine fusion protein. The particular promoters utilized in the vector are not particularly limited as long as they can drive the expression of the dual cytokine fusion protein in a variety of host cell types. Likewise, the type of Tag promoters are not be limited as long as the Tag sequence makes for simplier or easier purification of expressed variant IL-10 molecule easier. These might include, for example, 6-histidine, GST, MBP, HAT, HN, S, TF, Trx, Nus, biotin, FLAG, myc, RCFP, GFP and the like can be used. Protease recognition sequences are not particularly limited, for instance, recognition sequences such as Factor Xa, Thrombin, HRV, 3C protease can be used. Selected markers are not particularly limited as long as these can detect transformed rice plant cells, for example, neomycin-resistant genes, kanamycin-resistant genes, hygromycin-resistant genes and the like can be used.

The dual cytokine fusion protein described above may also include additional amino acid sequences that aid in the recovery or purification of the fusion proteins during the manufacturing process. These may include various sequence modifications or affinity tags, such as but not limited to protein A, albumin-binding protein, alkaline phosphatase, FLAG epitope, galactose-binding protein, histidine tags, and any other tags that are well known in the art. See, e.g., Kimple et al (Curr. Protoc. Protein Sci., 2013, 73:Unit 9.9, Table 9.91, incorporated by reference in its entirety). In one aspect, the affinity tag is an histidine tag having an amino acid sequence of HHHHHH (SEQ ID No.: 42). The histidine tag may be removed or left intact from the final product. In another embodiment, the affinity tag is a protein A modification that is incorporated into the fusion protein (e.g., into the VH region of the fusion proteins described herein). A person of skill in the art will understand that any dual cytokine fusion protein sequence described herein can be modified to incorporate a protein A modification by inserting amino acid point substitutions within the antibody framework regions as described in the art.

In another aspect, the protein and nucleic acid molecules encoding dual cytokine fusion protein may be formulated as a pharmaceutical composition comprising a therapeutically effective amount of the dual cytokine fusion protein and a pharmaceutical carrier and/or pharmaceutically acceptable excipients. The pharmaceutical composition may be formulated with commonly used buffers, excipients, preservatives, stabilizers. The pharmaceutical compositions comprising the dual cytokine fusion protein is mixed with a pharmaceutically acceptable carrier or excipient. Various pharmaceutical carriers are known in the art and may be used in the pharmaceutical composition. For example, the carrier can be any compatible, non-toxic substance suitable for delivering the dual cytokine fusion protein compositions of the application to a patient. Examples of suitable carriers include normal saline, Ringer's solution, dextrose solution, and Hank's solution. Carriers may also include any poloxamers generally known to those of skill in the art, including, but not limited to, those having molecular weights of 2900 (L64), 3400 (P65), 4200 (P84), 4600 (P85), 11,400 (F88), 4950 (P103), 5900 (P104), 6500 (P105), 14,600 (F108), 5750 (P123), and 12,600 (F127). Carriers may also include emulsifiers, including, but not limited to, polysorbate 20, polysorbate 40, polysorbate 60, and polysorbate 80, to name a few. Non-aqueous carriers such as fixed oils and ethyl oleate may also be used. The carrier may also include additives such as substances that enhance isotonicity and chemical stability, e.g., buffers and preservatives, see, e.g., Remington's Pharmaceutical Sciences and U.S. Pharmacopeia: National Formulary, Mack Publishing Company, Easton, Pa. (1984). Formulations of therapeutic and diagnostic agents may be prepared by mixing with physiologically acceptable carriers, excipients, or stabilizers in the form of lyophilized powders, slurries, aqueous solutions or suspensions, for example.

The pharmaceutical composition will be formulated for administration to a patient in a therapeutically effective amount sufficient to provide the desired therapeutic result. Preferably, such amount has minimal negative side effects. In one embodiment, the amount of dual cytokine fusion protein administered will be sufficient to treat or prevent inflammatory diseases or condition. In another embodiment, the amount of dual cytokine fusion protein administered will be sufficient to treat or prevent immune diseases or disorders. Instill another embodiment, the amount of dual cytokine fusion protein administered will be sufficient to treat or prevent cancer. The amount administered may vary from patient to patient and will need to be determined by considering the subject's or patient's disease or condition, the overall health of the patient, method of administration, the severity of side-effects, and the like.

An effective amount for a particular patient may vary depending on factors such as the condition being treated, the overall health of the patient, the method route and dose of administration and the severity of side effects. The appropriate dose administered to a patient is typically determined by a clinician using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

The method for determining the dosing of the presently described dual cytokine fusion protein will be substantially similar to that described in U.S. Pat. No. 10,858,412. Generally, the presently described dual cytokine fusion protein will have a dosing in the range of 0.5 microgram/kilogram to 100 micrograms/kilogram. The dual cytokine fusion protein may be administered daily, three times a week, twice a week, weekly, bimonthly, or monthly. An effective amount of therapeutic will impact the level of inflammation or disease or condition by relieving the symptom. For example, the impact might include a level of impact that is at least 10%; at least 20%; at least about 30%; at least 40%; at least 50%; or more such that the disease or condition is alleviated or fully treated.

Compositions of the application can be administered orally or injected into the body. Formulations for oral use can also include compounds to further protect the variant IL-10 molecules from proteases in the gastrointestinal tract. Injections are usually intramuscular, subcutaneous, intradermal or intravenous. Alternatively, intra-articular injection or other routes could be used in appropriate circumstances. Parenterally administered dual cytokine fusion protein are preferably formulated in a unit dosage injectable form (solution, suspension, emulsion) in association with a pharmaceutical carrier and/or pharmaceutically acceptable excipients. In other embodiments, compositions of the application may be introduced into a patient's body by implantable or injectable drug delivery system.

Testing the Dual Cytokine Fusion Protein

A plurality of screening assays are known and available to those of skill in the art to test for the desired biological function. In one embodiment, the desired biological function includes, but are not limited to, reduced anti-inflammatory response, reduce T-cell stimulation, enhanced T-cell function, enhanced Kupffer cell functionality and reduced mast cell degranulation.

For example, it is known that IL-10 exposure primes T cells to generate and secrete more IFNγ upon T cell receptor stimulation. Simultaneously, IL-10 exposure prevents the secretion of TNFα, IL-6 and other pro-inflammatory cytokines secreted from monocytes/macrophages in response to LPS. IL-10 also suppresses FoxP3$^+$CD4$^+$ T$_{reg}$ proliferation. In one embodiment, the dual cytokine fusion protein that maximize monocyte/macrophage suppression but lack T cell effects, including both stimulatory and suppressive responses, will be positively selected. In one embodiment, screening for dual cytokine fusion proteins that possess increased anti-inflammatory effects will be positively selected for the treatment of autoimmune, anti-inflammatory disease or both. In another embodiments, dual cytokine fusion proteins that enhance Kupffer cell scavenging and lack T$_{reg}$ suppression will also be selected to develop for treatment of Non-alcoholic Steatotic Hepatitis (NASH) and/or Non-alcoholic Fatty Liver Disease (NAFLD). In yet another embodiment, dual cytokine fusion proteins that maximize T cell biology, including both stimulatory and suppressive responses, and also possesses enhanced Kupffer cell scavenging, will be selected to develop for the treatment of cancer. Various assays and methods of screening the dual cytokine fusion proteins are previously described in co-pending U.S. Pat. No. 10,858,412, which is incorporated by reference in its entirety. See, U.S. application Ser. No. 16/811,718 Specification at pages 39-42.

Methods of Treating and/or Preventing Using the Dual Cytokine

In other aspects, the present disclosure relates to methods of treating and/or preventing malignant diseases or conditions or cancer comprising administering to a subject in need thereof a therapeutically effective amount of the dual cytokine fusion protein comprising IL-10 and a second cytokine. Such a protein will be in DK2$^{10}$ form, where the fusion protein will comprise monomers of DV07 linked to a VH and VL scaffolding system obtained from a human anti-ebola antibody which is engrafted with CDRs from any antibody targeting a tumor associated antigen ("TAA"); with a second cytokine, IL-2, linked between the hinge region of the VH and VL. In a preferred embodiment, the dual cytokine fusion protein comprises EBV IL-10 monomers of DV07. In a more preferred embodiment, the EBV IL-10 monomers include both substitutions at amino acid positions 31 (V31 L) and 75 (A75I) of EBV IL-10 of SEQ ID NO: 3. In a more preferred embodiment, the EBV IL-10 is SEQ ID Nos: 11 or 16. In a preferred embodiment, the dual cytokine fusion protein comprises a VH and VL pair from an anti-ebola antibody, wherein the CDRs are substituted with 6 CDRs from any TAA targeting antibody. In a preferred embodiment, the VH and VL regions of the dual cytokine fusion protein includes a VH of SEQ ID No: 37 and a VL of SEQ ID No: 38. In a more preferred embodiment, the dual cytokine fusion protein comprises a VH and VL pair from an anti-ebola antibody, wherein the CDRs are substituted with 6 CDRs from: an anti-EGFR antibody (SEQ ID Nos: 27, 29, 31, or 33), wherein the second cytokine is linked between the VH and VL regions of the scFv. In other embodiments, the 6 CDR regions are substituted with 6 CDRs from an anti-Her2 Neu; an anti-PDGFR; anti-VEGFR1 and anti-VEGFR2, an anti-FGFR; an anti-HER3; or an anti-GPC3. Preferably the 6 CDRs are obtained from anti-EGFR, or anti-HER2. In another preferred embodiment, the second cytokine is an IL-2. In a most preferred embodiment, a dual cytokine fusion protein of SEQ ID Nos: 35 (EGFR targeting) or 52-55 (HER2 targeting) is used to treat cancer.

In still other aspects, the present disclosure relates to methods of treating and/or preventing inflammatory diseases or conditions comprising administering to a subject in need thereof a therapeutically effective amount of the dual cytokine fusion protein comprising IL-10 (or variants thereof such as DV06) and a second cytokine (such as IL-4). In a preferred embodiment, the inflammatory diseases or disorders include, but are not limited to Crohn's disease, psoriasis, and rheumatoid arthritis ("RA"). Such a protein will be in DK4$^{10}$ form, where the fusion protein will comprise monomers of DV06 linked to a VH and VL scaffolding system obtained from a human anti-ebola antibody which is engrafted with CDRs from any antibody targeting various inflammatory/immune receptors or proteins (such as anti-CD14, anti-VEGFR2, anti-MAdCAM); with a second cytokine, IL-4 (SEQ ID No: 43) or a non-glycosylated form of IL-4 (SEQ ID No: 44), linked between the hinge region of the VH and VL. In an embodiment, the IL-10 monomer includes wild type EBV IL-10, an EBV IL-10 variant with a single amino acid substitution at position 75 of EBV IL-10 (DV06), or an EBV IL-10 variant with two amino acid substitutions at positions 31 and 75 of EBV IL-10 (DV07). In a preferred embodiment, the EBV IL-10 monomers is wild type EBV IL-10 or DV06. In a more preferred embodiment, the EBV IL-10 is SEQ ID Nos: 3, 9, 10, 11, 14 or 16. In a preferred embodiment, the dual cytokine fusion protein comprises a scaffolding system with a VH and VL pair from a human anti-ebola antibody. In a more preferred embodiment, the dual cytokine fusion protein used for treating inflammatory diseases or conditions comprises a VH and VL pair from a human anti-ebola antibody, wherein the CDRs are substituted with 6 CDRs from VH and VL of an anti-MAdCAM antibody (preferably a human anti-MAdCAM antibody) or an anti-CD14 antibody (preferably a human anti-CD14 antibody) or anti-VEGFR2 (preferably a human anti-VEGFR2 antibody). In another preferred embodiment, the second cytokine is an IL-4, preferably an IL-4 variant having a N38A substitution (SEQ ID No. 44). In a most preferred embodiment, the inflammatory disease includes sepsis and/or septic shock, which is treated with a dual cytokine fusion protein comprising DV06 or DV07 monomers and IL-4, wherein CDRs from an anti-CD14 antibody are engrafted into an anti-ebola VH and VL scFv scaffolding system. In a preferred embodiment, the dual cytokine fusion protein is in $DK4^{10}$ form of SEQ ID No: 56-58, or 59, more preferably SEQ ID No: 56. In another preferred embodiment, the inflammatory disease includes IBD, which is treated with a dual cytokine fusion protein comprising DV06 monomers and IL-4 wherein the CDRs from an anti-MAdCAM antibody are engrafted into an anti-ebola VH and VLscFv scaffolding system. In yet another preferred embodiment, the inflammatory disease includes psoriasis or RA, which is treated with a dual cytokine fusion protein comprising DV06 monomers and IL-4 wherein the CDRs from an anti-VEGFR2 antibody are engrafted into a human anti-ebola VH and VL scFv scaffolding system. In a most preferred embodiment, a dual cytokine fusion protein of SEQ ID No: 46-50, 56-58, or 59 (CD14 targeting) or 51 (MAdCAM targeting) is used to reduce inflammation or sepsis.

In yet another aspect, the present disclosure relates to methods of treating and/or preventing immune diseases or conditions comprising administering to a subject in need thereof a therapeutically effective amount of the dual cytokine fusion protein comprising IL-10.

In other embodiments, the present disclosure also contemplates methods of co-administration or treatment with a second therapeutic agent, e.g., a cytokine, steroid, chemotherapeutic agent, antibiotic, anti-inflammatory agents, or radiation, are well known in the art. These might include combination treatments with other therapeutic agents, such as but not limited to one or more the following: chemotherapeutics, interferon-β, for example, IFNβ-1α and IFN-β-1β; a protein that simulates myelin basic protein; corticosteroids; IL-1 inhibitors; TNF inhibitors; anti-TNFα antibodies, anti-IL-6 antibodies, IL-1 br-Ig fusion, anti-IL-23 antibodies, antibodies to CD40 ligand and CD80; antagonists of IL-12 and IL-23, e.g., antagonists of a p40 subunit of IL-12 and IL-23 (e.g., inhibitory antibodies against the p40 subunit); IL-22 antagonists; small molecule inhibitors, e.g., methotrexate, leflunomide, sirolimus (rapamycin) and analogs thereof, e.g., CCI-779; Cox-2 and cPLA2 inhibitors; NSAIDs; p38 inhibitors; TPL-2; Mk-2; NFkβ inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkβ antagonists.

Additionally, the combination treatment useful for administration with the dual cytokine fusion protein may include TNF inhibitors include, e.g., chimeric, humanized, effectively human, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, ENBREL™), p55 kD TNF receptor-IgG fusion protein; and TNF enzyme antagonists, e.g., TNFα converting enzyme (TACE) inhibitors. Other combination treatment with anti-inflammatory agents/drugs that includes, but not limited to standard non-steroidal anti-inflammatory drugs (NSAIDs) and cyclo-oxygenase-2 inhibitors. NSAID may include aspirin, celecoxib, diclofenac, diflunisal, etodolac, ibuprofen, indomethacin, ketoprofen, ketorolac, nabumetone, naproxen, oxaprozin, piroxicam, salsalate, sulindac, and/or tolmetin. The cyclo-oxygenase-2 inhibitor employed in compositions according to the application could, for example, be celecoxib or rofecoxib.

Additional therapeutic agents that can be co-administered and/or co-formulated with the dual cytokine fusion protein include one or more of: interferon-β, for example, IFN β-1α and IFN β-1β; COPAXONE®; corticosteroids; IL-1 inhibitors; TNF antagonists (e.g., a soluble fragment of a TNF receptor, e.g., p55 or p75 human TNF receptor or derivatives thereof, e.g., 75 kdTNFR-IgG; antibodies to CD40 ligand and CD80; and antagonists of IL-12 and/or IL-23, e.g., antagonists of a p40 subunit of IL-12 and IL-23 (e.g., inhibitory antibodies that bind to the p40 subunit of IL-12 and IL-23); methotrexate, leflunomide, and a sirolimus (rapamycin) or an analog thereof, e.g., CCI-779. Other therapeutic agents may include Imfimzi or Atezolizumb.

For purposes of treating NASH, for example, the dual cytokine fusion protein may be combined with cholesterol lowering agents, such as statins and non-statin drugs. These agents include, but are not limited to simvastatin, atorvastatin, rosuvastatin, lovastatin, pravastatin, gemfibrozil, fluvastatin, cholestyramine, fenofibrate, cholesterol absorption inhibitors, bile acid-binding resins or sequestrants, and/or microsomal triglyceride transfer protein (MTP) inhibitors.

Representative chemotherapeutic agents that may be co-administered with the dual cytokine fusion protein described herein may include for following non-exhaustive list: include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g. paclitaxel (TAXOL® Bristol-Myers Squibb Oncology, Princeton, N.J.) and doxetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda® Roche, Switzerland; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

EXAMPLES

Example 1: IL-10 and IL-2 Dual Cytokine Fusion Protein In Vitro Study

To evaluate the in vitro effects of targeting two cytokines to a tumor, a dual cytokine fusion protein, termed DK2$^{10}$ (SEQ ID No: 35) (see FIG. 2 as a representative diagram of the structure), was constructed from the following components:

(a) two monomers of DV07 (which is a high affinity IL-10 receptor binding, EBV IL-10 variant) coupled to a scFv with a VH and VL pair targeting EGFR (the IL-10 fusion protein termed "SLP" of SEQ ID No. 31); and (b) an IL-2 cytokine (SEQ ID No: 36);

where the IL-2 cytokine is conjugated or linked in the hinge (or linker) region between the VH (SEQ ID No: 37) and VL (SEQ ID No: 38) of the scFv targeting EGFR (the SLP variant of SEQ ID No: 31).

This dual cytokine fusion protein was generated to evaluate the combined effects of these two cytokines on IL-2 induction of IFNγ from NK, CD4$^+$ and CD8$^+$ T cells. A comparative construct was also designed where the IL-2 was linked to the C-terminus of most C-terminal DV07 monomer of the SLP construct described above, creating a construct term "SLP-IL-2" (FIG. 3).

To test the effects of SLP-IL-2 (FIG. 3) and DK2$^{10}$ (SEQ ID No: 35, schematically represented in FIG. 2) on the immune system, peripheral blood monocytes were isolated by magnetic bead positive selection to evaluate the DV07 function, and then NK, CD4$^+$ and CD8$^+$ T cells were similarly isolated for in vitro testing. A series of cellular in vitro assays were set up to model immunological function at different time points in the exposure cycle of a molecule injected subcutaneously in the human body.

Figure 3:
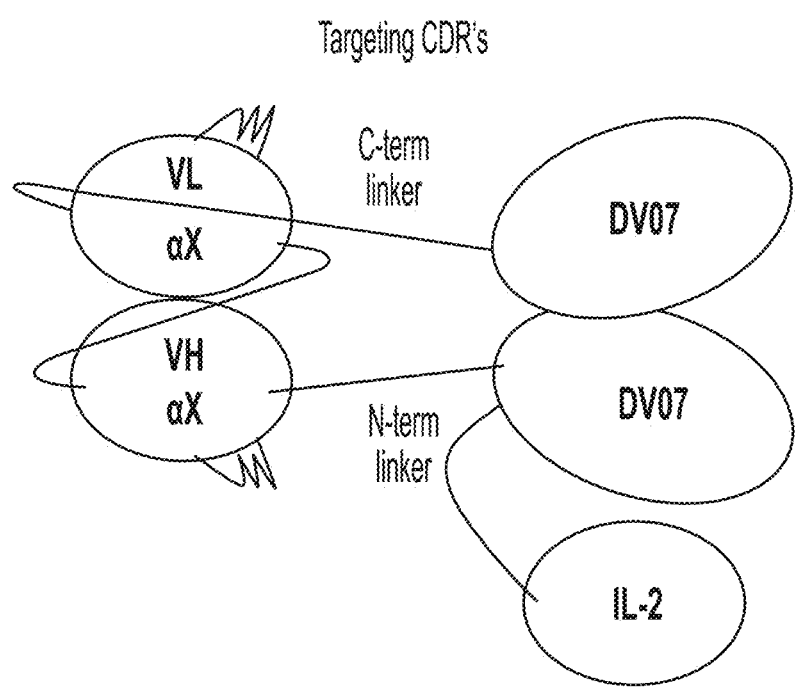
Figure 4:
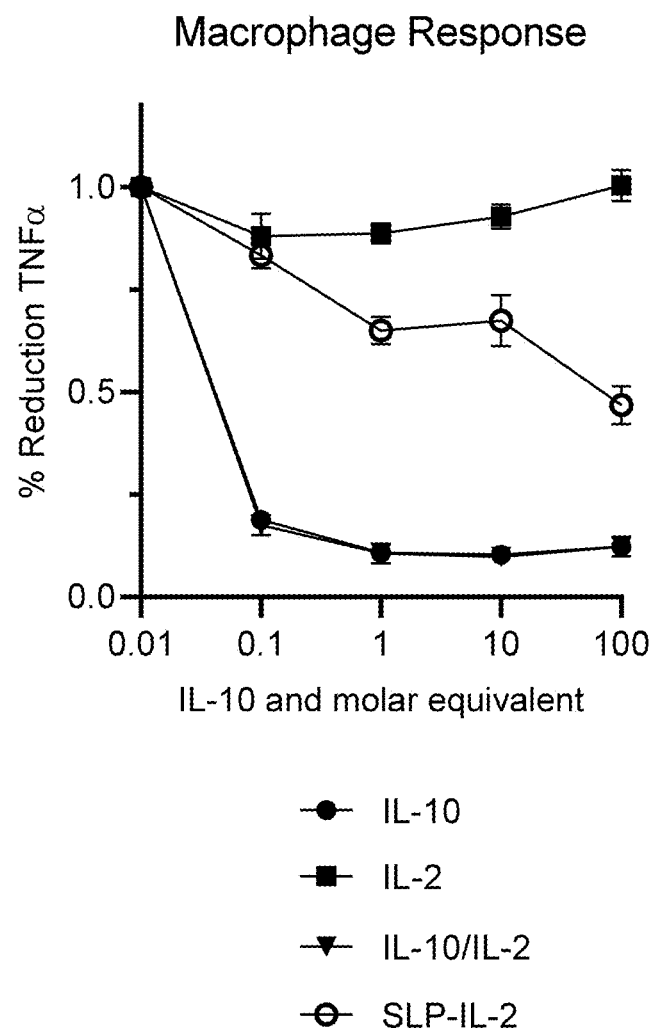

First, the effects of IL-10, IL-2, the combination of IL-10 and IL-2, and SLP-IL-2 were tested on monocytes/macrophages. This test shows that IL-2 alone does not suppress TNFα, a proinflammatory cytokine, secretion in response to LPS, whereas the SLP:IL-2 construct, which comprises DV07 was able to suppress proinflammatory cytokine secretion. A titration of IL-10, IL-2, the combination of IL-10 and IL-2, and SLP-IL-2 was performed (FIG. 4). Unexpectedly, these data also suggest that the function of a DV07 containing construct is compromised by the addition of the IL-2 cytokine to the C-terminus of the IL-10 monomer (i.e., SLP-IL-2; FIG. 3).

Figure 5:
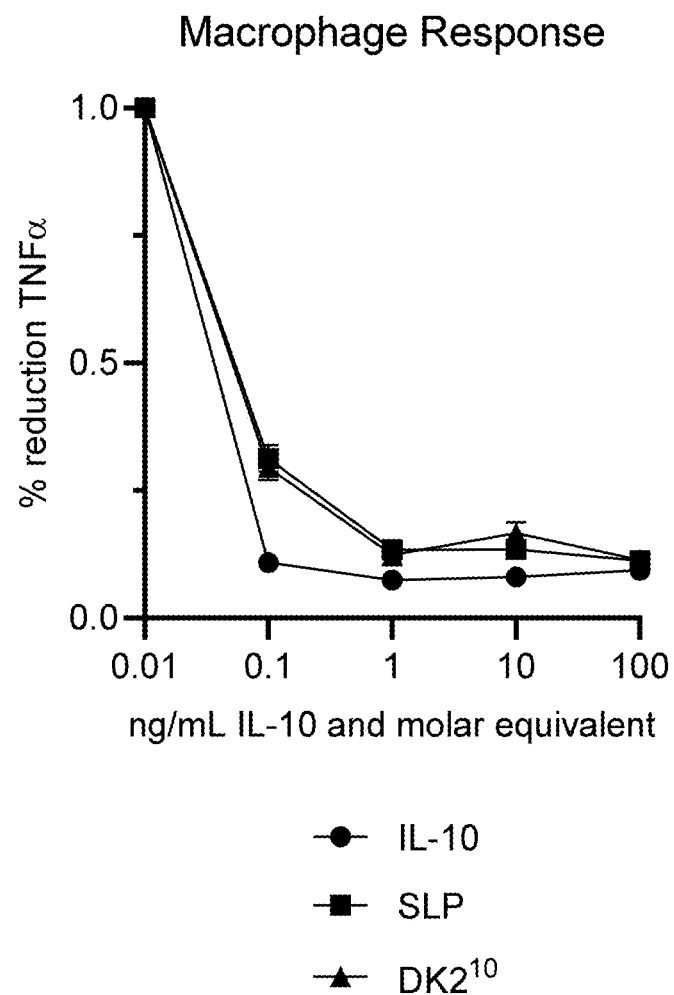

The effects of DK2$^{10}$, which was designed as a DV07 containing variant with IL-2 incorporated into the linker between the VH and VL of the scFv obtained from a human anti-ebola antibody, (schematically represented in FIG. 2), was also evaluated on monocytes/macrophages to determine whether the construct retains IL-10 function. A titration of IL-10, SLP (an optimized variant of DegfrDV07 of SEQ ID No: 31), and DK2$^{10}$egfr (SED ID No: 35) was performed (FIG. 5) and the data suggests that unlike linking IL-2 to the C-terminus of the most C-terminal IL-10 monomer (SLP-IL-2), the unexpected incorporation of IL-2 into the linker between the VH and VL of the scFv does not compromise the function of SLP (the DV07 containing IL-10 fusion protein of SEQ ID No: 31).

In order to assess the direct effects of DK2$^{10}$egfr on T cells, an assay that has been reported to directly elucidate the primary function of IL-10 on CD8$^+$ T cells, predominantly the potentiation of IFNγ that is only released upon T cell receptor engagement (Chan, 2015; Mumm J., 2011; Emmerich, 2012) was performed.

The necessary therapeutic concentration of PEG-rHuIL-10 was found to be 2-5 ng/mL, (Mumm J., 2011; Naing A., 2018; Naing A., 2016) in systemic circulation. The CD8$^+$ T cell IFNγ assay exhibits maximal T cell IFNγ potentiation at 1-10 ng/mL, suggesting this is an appropriate model assay system for evaluating the specific potency of IL-10 for cancer applications.

Figure 6:
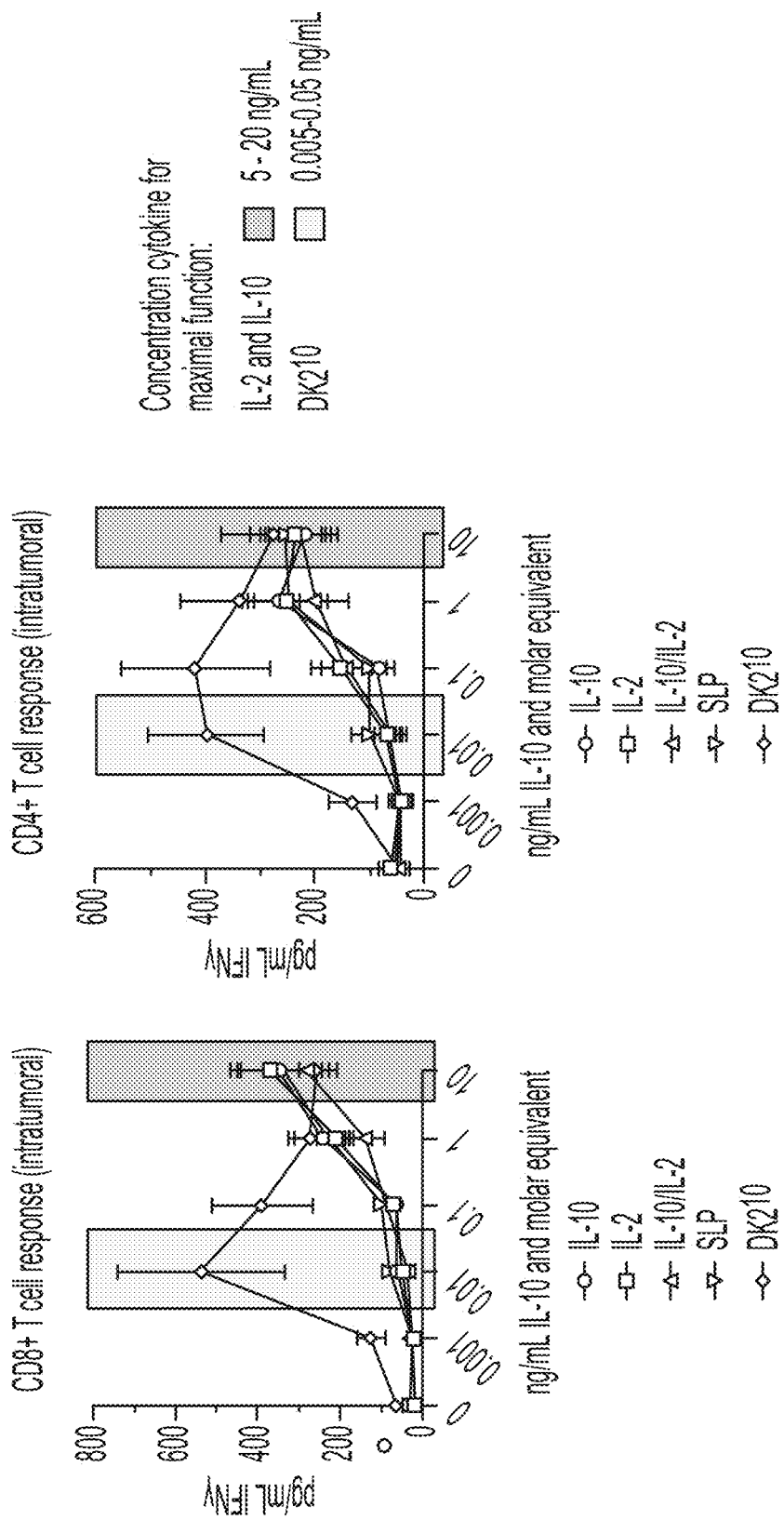

High dose IL-2 therapy is the administration of between 600,000 to 720,000 U/kg IL-2 every 8 hours for 5 days (Buchbinder, 2019) which is the equivalent of 37-45 ug/kg, (1.1 mgs=18×106 IUs for IL-2). The $C_{max}$ concentration in systemic circulation for high dose IL-2 is between 37 to 45 ng/mL (Kirchner, 1998), where trough exposure is about 10 ng/ml. These data suggest that the use of this assay is also appropriate for evaluating T cell response to IL-2 as maximal IL-2 stimulation of antigen specific T cell function is approximately 10 ng/ml in vitro. We therefore assessed the response of CD8$^+$ and CD4$^+$ T-cells to IL-10, IL-2, the combination of IL-10 and IL-2, SLP and DK2$^{10}$ in this assay format (FIG. 6). Unexpectedly, the tethering of IL-2 and DV07 together (i.e., tethering IL-2 to SLP in the into the linker between the VH and VL of the scFv) increased the potency of either molecule alone by 100-fold (from ~1-10 ng/mL to 0.01 ng/mL). Unexpectedly, the addition of untethered IL-2 and IL-10 at these concentrations did not enhance IFNγ secretion, which suggests that the effect of tethering IL-2 and DV07 together leads to a significantly greater than additive or synergistic effect on T cell function.

Figure 7:
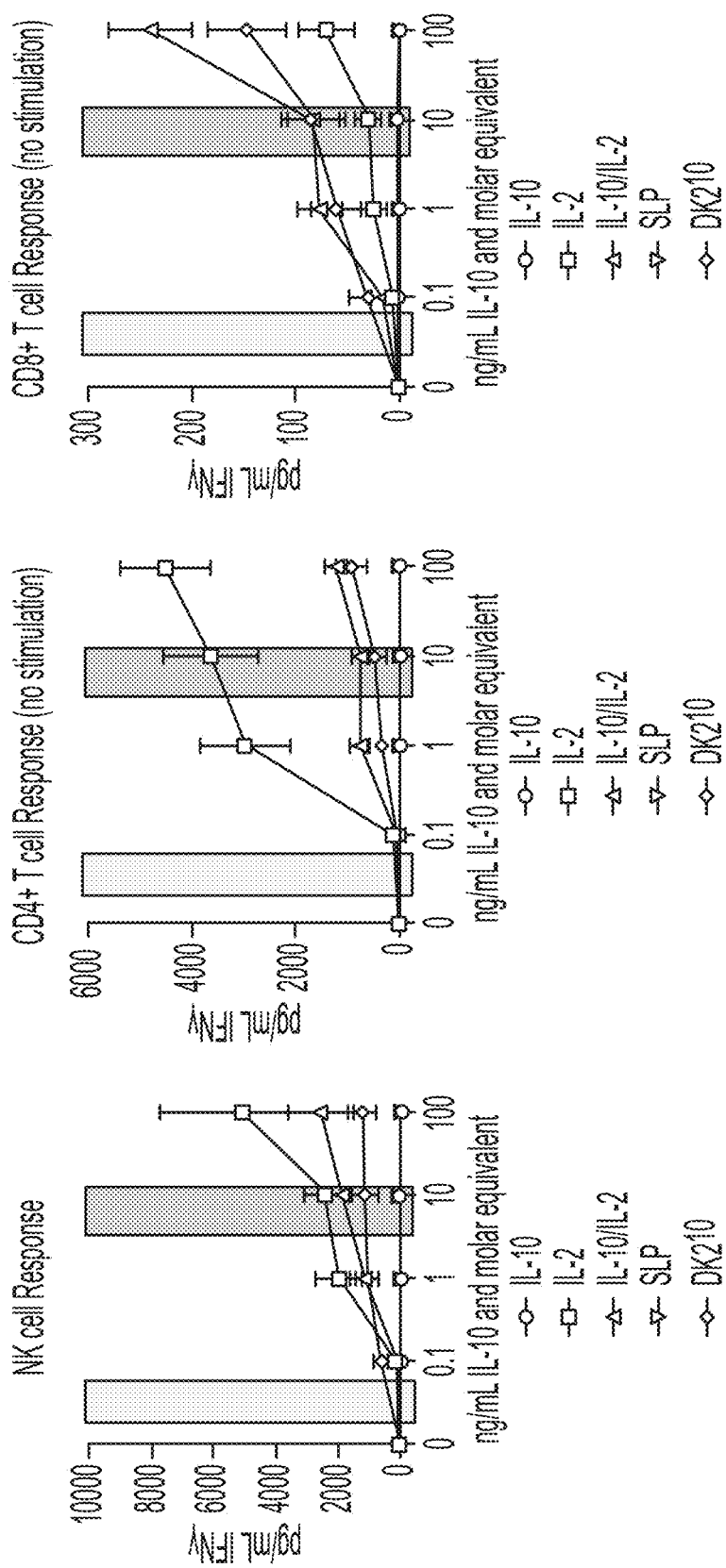

IL-2 toxicity (vascular leak syndrome) is associated with NK (Assier, 2004), and CD4$^+$ T cell (Sivakumar, 2013), proinflammatory cytokine secretion (Guan, 2007; Baluna, 1997). We therefore assessed whether IL-10 could mute the proinflammatory effects of IL-2 on NK cells directly isolated from blood. CD4$^+$ and CD8$^+$ T cells (1) directly isolated from blood, (2) exposed to anti-CD3/anti-CD28 plus cytokines to model antigen priming, (3) exposed to cytokines after antigen priming to model exposure in the tumor and, (4) effect of exposure on antigen primed T cell function upon engagement with cognate antigen (FIG. 7). NK cells, CD4$^+$ and CD8$^+$ T cells directly isolated from peripheral blood were treated with a titration of IL-10, IL-2, combination of IL-10 and IL-2, SLP (an optimized variant of DegfrDV07 of SEQ ID No: 31), and DK2$^{10}$egfr for 4 days (FIG. 7). Expected dosing requirements for DK2$^{10}$egfr is once every 4 days suggesting this in vitro exposure models a high concentration of cytokines (up to 100 ng/mL) for 4 days, far exceeding the expected $C_{max}$ exposure. The data indicates that the addition of IL-10 to IL-2 as individual cytokines or tether together as DK2$^{10}$egfr suppresses IL-2 mediated induction of IFNγ secretion from NK, CD4$^+$ and CD8$^+$ T cells by ~50%, ~80% and ~50% respectively at 5-10 ng/mL. At the expected therapeutic dose of 0.01 ng/mL, little to no IFNγ is induced by the combined cytokines DK2$^{10}$egfr.

Figure 8:
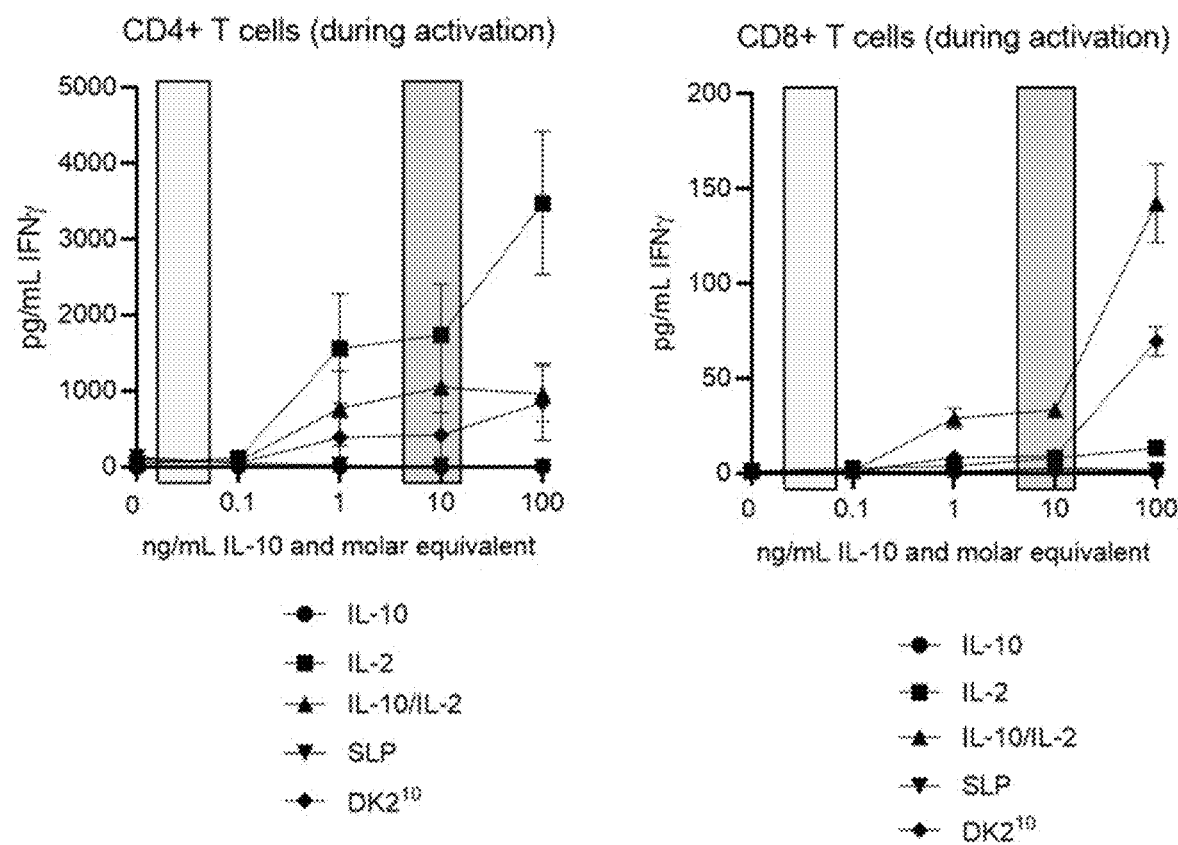

The effect of cytokine exposure during model antigen presentation (immobilized 10 ng/mL anti-CD3/2 ng/mL anti-CD28), (Chan, 2015) was also examined (FIG. 8). The data reveals that the addition of IL-10 to IL-2, and in particular the addition of tethered IL-2 and IL-10 via DK2$^{10}$egfr suppressed CD4$^+$ and CD8$^+$ IFNγ induction by ~75% and ~90% respectively at 10 ng/mL and exhibits no IFNγ induction of 0.01 ng/mL.

Figure 9:
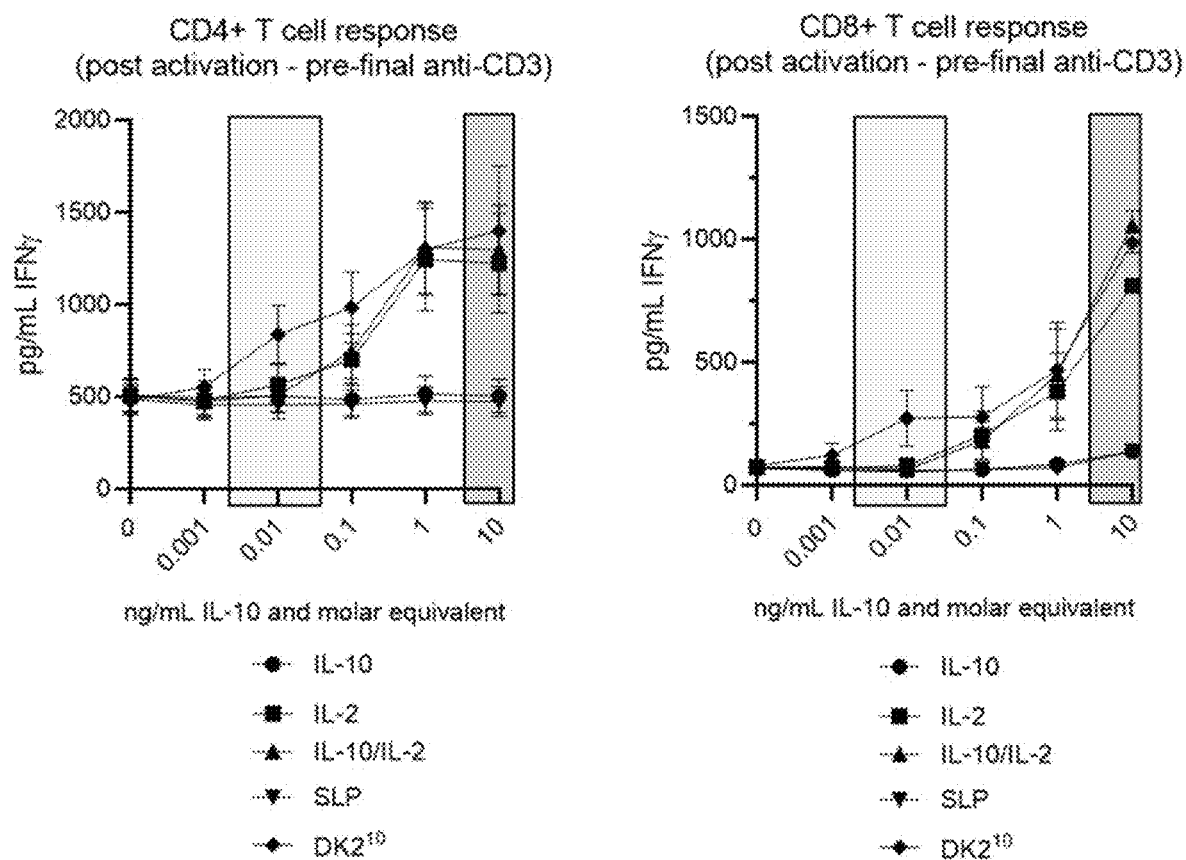

Finally, the induction of IFNγ in CD4$^+$ and CD8$^+$ T cells after antigen exposure to model T cells trafficking in tumors prior to engagement with cognate tumor antigen was examined (FIG. 9). Unexpectedly, the data reveals that the effects of IL-2, IL-10 and IL-2 individually applied versus DK2$^{10}$egfr exert different functions on antigen primed CD4$^+$ and CD8$^+$ T cells. At expected therapeutic concentrations of DK2$^{10}$egfr, DK2$^{10}$egfr potentiates IFNγ secretion more than IL-2 or IL-10 and IL-2 individually applied. At IL-10 and IL-2 expected therapeutic concentrations, DK2$^{10}$egfr, IL-2 and IL-10 and IL-2 individually applied equivalently induce IFNγ secretion from CD4$^+$ and CD8$^+$ T cells. These data collectively indicate the tethering of IL-2 and IL-10 (in the form of DK2$^{10}$) together potentiate antigen specific CD4$^+$ and CD8$^+$ T cell responses while suppressing pro-inflammatory cytokine secretion associated with IL-2 toxicity. Notably, these effects were not impacted by the engraftment of the anti-EGFR CDRs into the anti-ebola scFv scaffolding.

Example 2: IL-10 and IL-2 Dual Cytokine Fusion Protein In Vivo Study

Targeting DV07 via an anti-EGFR scFv (wherein DV07 is fused to a scFv comprising VH and VL obtained from a human anti-ebola ScFv scaffolding comprising 6 engrafted anti-EGFR CDRs; "Degfr:DV07" of SEQ ID No: 31) into the tumor microenvironment by virtue of generating a stably expressed human EGFR CT26 murine colorectal tumor cell line, was previously shown to exhibit superior anti-tumor function when compared with PEG-rHuIL-10. See, U.S. Pat. No. 10,858,412. Using the same in vivo tumor study, $DK2^{10}$egfr was evaluated and compared to Degfr:DV07 in human EGFR expressing CT26 cell murine tumor cell line.

CT26 ($hEGFR^+$) tumor bearing B cell k.o. Balb/C mice, with an average of 100 $mm^3$ tumors were treated with test articles, doses and frequencies as provided shown in Table 1. All test articles were administered subcutaneously in the scruff. All articles were dosed daily for 15 days.

TABLE 1

Test Articles, Doses and Frequencies

| No. | Test article | Dose | Frequency |
|---|---|---|---|
| 1 | Vehicle | 100 μl (control) | Daily |
| 2 | Degfr:DV07 | 1 mg/kg | Daily |
| 3 | $DK2^{10}$ | 1 mg/kg | Daily |
| 4 | $DK2^{10}$ | 2 mg/kg | Daily |
| 5 | $DK2^{10}$ | 4 mg/kg | Daily |

The length and width of tumors were measured every three days by electronic calipers and tumor volume was calculated $((L\times W^2)/2))$. In this example, the terms "Degfr:DV07" is human EGFR targeted DV07; $DK2^{10}$egfr is abbreviated as "$DK2^{10}$" and is human IL-2 coupled with DV07 via the Cetuximab CDR grafted anti-ebola scFv scaffold.

Methods

In vitro cell culture: $CT26^{(hEGFR+)}$ tumor cells (ATCC) were grown to 70% confluency in complete RPMI, 10% FCS, and 10 ug/mL puromycin. Cells were carried for no more than 3 passages in vitro prior to implantation. Cells were removed from cell culture plate using Accutase (Biolegend) and washed in complete RPMI spinning for 10 minutes at 400 g at 4° C.

Tumor Implantation: Tumor cells were implanted at $1\times10^5$ cells/mouse in 100 μL in 50% growth factor reduced Matrigel, 50% RPMI subcutaneous in the right flank of B cell knockout mice.

Results

Comparison of Degfr:DV07 and $DK2^{10}$ on tumor growth: Targeting DV07 to the tumor microenvironment via binding to the EGFR present on the stably transfected tumor cells was previously show to be effective. See U.S. Pat. No. 10,858,412. Using the same tumor system, Degfr:DV07 versus $DK2^{10}$was compared.

Tumors were measured three times a week (Table 2). Female Balb/C B cell knockout mice with 75 $mm^3$ $CT26^{(hEGFR+)}$ tumors were treated subcutaneously with the test articles and dosing frequencies illustrated in Table 2.

TABLE 2

Raw Data

| Animal # | Ear Tag # | Group/Dosing Material | Day 0 TVM | Day 1 TVM | Day 3 TVM | Day 6 TVM | Day 8 TVM | Day 10 TVM | Day 13 TVM | Day 15 TVM | Day 17 TVM |
|---|---|---|---|---|---|---|---|---|---|---|---|
| D07-117-005 | 305 | 1. Vehicle | 57 | 107 | 379 | 921 | 1128 | 1664 | | | |
| D07-117-011 | 311 | | 52 | 75 | 194 | 373 | 651 | 1211 | | | |
| D07-117-012 | 312 | | 27 | 64 | 108 | 247 | 578 | 1230 | | | |
| D07-117-013 | 313 | | 33 | 152 | 407 | 542 | 725 | 1187 | | | |
| D07-117-014 | 314 | | 66 | 88 | 515 | 1274 | 1251 | 2461 | | | |
| | | | 47 | 97 | 321 | 671 | 867 | 1550 | | | |
| D07-117-003 | 303 | 2. DegfDV07 1 mg/kg | 48 | 90 | 81 | 84 | 90 | 130 | 508 | 672 | 573 |
| D07-117-006 | 306 | | 62 | 105 | 218 | 396 | 656 | 1195 | 1709 | 2291 | 3610 |
| D07-117-007 | 307 | | 56 | 80 | 122 | 131 | 215 | 333 | 595 | 776 | 1008 |
| D07-117-008 | 308 | | 37 | 84 | 145 | 420 | 775 | 1124 | 2293 | 2850 | 2781 |
| D07-117-017 | 317 | | 35 | 83 | 132 | 146 | 212 | 343 | 412 | 637 | 833 |
| | | | 48 | 89 | 140 | 235 | 390 | 625 | 1103 | 1445 | 1761 |
| D07-117-001 | 301 | 3. DK2$^{10}$ 1 mg/kg | 57 | 107 | 286 | 478 | 638 | 927 | 1565 | 2567 | 2584 |
| D07-117-004 | 304 | | 55 | 183 | 24 | 192 | 145 | 392 | 735 | 788 | 1320 |
| D07-117-015 | 315 | | 38 | 68 | 78 | 88 | 30 | 167 | 564 | 678 | 984 |
| D07-117-018 | 318 | | 54 | 103 | 77 | 41 | 9 | 21 | 26 | 49 | 24 |
| D07-117-020 | 320 | | 38 | 65 | 45 | 0 | 0 | 0 | 0 | 0 | 0 |
| | | | 48 | 105 | 145 | 160 | 164 | 302 | 578 | 816 | 982 |
| D07-117-024 | 324 | 4. DK2$^{10}$ 2 mg/kg | 69 | 116 | 57 | 9 | 0 | 0 | 0 | 0 | 0 |
| D07-117-029 | 329 | | 40 | 87 | 134 | 34 | 52 | 135 | 361 | 391 | 624 |
| D07-117-030 | 330 | | 32 | 37 | 141 | 96 | 118 | 339 | 641 | 912 | 1289 |
| D07-117-031 | 331 | | 66 | 83 | 68 | 0 | 0 | 0 | 0 | 0 | 0 |
| D07-117-039 | 339 | | 32 | 64 | 117 | 239 | 439 | 878 | 1394 | 1675 | 2233 |
| | | | 48 | 77 | 103 | 75 | 122 | 271 | 479 | 596 | 829 |
| D07-117-019 | 319 | 5. DK2$^{10}$ 4 mg/kg | 21 | 77 | 34 | 61 | 95 | 261 | 550 | 732 | 1127 |
| D07-117-032 | 332 | | 56 | 111 | 34 | 0 | 0 | 0 | 0 | 0 | 0 |
| D07-117-034 | 334 | | 50 | 49 | 125 | 49 | 27 | 0 | 0 | 0 | 0 |
| D07-117-037 | 337 | | 56 | 120 | 135 | 146 | 133 | 272 | 655 | 886 | 1413 |
| D07-117-038 | 338 | | 59 | 114 | 74 | 63 | 36 | 97 | 270 | 380 | 553 |
| | | | 48 | 94 | 80 | 64 | 58 | 126 | 295 | 400 | 618 |

For this experiment, the CT26$^{(hEGFR+)}$ cells were implanted at 1×10$^5$ cells in 50% growth factor reduced Matrigel to limit immunization of the mice against tumor antigens.

Figure 10:
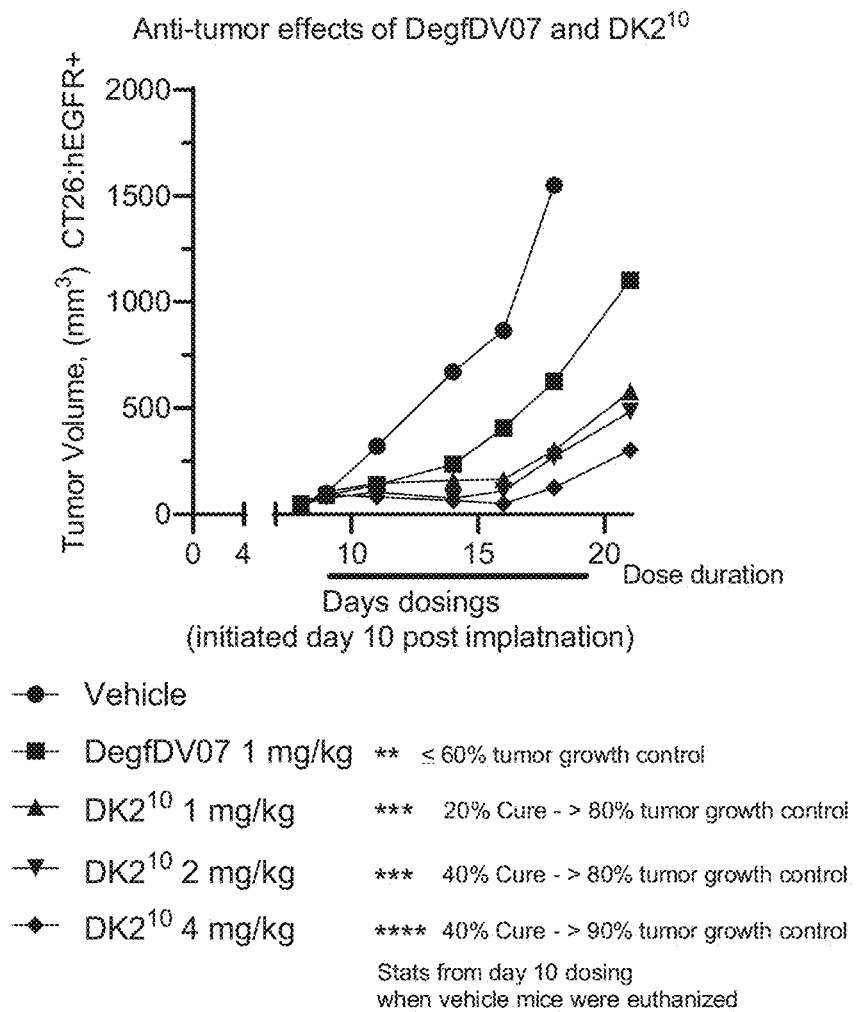

The anti-tumor effect of Degfr:DV07 at 1 mg/kg was compared to the same dose of DK210 as well as 2 and 4 mg/kg doses (FIG. 10). 1 mg/kg daily dosing of DK2$^{10}$ exerts superior anti-tumor function compared to 1 mg/kg daily dosing of Degfr:DV07. 2 and 4 mg/kg doses of DK2$^{10}$ exert more anti-tumor function than 1 mg/kg.

Figure 11:
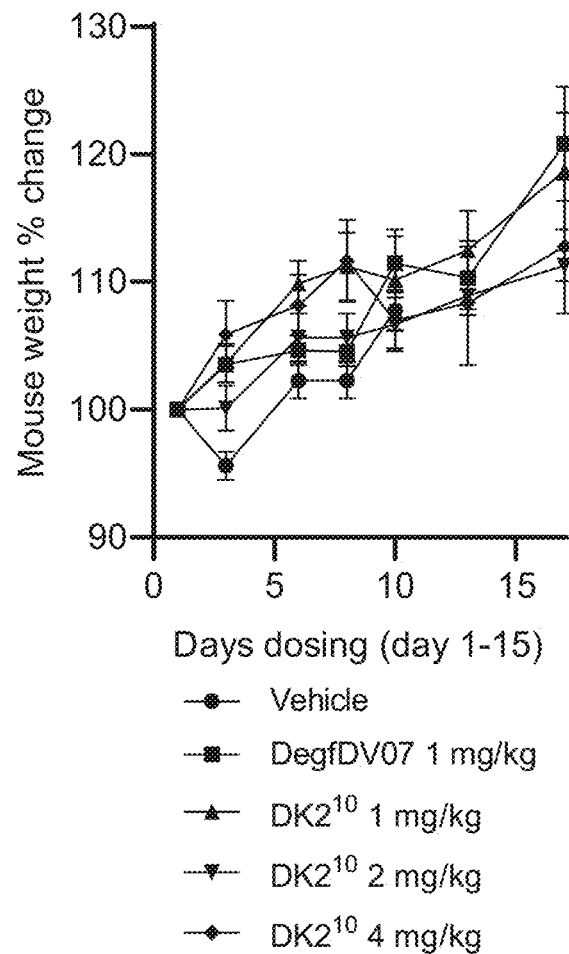

Safety Assessment of DK2$^{10}$: To test the safety of DK2$^{10}$ dosing the weight of tumor bearing mice treated with Degfr:DV07 and DK2$^{10}$ was evaluated (FIG. 11). There are no apparent effects of dosing either Degfr:DV07 or DK2$^{10}$ on the weight of the mice.

Figure 12:
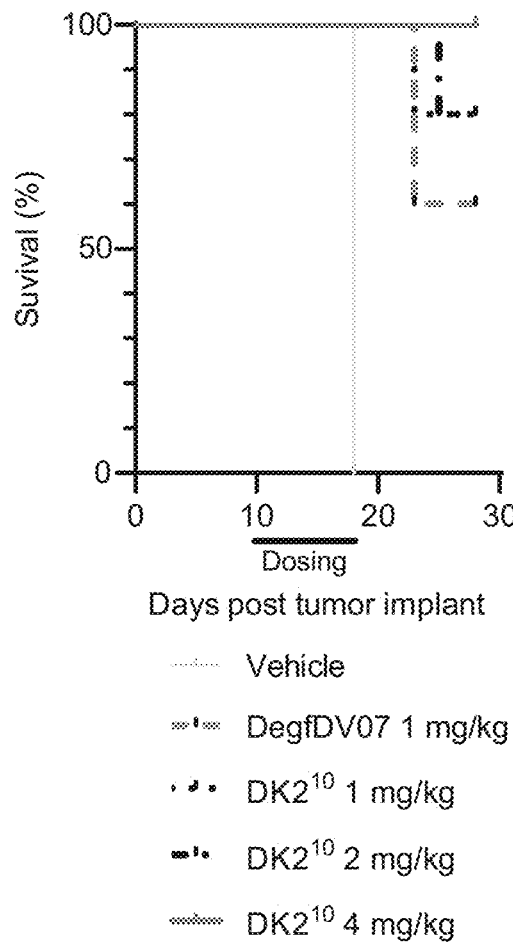
FIG. 12 is an in vivo CT26 (hEGFR$^+$) tumor mouse model study comparing survival of mice treated Degfr:DV07 and DK2$^{10}$.
Figure 13:
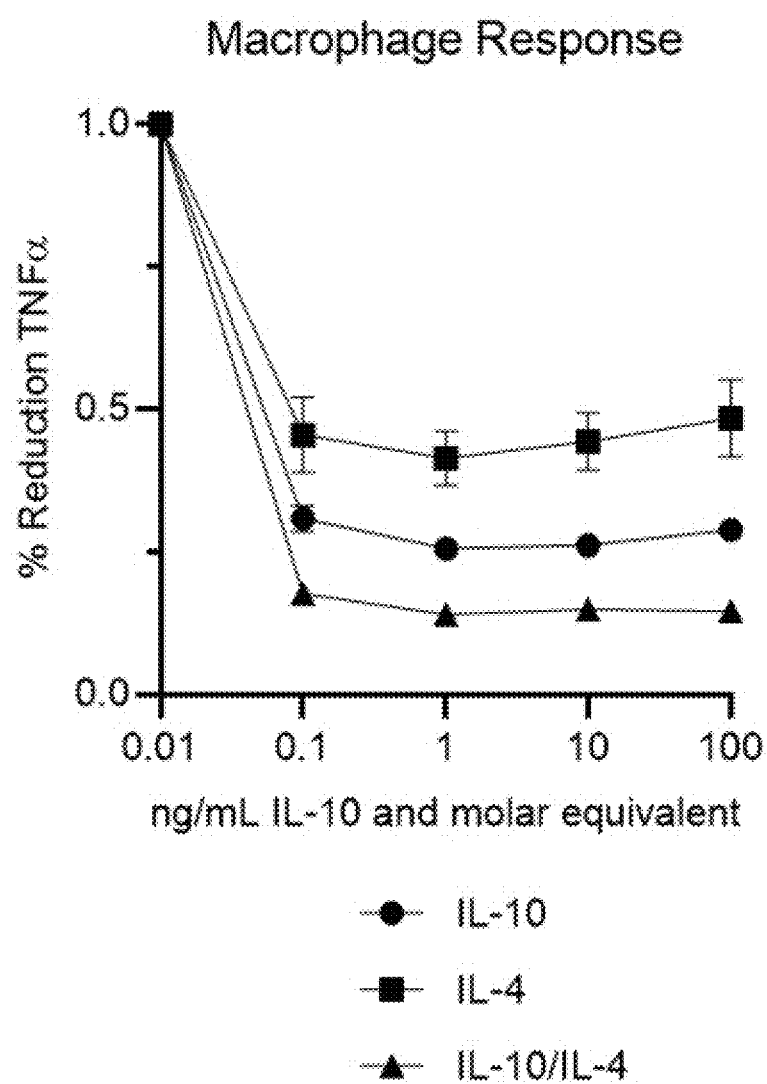
FIG. 13 is a titration study for IL-10, IL-4, and IL-10 and IL-4 on the percent reduction of TNFα secretion from monocytes.
Figure 14:
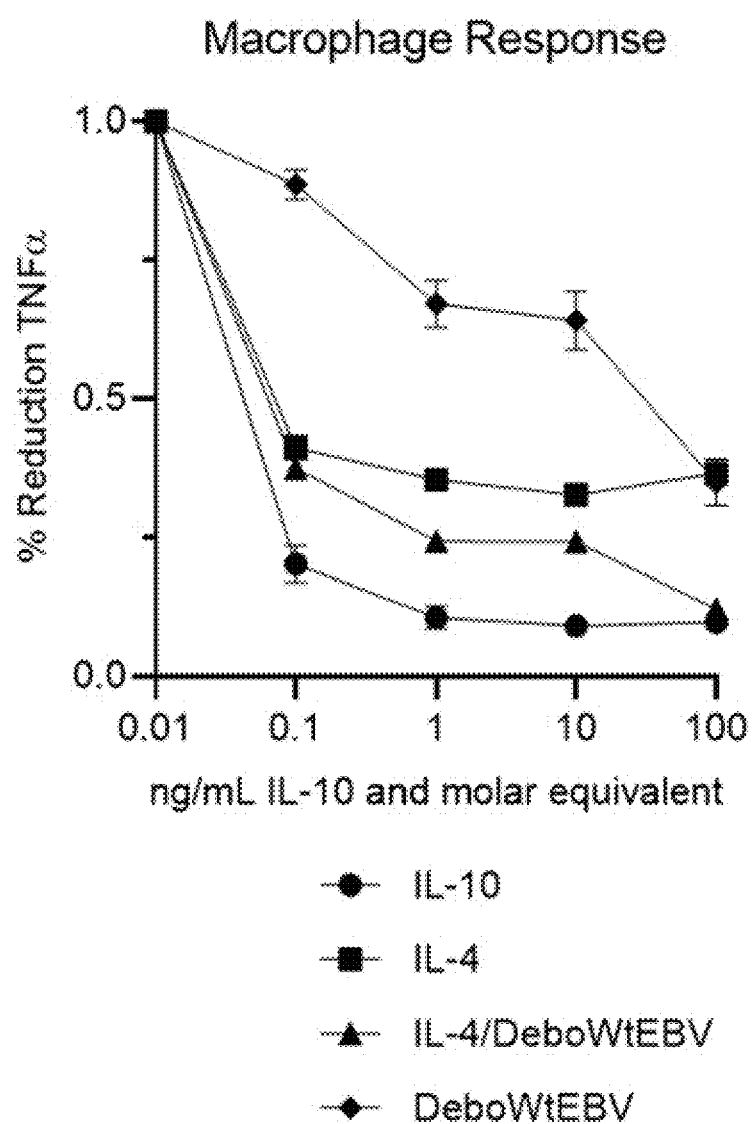
FIG. 14 is a titration study for IL-10, IL-4, IL-4 and DeboWtEBV, and DeboWtEBV alone on the percent reduction of TNFα secretion from monocytes.

Effect of Degfr:DV07 and DK2$^{10}$ dosing on survival: The survivability of CT26$^{(hegfr+)}$ tumor bearing mice to DK2$^{10}$ was assessed (FIG. 12).

All tumors in the vehicle treatment mice were too large by IAACUC stipulation by day 17. 100%, 80%, 80% and 60% of mice were alive in the 4 mg/kg, 2 mg/kg and 1 mg/kg DK210 and Degfr:DV07 1 mg/kg treatment groups at day 30 respectively.

These data collectively suggest coupling a high affinity IL-10 variant (DV07) to IL-2 and targeting both molecules to the tumor microenvironment (via DK2[10]egfr) prevents overt IL-2 mediated toxicity at therapeutically effective doses. Engrafting anti-EGFR CDRs into the scFv scaffolding comprising VH and VL regions obtained from a human anti-ebola scaffolding does not impact the combined effects of IL-10 and IL-2, rather the anti-EGFR CDRs act as a means to concentrate the DK2[10] molecule in the tumor microenvironment. We believe that engrafting CDRs from any antibody (with appropriate optimization) that targets the tumor microenvironment will result in the same or similar effect observed.

Example 3: IL-10 and IL-4 Dual Cytokine Fusion Protein

In Crohn's patients, high dose IL-10 led to diminished anti-inflammatory responses concomitant with increased IFNγ. To determine whether combining a cytokine with IL-10 would enhanced the anti-inflammatory function of IL-10 and suppress IL-10's stimulatory (IFNγ potentiation) function, IL-10 and IL-4 dual cytokine fusion proteins were generated. The inventor unexpectedly discovered that the combined treatment of IL-10 and IL-4 on monocytes more potently suppressed LPS induced inflammatory responses than either IL-10 or IL-4 alone (discussed in more detail below). In addition, IL-4 suppressed IL-10 mediated potentiation of IFNγ in CD8+ T cells. Utilizing similar methods and rational for designing DK2[10]egfr (described above in Examples 1 and 2), IL-4 or various IL-4 variants were coupled to IL-10 or IL-10 variants as a fusion construct (see FIG. 17 as a representative diagram) to enhance the suppressive function of IL-10. The resulting class of molecules was a termed DK4[10].

Table 3 provides a summary of the various molecules studied including cytokines and various DK4[10] fusion molecules.

TABLE 3

Tested Molecules

| Molecule | Seq. ID No. | Format | Target |
|---|---|---|---|
| rhIL-10 | 1 | Cytokine | NA |
| rhIL-4 | 43 | Cytokine | NA |
| DeboDV06 | 21 | Anti-ebola scaffold coupled to monomers of DV06 | None |
| DeboDV07 | 25 | Anti-ebola scaffold coupled to monomers DV07 | None |
| DK4[10]DV06 | 46 | Anti-ebola scaffold coupled to wild type IL-4 and monomers of DV06 | None |
| DK4[10]HADeglyDV06mCD14 | 47 | Anti-ebola scaffold grafted with anti-mCD14 CDR's coupled to the high affinity, non-glycosylated IL-4 (T13D) and monomers of DV06 | Murine CD14 |
| DK4[10]HADeglyDV07mCD14 | 48 | Anti-ebola scaffold grafted with anti-mCD14 CDR's coupled to the high affinity, non-glycosylated IL-4 (T13D) and monomers of DV07 | Murine CD14 |
| DK4[10]ngDV06mCD14 | 49 | Anti-ebola scaffold grafted with anti-mCD14 CDR's coupled to the non-glycosylated IL-4 (N38A) and monomers of DV06 | Murine CD14 |
| DK4[10]ngDV07mCD14 | 50 | Anti-ebola scaffold grafted with anti-mCD14 CDR's coupled to the non-glycosylated IL-4 (N38A) and monomers of DV07 | Murine CD14 |
| DK4[10]ngDV06mMAdCAM | 51 | Anti-ebola scaffold grafted with anti-mMAdCAM CDR's coupled to the non-glycosylated IL-4 (N38A) and monomers of DV06 | Murine MAdCAM |

The following molecules and combination of molecules were tested for their effects on monocyte/macrophages and CD8+ T cells isolated by magnetic bead positive selection, derived from peripheral blood mononuclear cells (PBMC) preparations from healthy donors:

1. IL-4;
2. IL-10;
3. IL-4 in combination with IL-10;
4. DeboWtEBV;
5. DeboWtEBV in combination with IL-4;
6. DeboDV06;
7. DeboDV06 in combination with IL-4;
8. DeboDV07;
9. DeboDV07 in combination with IL-4;
10. $DK4^{10}$ comprising wild type IL-4 and DV06 ("4DeboDV06");
11. $DK4^{10}$ comprising high affinity, non-glycosylated IL-4 (T13D) and DV06 targeted to mCD14;
12. $DK4^{10}$ comprising high affinity, non-glycosylated IL-4 (T13D) and DV07 targeted to mCD14;
13. $DK4^{10}$ comprising non-glycosylated IL-4 (N38A) with DV06 targeted to mCD14;
14. $DK4^{10}$ comprising non-glycosylated IL-4 (N38A) with DV07 targeted to mCD14; and
15. $DK4^{10}$ comprising non-glycosylated IL-4 with DV06 targeted to mMAdCAM.

Methods

Figure 15:
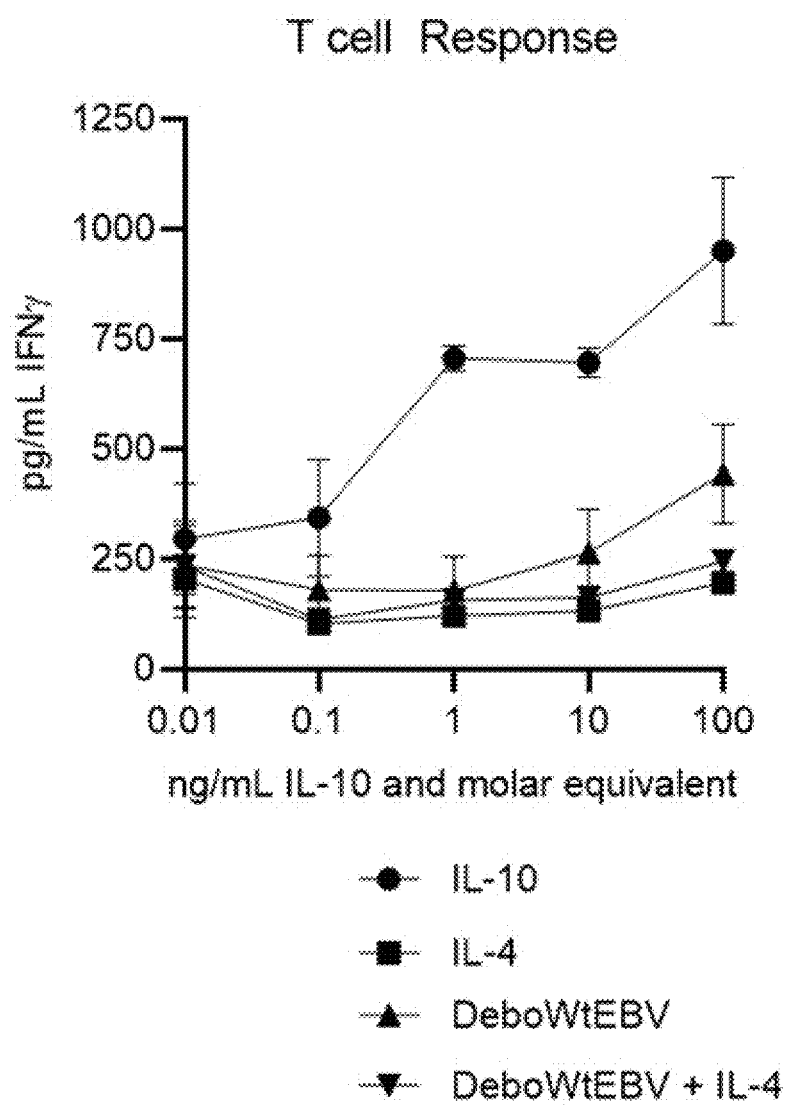
FIG. 15 is a T-cell IFNγ potentiation assay comparing DeboWtEBV and IL-4 against DeboWtEBV alone.
Figure 16:
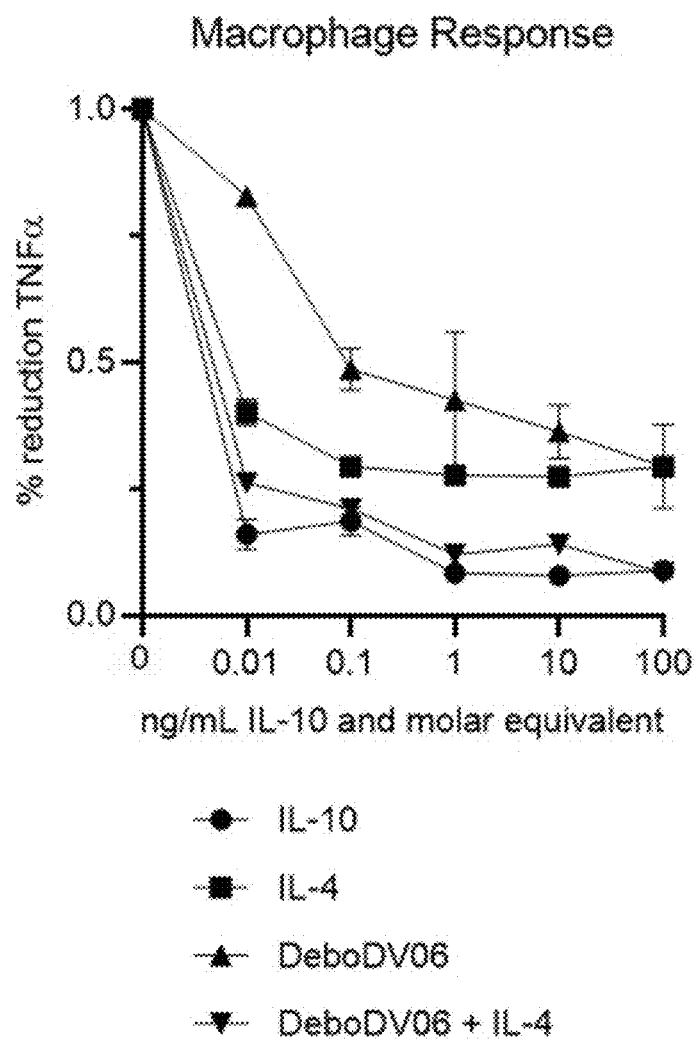
FIG. 16 is a titration study evaluating of IL-10, IL-4, DeboDV06, and DeboDV06 in combination with IL-4 on suppressing LPS induced TNFα secretion by monocytes/macrophages.

PBMC and CD8+ T-cell isolation: Both macrophages and CD8+ T cells were isolated from PBMC or leukopak using anti-CD14 (monocytes) or anti-CD8 (CD8+ T cells) magnetic microbeads by magnet assisted cell sorting.

Cellular Assay—Monocyte/Macrophage cell response to cytokines and lipopolysaccharide (LPS): In this assay, PMBC derived monocytes are isolated with CD14 positive selection beads, plated at $2\times10^5$ cells/well and exposed to a titration cytokines and 10 ng/mL LPS. After 18 hours, supernatants are evaluated by ELISA for secreted proinflammatory cytokines. The percent reduction of TNFα is plotted to denote the effect the cytokine or test article exerts on LPS. This assay most appropriately mimics the response of monocytes to cytokines and bacterially derived proinflammatory products in peripheral blood.

Cellular Assay—CD8+ T cells: Multiple CD8+ T cells assays were used. Initially, CD8+ T cells were derived from PBMC using CD8+ positive magnetic selection beads, plated at $2\times10^1$ cells/well and were exposed to a titration of cytokines or test articles under the following conditions:

(i) 4 days alone,
(ii) 3 days to plate bound anti-CD3/anti-CD28 in the presence of cytokines to mimic how these molecules affect the cells response to cognate antigen presentation,
(iii) post anti-CD3/anti-CD28 for 3 days to mimic how antigen stimulated cells respond to these cytokines and novel factors as the cells enter the tumors, and
(iv) T cell receptor triggered IFNγ secretion was evaluated after 4 hours from the cells exposed in vitro to mimic how T cells in the tumor microenvironment respond to cognate antigen exposure.

Both monocyte/macrophage and CD8+ T cells were exposed to a titration of human IL-4, IL-10, DeboWtEBV, DeboDV06 and the various $DK4^{10}$ fusion molecules at 0.1, 1, 10, 100 ng/mL or 0.001, 0.01, 0.1, 1 and 10 ng/mL (or molar equivalent) for overnight or 3-4 days as stated, with all conditions run in duplicate. Anti-inflammatory (monocytes/macrophages) and stimulatory effects (CD8+ T cells) of these molecules were used to determine the most effective anti-inflammatory pair of cytokines.

Protein measurements: Macrophage cell culture media was assayed by ELISA for TNFα and CD8+ T cell culture media was assayed by ELISA for IFNγ. DeboDV06, 4DeboDV06 and the various $DK4^{10}$ fusion molecules were assessed by Nanodrop OD280 nM using each proteins' respective extinction coefficient and the concentration was corroborated by Coomassie stained SDS-PAGE gel band intensity.

Results

Development of Rational for IL-10 and IL-4 combination: IL-10 has been reported to suppress TNFα secretion by macrophages in response to LPS (Malefyt, Interleukin 10 Inhibits Cytokine Synthesis by Human Monocytes An Autoregulatory Role of IL-10 Produced by Monocytes, 1991; Moore, 2001). IL-4 has been reported to suppress LPS induced TNFα secretion from human monocytes (Hart, Potential antiinflammatory effects of interleukin 4: Suppression of human monocyte tumor necrosis factor ca, interleukin 1, and prostaglandin E2, 1989) and human peritoneal macrophages (Hart, 1991).

To determine the effects of combining IL-4 and IL-10 on the suppression of monocyte pro-inflammatory cytokine secretion in response to LPS as an inflammatory stimulus, peripheral blood monocytes were isolated from healthy donor PBMC by magnetic bead positive selection. The isolated monocytes were exposed to a titration of IL-10, IL-4, and a combination of IL-10 and IL-4 (FIG. 13). Assessment of healthy human macrophage response to the titration, (0.1, 1, 10, 100 ng/mL) of human IL-10, IL-4, and the combination of IL-10 and IL-4 demonstrates that both IL-10 alone and IL-4 alone are capable of suppressing LPS induced TNFα secretion. However, the combination of IL-10 and IL-4 together is superior in suppressing TNFα secretion to either cytokine alone.

Effect of IL-4 and DeboWtEBV on monocyte/macrophages: DeboWtEBV is comprised of the wild type EBV IL-10 coupled to the half-life extended VH and VL scaffolding system derived from a human anti-ebola antibody (previously described in U.S. Pat. No. 10,858,412). DeboWtEBV has been shown to suppress TNFα secretion. The isolated monocytes were exposed to a titration of IL-10, IL-4, DeboWtEBV, and DeboWtEBV in combination with IL-4 (FIG. 14). The combination of IL-4 with DeboWtEBV together suppress LPS induced TNFα secretion from monocytes in a manner that is superior to either IL-4 or DeboWtEBV alone.

Effect of IL-4 and DeboWtEBV on T cells: In addition to assessing combined suppressive effects of IL-10 and IL-4 on monocyte/macrophages, the combined effects of IL-4 and DeboWtEBV on T cells were also examined (FIG. 15). DeboWtEBV induces less IFNγ from CD8+ T cells compared to the same molar concentration of IL-10. The combination of IL-4 with DeboWtEBV reduce IFNγ more than that induced by DeboWtEBV alone at 100 ng/mL.

Effect of IL-4 and DeboDV06 on monocytes/macrophages: To determine if the suppressive effects of the IL-10 could be increased, a higher affinity variant of the EBV IL-10, denoted as DV06 was assessed. DV06 contains the point mutation (A751) and is coupled to the half-life extended VH and VL scaffolding system derived from a human anti-ebola antibody (previously described in U.S. Pat. No. 10,858,412) by substituting wild type EBV IL-10 with DV06. Isolated monocytes were exposed to a titration of IL-10, IL-4, DeboDV06, and DeboDV06 in combination with IL-4 (FIG. 16). DeboDV06 exhibits increased suppressive function relative to DeboWtEBV (compared with FIG. 15), and the combination of DeboDV06 with IL-4 similarly increases the suppressive function on monocyte/macrophage response to LPS. The combination of IL-4 with DeboDV06 suppress LPS induced TNFα secretion from monocytes in a manner that is superior to either IL-4 or DeboDV06 alone.

Evaluation of IL-4 coupled with DeboDV06 (in DK4$^{10}$ form): The data suggest that combining IL-4 with the IL-10 variant, DV06 (which is an enhanced affinity variant of wild type EBV IL-10), suppress LPS mediated monocyte inflammatory responses in a manner superior to either molecule alone. Accordingly, IL-4 was coupled to the DeboDV06 molecule by expressing IL-4 in the linker between the VH and VL of the half-life extended scaffold molecule (FIG. 17), creating the first member of the DK4$^{10}$ class of molecules denoted as "IL-4DeboDV06" or "4DeboDV06", which are non-targeting forms of the dual cytokine fusion protein (i.e. comprising the 6 CDR regions from the anti-ebola antibody).

Figure 18:
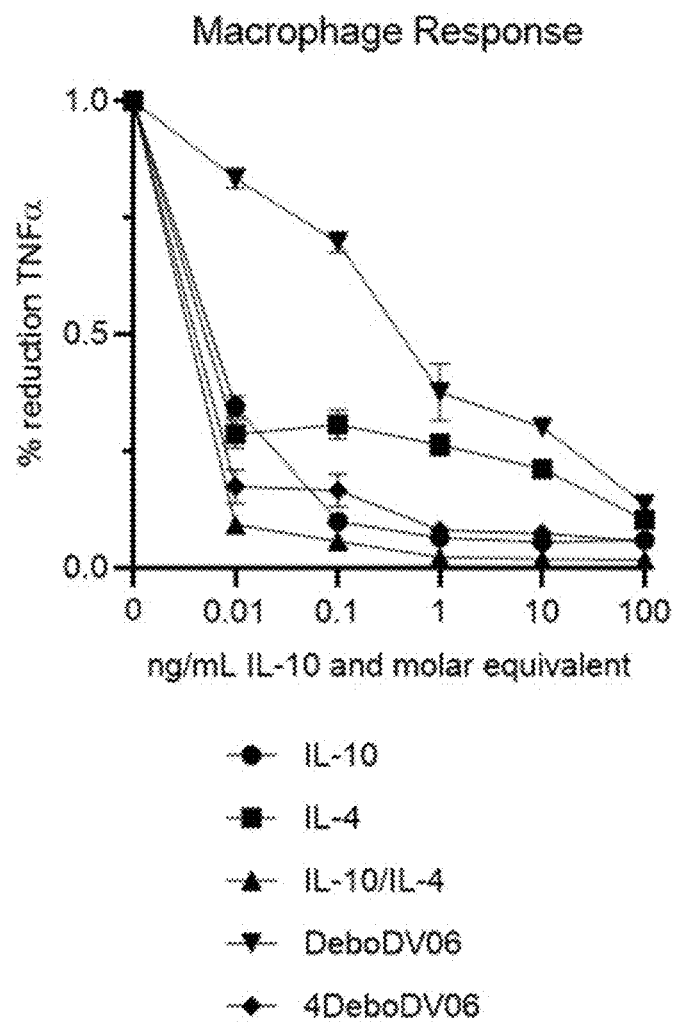
FIG. 18 is a titration study evaluating IL-4DeboDV06 in DK4$^{10}$ form (also known as "4DeboDV06") in comparison to IL-10, IL-4, DeboDV06, and IL-10 in combination with IL-4 on suppressing LPS induced TNFα secretion by monocytes/macrophages.

Effect of IL-4DeboDV06 (in DK4$^{10}$ form) on monocyte/macrophages: To determine whether IL-4DeboDV06, in DK4$^{10}$ form, suppresses LPS induced inflammatory responses, isolated monocytes were exposed to a titration of IL-10, IL-4, DeboDV06, IL-10 in combination with IL-4, and IL-4DeboDV06 (FIG. 18). IL-4DeboDV06 in DK4$^{10}$ form suppresses LPS induced TNFα secretion from monocytes in a manner that is superior to either IL-4 or DeboDV06 alone, but not quite as well as IL-4 plus IL-10, especially at lower concentrations.

Figure 19:
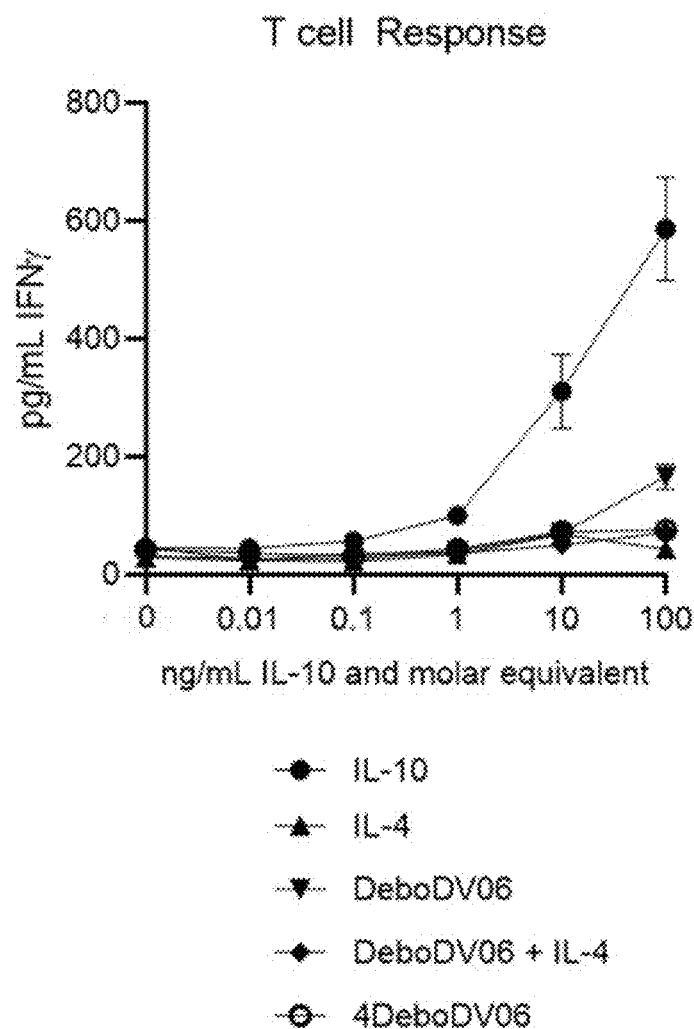
FIG. 19 is a titration study evaluating IL-4DeboDV06 in DK4$^{10}$ form (also known as "4DeboDV06") in comparison to IL-10, IL-4, DeboDV06, and DeboDV06 in combination with IL-4 on CD8$^+$ T cells.

Effect of IL-4DeboDV06 (in DK4$^{10}$ form) on CD8$^+$ T cells: The ability of IL-4DeboDV06 to potentiate and induce IFNγ from CD8$^+$ T cells was examined and compared to IL-10, IL-4, DeboDV06, and DeboDV06 in combination with IL-4 (FIG. 19). IL-4DeboDV06 in DK4$^{10}$ form suppresses IFNγ secretion from CD8$^+$ T cells similarly to the combination of DeboDV06 plus IL-4.

Figure 20:
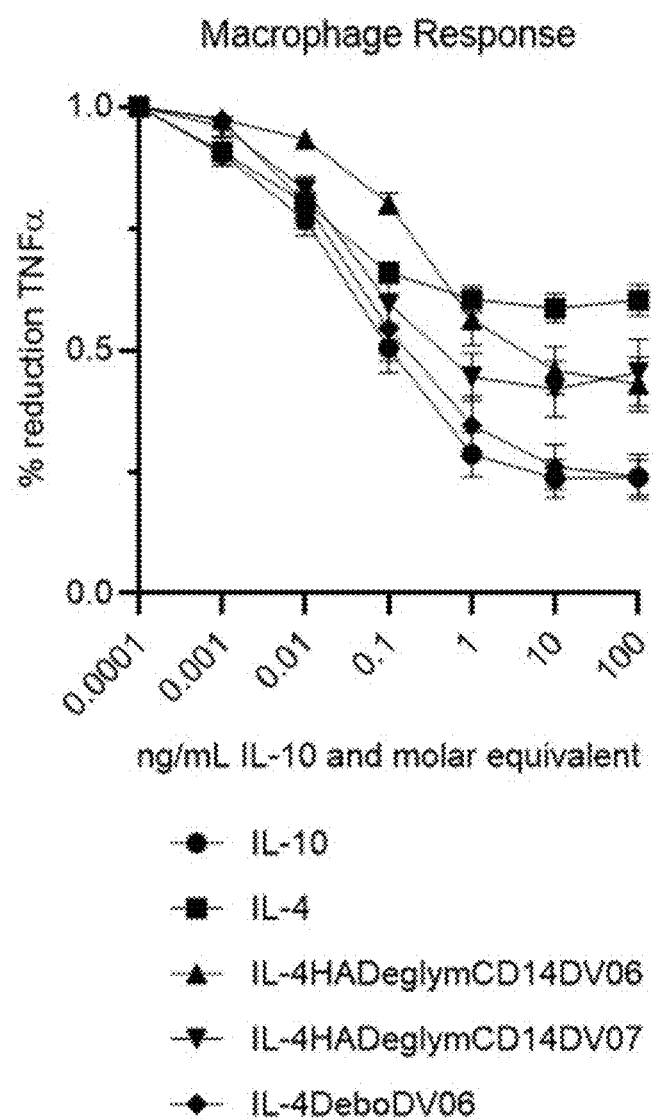
FIG. 20 is a titration study evaluating IL-4HADeglymCD14DV06 and IL-4HADeglymCD14DV07, which are members of the DK4$^{10}$ class of molecules comprising a non-glycosylated (N38A) and high affinity (T13D) form of human IL-4, and compared to IL-10, IL-4, and IL-4DeboDV06 (also known as "4DeboDV06") in DK4$^{10}$ form on suppressing LPS induced TNFα secretion by macrophage/monocytes.

Effect of IL-4HADeglyDmCD14DV06 and IL-4HADeglyDmCD14DV07 (in DK4$^{10}$ form) on monocyte/macrophages: It was determined that the IL-4 amino acid sequence used in manufacturing IL-4DeboDV06 in DK4$^{10}$ form appeared to be glycosylated. Sequence analysis confirmed that a putative N-linked glycosylation variant exists at amino acid position N38 but that glycosylation is not required for function (Li, 2013). Further research suggested that substituting amino acid T13 with an aspartate (D) generated a high affinity IL-4 variant (U.S. Pat. No. 6,028, 176). Both point mutations with substitutions at N38A and T13D were introduced into IL-4 and linked and incorporated into the Debo scaffolding engrafted with 6 CDRs from murine CD14 (FIG. 20). The data suggests that the high affinity, non-glycosylated IL-4 variant (i.e., comprising both the N38A and T13D point mutations) exhibits inferior function in the DK4$^{10}$ coupled format when compared to wild type IL-4 in the same format.

Figure 21:
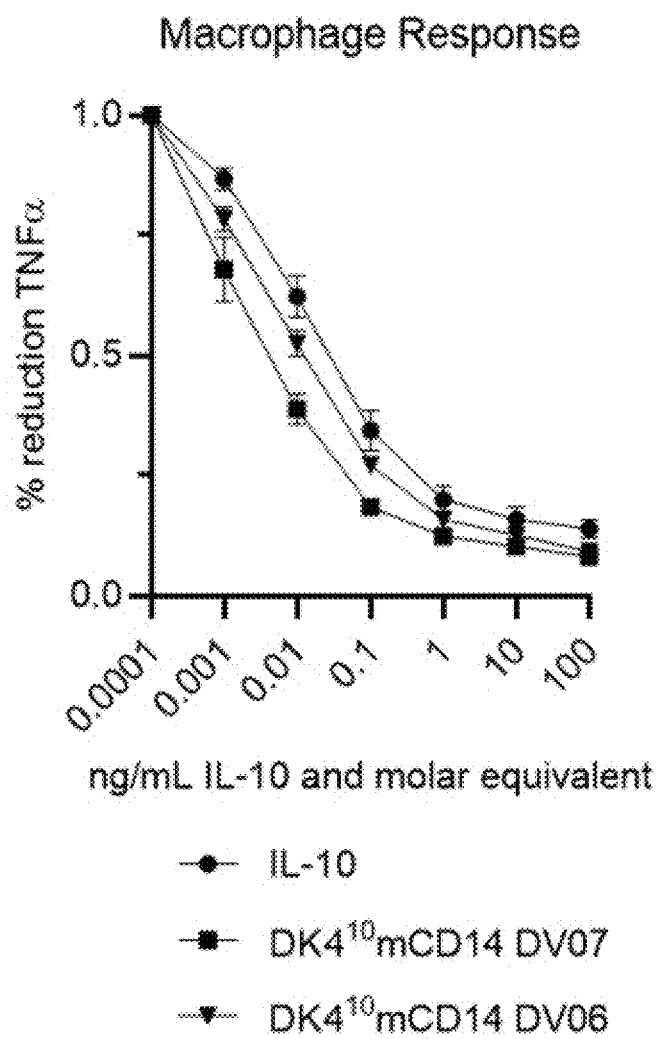
FIG. 21 is a titration study evaluating IL-4ngDmCD14DV06 and IL-4ngDmCD14DV07, which are members of the DK4$^{10}$ class of molecules comprising a single substitution at N38A resulting in a non-glycosylated form of IL4, and compared to IL-10 on suppressing LPS induced TNFα secretion by monocytes/macrophages.

Effect of IL-4ngDmCD14DV06 and IL-4ngDmCD14DV07 (in DK4$^{10}$ form) on monocyte/macrophages: The effects of IL-4ngDmCD14DV06 and IL-4ngDmCD14DV07 in DK4$^{10}$ form, which includes an IL-4 variant comprising the N38A substitution, were assessed by assaying for the suppression of LPS induced inflammatory responses by exposing the isolated monocytes to a titration of IL-10, IL-4ngDmCD14DV06 (also known as "DK4$^{10}$mCD14DV06") and IL-4ngDmCD14DV07 (also known as "DK4$^{10}$mCD14DV07") (FIG. 21). An IL-4 variant termed "IL-4ng" is the non-glycosylated form of IL-4 (comprising the N38A substitution, SEQ ID No: 44) that we introduced to improve manufacturability and "mCD14" represents the engraftment of the 6 CDRs from an anti-mCD14 antibody into the Debo scaffolding. Both DK4$^{10}$ (comprising the IL-10 variants of DV06 and DV07) molecules suppress LPS induced TNFα secretion.

Figure 22:
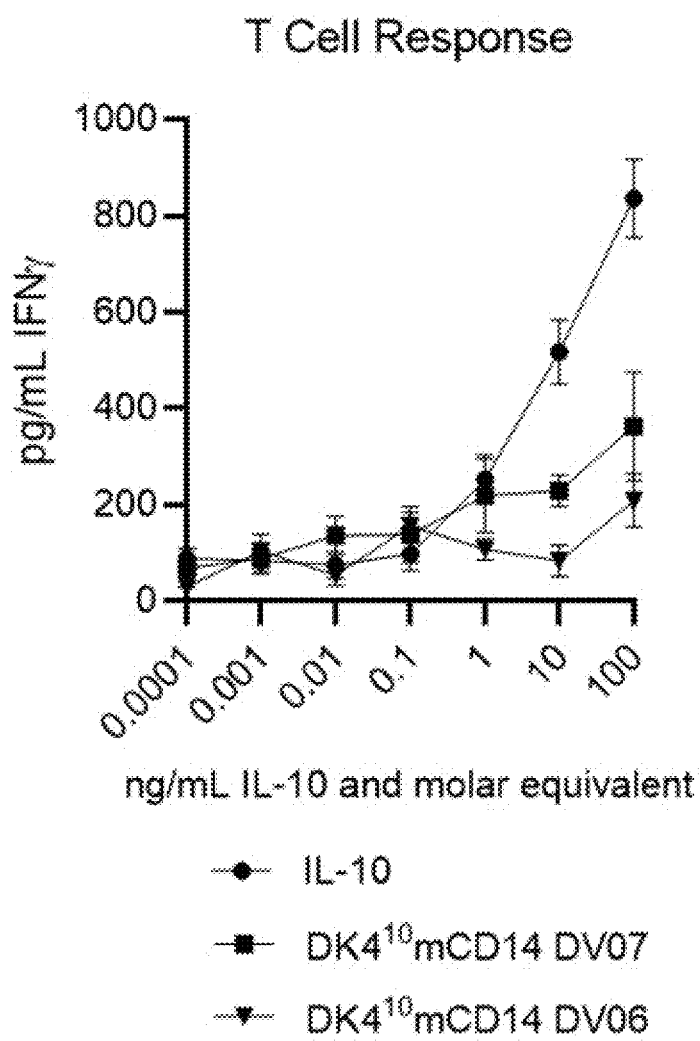
FIG. 22 is a titration study evaluating IL-4ngDmCD14DV06 and IL-4ngDmCD14DV07, which are members of the DK4$^{10}$ class of molecules comprising a single substitution at N38A resulting in a non-glycosylated form of IL4, and compared to IL-10 on mediating IFNγ induction by CD8$^+$ T cells.

Effect of IL-4ngDmCD14DV06 and IL-4ngDmCD14DV07 (in DK4$^{10}$ form) on T cells: The stimulatory effects of IL-10, IL-4ngDmCD14DV06 and IL-4ngDmCD14DV07 in DK4$^{10}$ form (as described above) were assessed on T cells (FIG. 22). Both DK4$^{10}$ (comprising the IL-10 variants of DV06 and DV07) molecules do not induce as much IFNγ secretion as IL-10 from CD8+ T cells. IL-4ngDmCD14DV06 induces slightly less IFNγ secretion at 1-100 ng equivalent molar exposure in comparison to IL-4ngDmCD14DV07.

Figure 23:
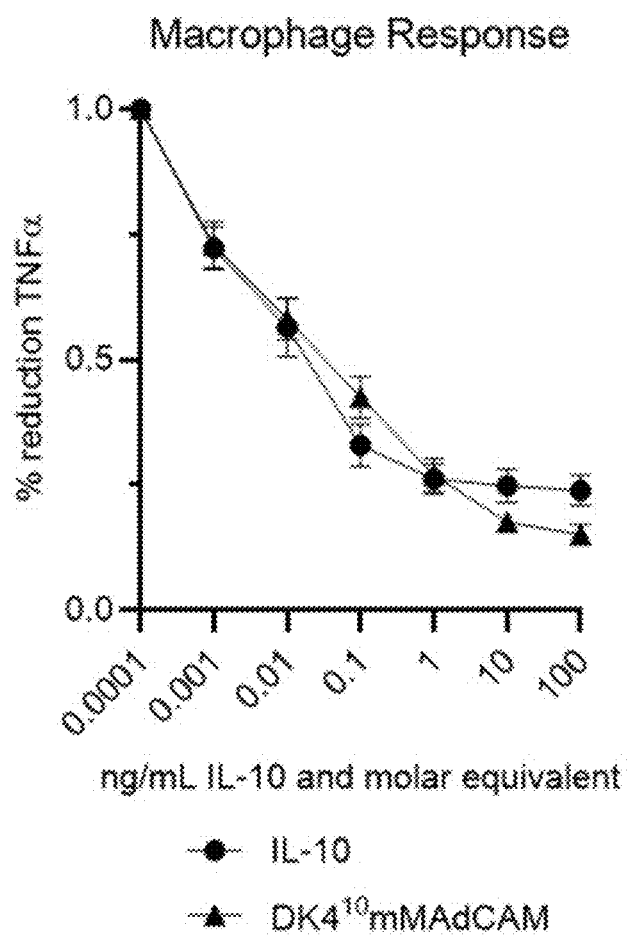
FIG. 23 is a titration study evaluating IL-4ngDmMAdCAMDV06, which are members of the DK4$^{10}$ class of molecules comprising a single substitution at N38A resulting in a non-glycosylated form of IL4, and compared to IL-10 on suppressing LPS induced TNFα secretion by monocytes/macrophage.

Effect of IL-4ngDmDMAdCAMDV06 (in DK4$^{10}$ form) on monocyte/macrophages: The effects of IL-4ngDmMAdCAMDV06 in DK4$^{10}$ form were assessed by assaying the suppression of LPS induced inflammatory response on monocytes/macrophages. IL-4ngDmMAdCAMDV06 is a dual cytokine fusion in DK4$^{10}$ form comprising: (1) an IL-4ng variant that is non-glycosylated (comprising the N38A substitution); (2) the engraftment of the 6 CDRs from a mouse anti-MAdCAM antibody into the Debo scaffolding; and (3) the IL-10 variant DV06. Isolated monocytes/macrophages were titrated with IL-10 or IL-4ngDmMAdCAMDV06 (FIG. 23). IL-4ngDmMAdCAMDV06 suppresses LPS induced TNFα secretion in monocytes/macrophages.

Figure 24:
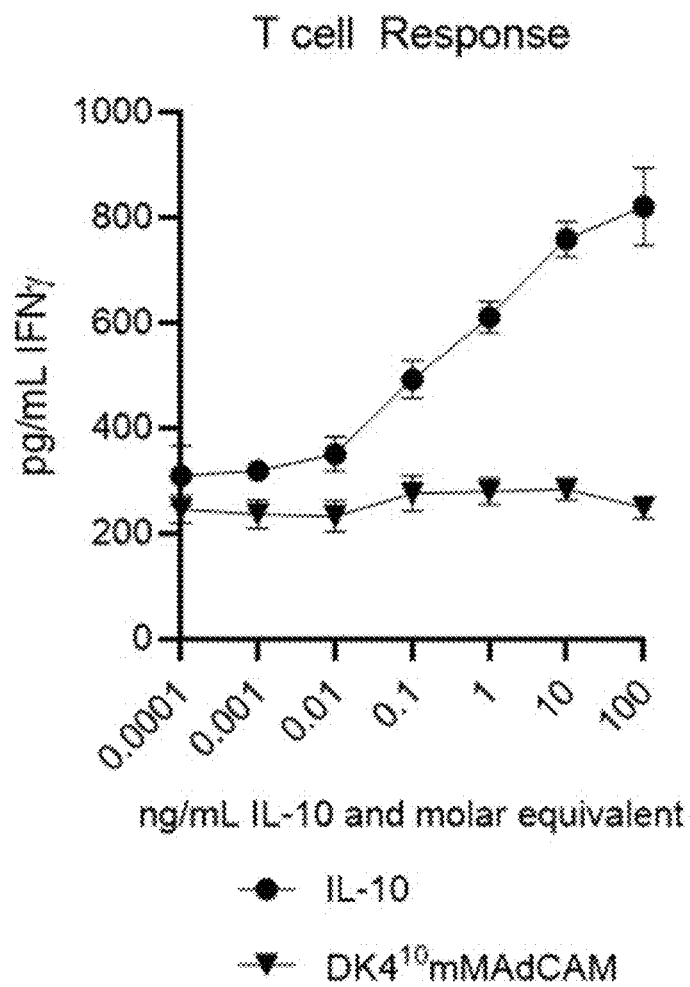
FIG. 24 is a titration study evaluating IL-4ngDmMAdCAMDV06, which are members of the DK4$^{10}$ class of molecules comprising a single substitution at N38A resulting in a non-glycosylated form of IL4, and compared to IL-10 on mediating IFNγ induction by CD8$^+$ T cells.

Effect of IL-4ngDmMAdCAMDV06 (DK4$^{10}$ format) on T cells: We also evaluated the stimulatory effects of IL-10 and IL-4ngDmMAdCAMDV06 (DK4$^{10}$ format) on T cells (FIG. 24). IL-4ngDmMAdCAMDV06 does not induce IFNγ secretion from CD8+ T cells unlike IL-10.

CONCLUSION

These data suggest that IL-4 variants and IL-10 variants can be co-expressed via coupling these two cytokines to a human anti-ebola derived VH/VL scaffold system (i.e., in DK4$^{10}$ form). The combination of IL-4 and IL-10 variants suppresses LPS induced inflammatory responses by monocyte/macrophages while also inhibiting the induction of IFNγ from CD8+ T cells, regardless of the targeting CDR present within the VH and VL scaffolding system (compare 4DeboDV06 to engrafted versions of DK4$^{10}$ comprising CDRs from anti-mCD14 and anti-mMAdCAM).

The anti-ebola derived VH and VL scaffold couples IL-4 and IL-10 variant cytokines effectively and can accept multiple targeting CDR's grafts. The combination of IL-4ng (the IL-4 variant resulting in non-glycosylated IL-4 due to the N38A substitution) with DV06 suppresses LPS mediated TNFα secretion effectively from 0.1-100 ngs/mL and does not induce significant IFNγ from CD8+ T cells in the same dose range.

Example 4: DK4$^{10}$ in the Treatment of Sepsis

Having determined that IL-4ngDmCD14DV06 (also known as "DK4$^{10}$mCD14DV06") was capable of suppressing LPS induced TNFα secretion and tamped down the induction of IFNγ from CD8$^+$ T-cells (see, FIG. 21 and FIG. 22), this molecule was examined in a well-known and conventional sepsis model.

Briefly, wild type Balb/C mice were obtained and acclimated, pursuant standard IACUCU protocols. The mice were maintained on standard chow and water ad libitum with a 12 hour light/dark cycle.

Vehicle, DK4$^{10}$mCD14DV06, was dosed subcutaneously in the animal at the stated dose in 100 milliliters of vehicle buffer at the stated time points either before ("pre") or after ("post") intraperitoneal LPS administration (350 mg/mouse).

Figure 25:
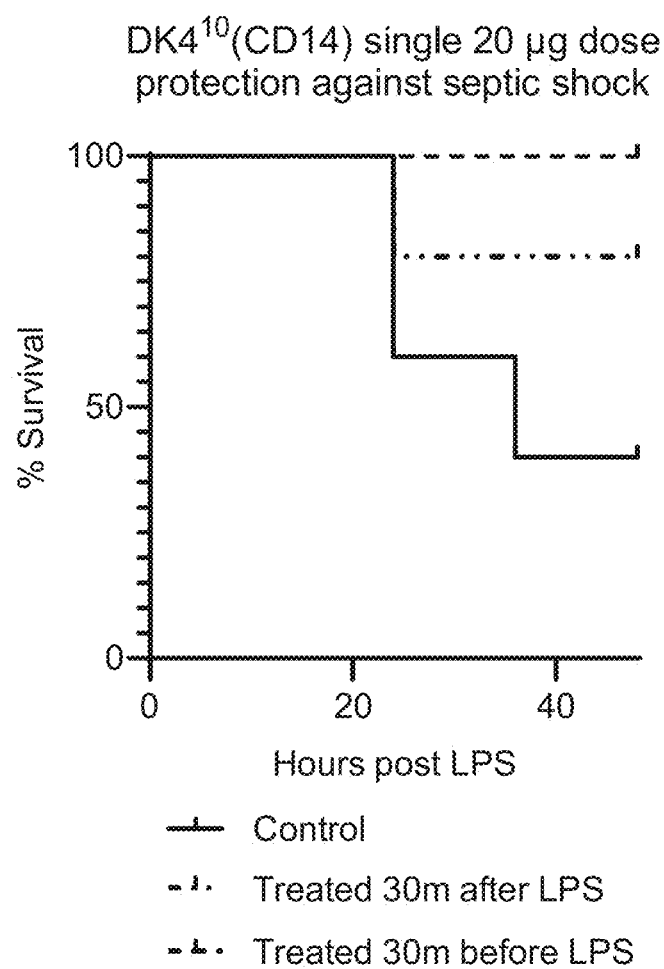
FIG. 25 is an in vivo sepsis mouse model study comparing survival of mice treated with IL-4ngDmMAdCAMDV06 before and after LPS administration.

After 4 days of acclimation, five (5) mice per group were treated with the following:
(1) 1 mg/kg DK410mCD14DV06 30 minutes before LPS administration; and
(2) 1 mg/kg DK410mCD14DV06 30 minutes after LPS administration The mice were evaluated for survival 48 hours after LPS administration. Treatment of mice with DK410mCD14DV06 30 minutes before LPS administration resulted in 100% survivor rate, whereas treatment with DK410mCD14DV06 30 minutes after LPS administration demonstrated protective effects against septic shock (FIG. 25).

The data suggests that coupling an IL-10 variant to an IL-4 variant (IL-4ng) and targeting the two molecules via a Debo scaffolding system with 6 CDRs from a mouse anti-CD14 antibody (e.g., using DK4$^{10}$mCD14DV06) significantly attenuates the inflammatory response and treats septic shock.

This written description uses examples to disclose aspects of the present disclosure, including the preferred embodiments, and also to enable any person skilled in the art to practice the aspects thereof, including making and using any devices or systems and performing any incorporated methods. The patentable scope of these aspects is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Aspects from the various embodiments described, as well as other known equivalents for each such aspect, can be mixed and matched by one of ordinary skill in the art to construct additional embodiments and techniques in accordance with principles of this application.

REFERENCES

Assier, E. (2004). NK Cells and Polymorphonuclear Neutrophils Are Both Critical for IL-2-Induced Pulmonary Vascular Leak Sydrome. *Journal of Immunology*.
Balce, D. R. (2011). Alternative activation of macrophages by IL-4 enhances the proteolytic capacity of their phagosomes through synergistic mechanisms. *Blood*.
Baluna, R. (1997). Vascular leak syndrome a side effect of immunotherapy. *Immunopharmacology*.
Bentebibe, S.-E. (2019). A First-in-Human Study and Biomarker Analysis of NKTR-214, a Novel IL2Raf Biased Cytokine, in Patients with Advanced or Metastatic Solid Tumors. *Cancer Discovery*.
Buchbinder, E. I. (2019). Therapy with high-dose Interleukin-2 (HD IL-2) in metastatic melanoma and renal cell carcinoma following PD1 or PDL1 inhibition. *Journal of Immunotherapy for Cancer*.
Chan, I. H. (2015). The Potentiation of IFNg and Induction of Cytotoxic Proteins by Pegylated IL-10 in Human CD8 T cells. *Journal of Interferon and Cytokine Research*.
Chen, X. (2018). A novel human IL-2 mutein with minimal systemic toxicity exerts greater antitumor efficacy than wild-type IL-2. *Cell Death and Disease*.
Chinen, T. (2016). An essential role for IL-2 receptor in regulatory T cell function. *Nature Immunology*.
Davis, I. D. (2009). A Phase I and Pharmacokinetic Study of Subcutaneously-Administered Recombinant Human Interleukin-4 (rhuIL-4) in Patients with Advanced Cancer. *Growth Factors*.
Emmerich, J. (2012). IL-10 Directly Activates and Expands Tumor-Resident CD80 T Cells without DeNovo Infiltration from Secondary Lymphoid Organs. *Cancer Research*, 3570-3581.
Fedorak, R. (2000). Recombinant Human Interlekin 10 in the Treatment of Patients with Mild to Moderately Active Crohn's Disease. *Gastroenterology*, 1473-1482.
Gooch, J. L. (1998). Interleukin 4 Inhibits Growth and Induces Apoptosis in Human Breast Cancer Cells. *Cancer Research*.
Greve, J. M. (2000). U.S. Pat. No. 6,028,176.
Groux, H. (1998). Inhibitory and Stimulatory Effects of IL-10 on Human CD8+ T cells. *The Journal of Immunology*.
Guan, H. (2007). Blockade of Hyaluronan Inhibits IL-2 Induced Vascular Leak Syndrome and Maintains Effectiveness of IL-2 Treatment in Metastatic Melanoma. *Journal of Immunology*.
Hart, P. H. (1989). Potential antiinflammatory effects of interleukin 4: Suppression of human monocyte tumor necrosis factor ca, interleukin 1, and prostaglandin E2. *PNAS*.
Hart, P. H. (1991). IL-4 suppresses IL-1, TNF-a and PGE2 production by human peritoneal macrophages. *Immunology*.
Jiang, T. (2016). Role of IL-2 in cancer immunotherapy. *Oncoimmunology*.
Kirchner, G. I. (1998). Pharmacokinetics of human Interleukin-2 in advanced renal cell carcinoma patients following subcutaneous application. *British Journal Clinical Pharmacology*.
Lee, H. L. (2016). Tumor growth suppressive effect of IL-4 through p21-mediated activation of STAT6 in IL-4Rα overexpressed melanoma models. *Oncotarget*.
Li, R. (2013). Expression of recombinant human IL-4 in *Pichia pastoris* and relationship between its glycosylation and biological function. *Protein Expression and Purification*.
Malefyt, R. d. (1991). Interleukin 10 inhibits cytokine synthesis by human monocytes: An autoreglatory role of IL-10 produced by monocytes. *JEM*.
Malefyt, R. d. (1991). Interleukin 10 Inhibits Cytokine Synthesis by Human Monocytes An Autoregulatory Role of IL-10 Produced by Monocytes. *Journal of Experimental Medicine*, 1209-1220.
McGuirk, P. (2000). A Regulatory Role for Interleukin 4 in Differential Inflammatory Responses in the Lung following Infection of Mice Primed with Th1- or Th2-Inducing Pertussis Vaccines. *Infection and Immunity*.
Moore, K. W. (2001). Interleukin 10 and the Interleukin 10 Receptor. *Annual Reviews Immunology*.
Mumm, J. (2011). IL-10 induces IFNg-Mediated Tumor Immunity. *Cancer Cell*.
Mumm, J. B. (2011). IL-10 Elicits IFNg-Dependent Tumor Immune Surveillance. *Cancer Cell*.
Naing, A. (2016). Safety, Antitumor Activity, and Immune Activation of Pegylated Recombinant Human Interleukin-10 (AM0010) in Patients With Advanced Solid Tumors. *Journal of Clinical Oncology*.

Naing, A. (2018). PEGylated IL-10 (Pegilodecakin) Induces Systemic Immune Activation, CD8+ T cell Invigoration and Polyclonal T cell Expansion in Cancer Patients. *Cancer Cell*.

Ryan, J. J. (1997). Interleukin-4 and its receptor: Essential mediators of the allergic response. *The Journal of Allergy and Clinical Immunology*.

Schreiber, S. (2000). Safety and Efficacy of Recombinant Human Interleukin 10 in Chronic Active Crohn's Disease. *Gastroenterology*, 1461-1472.

Scott, M. J. (2006). Interleukin-10 suppresses natural killer cell but not natural killer T cell activation during bacterial infection. *Cytokine*.

Sivakumar, P. V. (2013). Comparison of Vascular Leak Syndrome in Mice Treated with IL21 or IL2. *Comparative Medicine*.

Spigel, D. R. (2020). Randomized phase II study of pembrolizumab (P) alone versus pegilodecakin (PEG) in combination with P as first-line (1 L) therapy in patients (pts) with stage IV non-small cell lung cancer (NSCLC) with high PD-L1 expression (CYPRESS 1). *ASCO*, (p. 9563).

Steinke, J. W. (2001). Th2 cytokines and asthma Interleukin-4: its role in the pathogenesis of asthma, and targeting it for asthma treatment with interleukin-4 receptor antagonists. *Respiratory Research*.

Varin, A. (2010). Alternative activation of macrophages by IL-4 impairs phagocytosis of pathogens but potentiates microbial-induced signalling and cytokine secretion. *Blood*.

Woodward, E. A. (2012). The anti-inflammatory actions of IL-4 in human monocytes are not mediated by IL-10, RP105 or the kinase activity of RIPK2. *Cytokine*.

The invention claimed is:

1. A dual cytokine fusion protein of formula (I)

$$NH_2\text{-(IL-10)-}(X^1)\text{-}(Z_n)\text{-}(X^2)\text{-(IL-10)-COOH} \quad \text{(Formula I)};$$

wherein
"IL-10" is a monomer;
"$X^1$" is a VL or VH region from a first monoclonal antibody;
"$X^2$" is a VH or VL region from the first monoclonal antibody;
wherein when $X^1$ is a VL, $X^2$ is a VH or when $X^1$ is a VH, $X^2$ is a VL;
wherein the first monoclonal antibody is an anti-Ebola antibody;
wherein the VL and VH from the anti-Ebola antibody include 3 light chain CDRs and 3 heavy chain CDRs that are engrafted with 3 light chain CDRs and 3 heavy chain CDRs from a second monoclonal antibody;
"Z" is a cytokine other than IL-10;
"n" is an integer of 1; and
wherein the IL-10 is SEQ ID No: 1, the second antibody is an anti-VEGFR2 monoclonal antibody, and Z is IL-2.

2. The fusion protein according to claim 1, wherein the VH and VL regions comprise a framework region obtained from a human anti-Ebola antibody.

3. The fusion protein according to claim 2, wherein the framework region from the anti-Ebola antibody is engrafted with the three VH CDRs and three VL CDRs from an anti-VEGF2 monoclonal antibody.

4. A pharmaceutical composition comprising the dual cytokine fusion protein according to claim 1, pharmaceutically acceptable buffers, and pharmaceutically acceptable excipients.

* * * * *

```
                           SEQUENCE LISTING

Sequence total quantity: 63
SEQ ID NO: 1            moltype = AA  length = 178
FEATURE                 Location/Qualifiers
REGION                  1..178
                        note = Human IL-10 Amino Acid Sequence
source                  1..178
                        mol_type = protein
                        organism = Homo sapiens
SEQUENCE: 1
MHSSALLCCL VLLTGVRASP GQGTQSENSC THFPGNLPNM LRDLRDAFSR VKTFFQMKDQ    60
LDNLLLKESL LEDFKGYLGC QALSEMIQFY LEEVMPQAEN QDPDIKAHVN SLGENLKTLR   120
LRLRRCHRFL PCENKSKAVE QVKNAFNKLQ EKGIYKAMSE FDIFINYIEA YMTMKIRN     178

SEQ ID NO: 2            moltype = DNA  length = 1629
FEATURE                 Location/Qualifiers
misc_feature            1..1629
                        note = Human IL-10 Nucleic Acid Sequence
source                  1..1629
                        mol_type = genomic DNA
                        organism = Homo sapiens
SEQUENCE: 2
acacatcagg ggcttgctct tgcaaaacca aaccacaaga cagacttgca aaagaaggca     60
tgcacagctc agcactgctc tgttgcctgg tcctcctgac tggggtgagg gccagcccag   120
gccagggcac ccagtctgag aacagctgca cccacttccc aggcaacctg cctaacatgc   180
ttcgagatct ccgagatgcc ttcagcagag tgaagacttt ctttcaaatg aaggatcagc   240
tggacaactt gttgttaaag gagtccttgc tggaggactt taagggttac ctgggttgcc   300
aagccttgtc tgagatgatc cagttttacc tggaggaggt gatgccccaa gctgagaacc   360
aagacccaga catcaaggcg catgtgaact ccctggggga gaacctgaag accctcaggc   420
tgaggctacg gcgctgtcat cgatttcttc cctgtgaaaa caagagcaag gcctgcaagg   480
aggtgaagaa tgcctttaat aagctccaag agaaaggcat ctacaaagcc atgagtgagt   540
ttgacatctt catcaactac atagaagcct acatgacaat gaagatacga aactgagaca   600
tcagggtggc gactctatag actctaggac ataaattaga ggtctccaaa atcggatctg   660
gggctctggg atagctgacc cagcccttg agaaacctta ttgtacctct cttatagaat    720
atttattacc tctgatacct caaccccat ttctatttat ttactgagct tctctgtgaa    780
cgatttagaa agaagcccaa tattataatt tttttcaata tttattattt tcacctgttt   840
ttaagctgtt tccatagggt gacacactat ggtatttgag tgttttaaga taaattataa   900
gttacataag ggaggaaaaa aaatgttctt tggggagcca acagaagctt ccattccaag   960
cctgaccacg ctttctagct gttgagctgt tttccctgac ctccctctaa tttatcttgt  1020
ctctgggctt ggggcttcct aactgctaca aatactctta ggaagagaaa ccagggagcc  1080
cctttgatga ttaattcacc ttccagtgtc tcggagggat tcccctaacc tcattcccca  1140
accacttcat tcttgaaagc tgtggccagc ttgttattta taacaaccta aatttggttc  1200
taggccgggc gcggtggctc acgcctgtaa tcccagcact tgggaggct gaggcgggtg   1260
gatcacttga ggtcaggagt tcctaaccag cctggtcaac atggtgaaac cccgtctcta  1320
ctaaaaatac aaaaattagc cgggcatggt ggcgcgcacc tgtaatccca gctacttggg  1380
aggctgaggc aagagaattg cttgaaccca ggagatggaa gttgcagtga gctgatatca  1440
tgccccctgta ctccagcctg ggtgacagag caagactctg tctcaaaaaa taaaaataaa  1500
aataaatttg gttctaatag aactcagttt taactagaat ttattcaatt cctctgggaa  1560
tgttacattg tttgtctgtc ttcatagcag attttaattt tgaataaata aatgtatctt  1620
attcacatc                                                          1629

SEQ ID NO: 3            moltype = AA  length = 147
FEATURE                 Location/Qualifiers
REGION                  1..147
                        note = EBV IL-10 Amino Acid Sequence
source                  1..147
                        mol_type = protein
```

```
                        organism = Human gammaherpesvirus 4
SEQUENCE: 3
TDQCDNFPQM LRDLRDAFSR VKTFFQTKDE VDNLLLKESL LEDFKGYLGC QALSEMIQFY    60
LEEVMPQAEN QDPEAKDHVN SLGENLKTLR LRLRRCHRFL PCENKSKAVE QIKNAFNKLQ   120
EKGIYKAMSE FDIFINYIEA YMTIKAR                                      147

SEQ ID NO: 4            moltype = DNA  length = 632
FEATURE                 Location/Qualifiers
misc_feature            1..632
                        note = EBV IL-10 Nucleic Acid Sequence
source                  1..632
                        mol_type = genomic DNA
                        organism = Human gammaherpesvirus 4
SEQUENCE: 4
tataaatcac ttccctatct caggtaggcc tgcacacctt aggtatggag cgaaggttag    60
tggtcactct gcagtgcctg gtgctgcttt acctggcacc tgagtgtgga ggtacagacc   120
aatgtgacaa ttttccccaa atgttgaggg acctaagaga tgccttcagt cgtgttaaaa   180
cctttttcca gacaaaggac gaggtagata acctttgct caaggagtct ctgctagagg    240
actttaaggg ctaccttgga tgccaggcct gtcagaaat gatccaattc tacctaggag    300
aagtcatgcc acaggctgaa accaggacc ctgaagccaa agaccatgtc aattctttgg    360
gtgaaaatct aaagacccta cggctccgcc tgcgcaggtg ccacaggttc ctgccgtgtg   420
agaacaagag taaagcttgtg gaacagataa aaaatgcctt caacaagctg caggaaaaag   480
gaatttacaa agccatgagt gaatttgaca tttttattaa ctacatagaa gcatacatga    540
caattaaagc caggtgataa ttccataccc tggaagcagg agatgggtgc atttcacccc   600
aaccccccct ttcgactgtc atttacaata aa                                632

SEQ ID NO: 5            moltype = AA  length = 177
FEATURE                 Location/Qualifiers
REGION                  1..177
                        note = CMV IL-10 Amino Acid Sequence
source                  1..177
                        mol_type = protein
                        organism = Human betaherpesvirus 5
SEQUENCE: 5
MLSVMVSSSL VLIVFFLGAS EEAKPAATTT TIKNTKPQCR PEDYASRLQD LRVTFPHRVKP    60
TLQREDDYSV WLDGTVVKGC WGCSVMDWLL RRYLEIVFPA GDHVYPGLKT ELHSMRSTLE   120
SIYKDMRQCP LLGCGDKSVI SRLSQEAERK SDNGTRKGLS ELDTLFSRLE EYLHSRK      177

SEQ ID NO: 6            moltype = DNA  length = 693
FEATURE                 Location/Qualifiers
misc_feature            1..693
                        note = CMV IL-10 Nucleic Acid Sequence
source                  1..693
                        mol_type = genomic DNA
                        organism = Human betaherpesvirus 5
SEQUENCE: 6
atgctgtcgg tgatggtctc ttcctctctg gtcctgatcg tctttttct aggcgcttcc     60
gaggaggcga agccggcggc gacgacgacg acgataaaga atacaaagcc gcagtgtcgt   120
ccggaggatt acgcgagcag attgcaagat ctccgcgtca cctttcatcg agtaaaacct   180
acgttggtag tcatgtagg tacggtttat tgcgacggtc tttctttcc gcgtgtcggg    240
tgacgtagtt ttcctcttgt agcaacgtga ggacgactac tccgtgtgc tcgacgtac    300
ggtggtcaaa ggctgttggg gatgcagcgt catggactgg ttgttgaggc ggtatctgga   360
gatcgtgttc cccgcaggcg accacgtcta tcctggactt aagacggaat tgcatagtat   420
gcgctcgacg ctagaatcca tctacaaaga catgcggcaa tgcgtaagtg tctctgtggc   480
ggcgctgtcc gcgcagaggt aacaacgtgt tcatagcacg ctgttttact tttgtcgggc   540
tcccagcctc tgttaggttg cggagataag tccgtgatta gtcggctgtc tcaggaggcg   600
gaaaggaaat cggataacgg cacgcggaaa ggtctcagcg agttggacac gttgtttagc   660
cgtctcgaag agtatctgca ctcgagaaag tag                               693

SEQ ID NO: 7            moltype = AA  length = 178
FEATURE                 Location/Qualifiers
REGION                  1..178
                        note = Mouse IL-10 Amino Acid Sequence
source                  1..178
                        mol_type = protein
                        organism = Mus musculus
SEQUENCE: 7
MPGSALLCCL LLLTGMRISR GQYSREDNNC THFPVGQSHM LLELRTAFSQ VKTFFQTKDQ    60
LDNILLTDSL MQDFKGYLGC QALSEMIQFY LVEVMPQAEK HGPEIKEHLN SLGEKLKTLR   120
MRLRRCHRFL PCENKSKAVE QVKSDFNKLQ DQGVYKAMNE FDIFINCIEA YMMIKMKS    178

SEQ ID NO: 8            moltype = DNA  length = 1314
FEATURE                 Location/Qualifiers
misc_feature            1..1314
                        note = Mouse IL-10 Nucleic Acid Sequence
source                  1..1314
                        mol_type = genomic DNA
                        organism = Mus musculus
SEQUENCE: 8
```

```
ggggggggggg atttagagac ttgctcttgc actaccaaag ccacaaagca gccttgcaga    60
aaagagagct ccatcatgcc tggctcagca ctgctatgct gcctgctctt actgactggc   120
atgaggatca gcaggggcca gtacagccgg aagacaata actgcaccca cttcccagtc   180
ggccagagcc acatgctcct agagctgcgg actgccttca gccaggtgaa gactttcttt   240
caaacaaagg accagctgga caacatactg ctaaccgact ccttaatgca ggactttaag   300
ggttacttgg gttgccaagc cttatcggaa atgatccagt tttacctggt agaagtgatg   360
ccccaggcag agaagcatgg cccagaaatc aaggagcatt tgaattccct gggtgagaag   420
ctgaagaccc tcaggatgcg gctgaggcgc tgtcatcgat ttctccctg tgaaaataag    480
agcaaggcag tggagcaggt gaagagtgat tttaataagc tccaagacca aggtgtctaa   540
aaggccatga atgaatttga catcttcatc aactgcatag aagcatacat gatgatcaaa   600
atgaaaagct aaaacacctg cagtgtgtat tgagtctgct ggactccagg acctagacag   660
agctctctaa atctgatcca gggatcttag ctaacggaaa caactccttg aaaacctcg    720
tttgtacctc tctccgaaat atttattacc tctgatcct cagttcccat tctatttatt    780
cactgagctt ctctgtgaac tatttagaaa gaagcccaat attataattt tacagtattt   840
attattttta acctgtgttt aagctgtttc cattggggac actttatagt atttaaaggg   900
agattatatt atatgatggg aggggttctt ccttgggaag caattgaagc ttctattcta   960
aggctggcca cacttgagag ctgcagggcc ctttgctatg tgtccttc aattgctctc    1020
atccctgagt tcagagctcc taagagagtt gtgaagaaac tcatgggtct tgggaagaa   1080
aaccagggag atcctttgat gatcattcct gcagcagctc agagggttcc cctactgtca   1140
tcccccagcc gcttcatccc tgaaaactgt ggccagtttg ttatttataa ccacctaaaa   1200
ttagttctaa tagaactcat ttttaactag aagtaatgca attcctctgg gaatggtgta   1260
ttgtttgtct gcctttgtag cagcatctaa ttttgaataa atggatctta ttcg         1314

SEQ ID NO: 9           moltype = AA   length = 170
FEATURE                Location/Qualifiers
REGION                 1..170
                       note = Artificial Sequence DVLP5
source                 1..170
                       mol_type = protein
                       organism = synthetic construct
SEQUENCE: 9
MDMRVPAQLL GLLLLWLRGA RCGTDQCDNF PQMLRDLRDA FSRVKTFFQT KDELDNLLLK    60
ESLLEDFKGY LGCQALSEMI QFYLEEVMPQ AENQDPEAKD HVNSLGENLK TLRLRLRRCH   120
RFLPCENKSK AVEQIKNAFN KLQEKGIYKA MSEFDIFINY IEAYMTIKAR              170

SEQ ID NO: 10          moltype = AA   length = 170
FEATURE                Location/Qualifiers
REGION                 1..170
                       note = Artificial Sequence DVLP6
source                 1..170
                       mol_type = protein
                       organism = synthetic construct
SEQUENCE: 10
MDMRVPAQLL GLLLLWLRGA RCGTDQCDNF PQMLRDLRDA FSRVKTFFQT KDEVDNLLLK    60
ESLLEDFKGY LGCQALSEMI QFYLEEVMPQ AENQDPEIKD HVNSLGENLK TLRLRLRRCH   120
RFLPCENKSK AVEQIKNAFN KLQEKGIYKA MSEFDIFINY IEAYMTIKAR              170

SEQ ID NO: 11          moltype = AA   length = 170
FEATURE                Location/Qualifiers
REGION                 1..170
                       note = Artificial Sequence DVLP7
source                 1..170
                       mol_type = protein
                       organism = synthetic construct
SEQUENCE: 11
MDMRVPAQLL GLLLLWLRGA RCGTDQCDNF PQMLRDLRDA FSRVKTFFQT KDELDNLLLK    60
ESLLEDFKGY LGCQALSEMI QFYLEEVMPQ AENQDPEIKD HVNSLGENLK TLRLRLRRCH   120
RFLPCENKSK AVEQIKNAFN KLQEKGIYKA MSEFDIFINY IEAYMTIKAR              170

SEQ ID NO: 12          moltype = AA   length = 147
FEATURE                Location/Qualifiers
REGION                 1..147
                       note = DV05 Amino Acid Sequence
source                 1..147
                       mol_type = protein
                       organism = synthetic construct
SEQUENCE: 12
TDQCDNFPQM LRDLRDAFSR VKTFFQTKDE LDNLLLKESL LEDFKGYLGC QALSEMIQFY    60
LEEVMPQAEN QDPEAKDHVN SLGENLKTLR LRRCHRFL PCENKSKAVE QIKNAFNKLQ    120
EKGIYKAMSE FDIFINYIEA YMTIKAR                                       147

SEQ ID NO: 13          moltype = DNA   length = 441
FEATURE                Location/Qualifiers
misc_feature           1..441
                       note = DV05 Nucleic Acid Sequence
source                 1..441
                       mol_type = other DNA
                       organism = synthetic construct
variation              225
```

```
                        note = n=a, c, g, or t.
SEQUENCE: 13
accgaccagt gcgacaactt ccctcagatg ctgcgggacc tgagagatgc cttctccaga    60
gtgaaaacat tcttccagac caaggacgag ctggacaacc tgctgctgaa agagtccctg   120
ctggaagatt tcaagggcta cctgggctgt caggccctgt ccgagatgat ccagttctac   180
ctggaagaag tgatgcccca ggccgagaat caggaccccg aggcnaagga ccacgtgaac   240
tccctgggcg agaacctgaa aaccctgcgg ctgagactgc ggcggtgcca cagatttctg   300
ccctgcgaga caagtccaa ggcgtggaa cagatcaaga acgccttcaa caagctgcaa    360
gagaagggca tctacaaggc catgagcgag ttcgacatct tcatcaacta catcgaggcc   420
tacatgacca tcaaggccag a                                             441

SEQ ID NO: 14            moltype = AA  length = 147
FEATURE                  Location/Qualifiers
REGION                   1..147
                         note = DV06 Amino Acid Sequence
source                   1..147
                         mol_type = protein
                         organism = synthetic construct
SEQUENCE: 14
TDQCDNFPQM LRDLRDAFSR VKTFFQTKDE VDNLLLKESL LEDFKGYLGC QALSEMIQFY   60
LEEVMPQAEN QDPEIKDHVN SLGENLKTLR LRLRRCHRFL PCENKSKAVE QIKNAFNKLQ  120
EKGIYKAMSE FDIFINYIEA YMTIKAR                                      147

SEQ ID NO: 15            moltype = DNA  length = 441
FEATURE                  Location/Qualifiers
misc_feature             1..441
                         note = DV06 Nucleic Acid Sequence
source                   1..441
                         mol_type = other DNA
                         organism = synthetic construct
variation                93
                         note = n=a, c, g, or t.
SEQUENCE: 15
accgaccagt gcgacaactt ccctcagatg ctgcgggacc tgagagatgc cttctccaga    60
gtgaaaacat tcttccagac caaggacgag gtngacaacc tgctgctgaa agagtccctg   120
ctggaagatt tcaagggcta cctgggctgt caggccctgt ccgagatgat ccagttctac   180
ctggaagaag tgatgcccca ggccgagaat caggaccccg agatcaagga ccacgtgaac   240
tccctgggcg agaacctgaa aaccctgcgg ctgagactgc ggcggtgcca cagatttctg   300
ccctgcgaga caagtccaa ggcgtggaa cagatcaaga acgccttcaa caagctgcaa    360
gagaagggca tctacaaggc catgagcgag ttcgacatct tcatcaacta catcgaggcc   420
tacatgacca tcaaggccag a                                             441

SEQ ID NO: 16            moltype = AA  length = 147
FEATURE                  Location/Qualifiers
REGION                   1..147
                         note = DV07 Amino Acid Sequence
source                   1..147
                         mol_type = protein
                         organism = synthetic construct
SEQUENCE: 16
TDQCDNFPQM LRDLRDAFSR VKTFFQTKDE LDNLLLKESL LEDFKGYLGC QALSEMIQFY   60
LEEVMPQAEN QDPEIKDHVN SLGENLKTLR LRLRRCHRFL PCENKSKAVE QIKNAFNKLQ  120
EKGIYKAMSE FDIFINYIEA YMTIKAR                                      147

SEQ ID NO: 17            moltype = DNA  length = 441
FEATURE                  Location/Qualifiers
misc_feature             1..441
                         note = DV07 Nucleic Acid Sequence
source                   1..441
                         mol_type = other DNA
                         organism = synthetic construct
SEQUENCE: 17
accgaccagt gcgacaactt ccctcagatg ctgcgggacc tgagagatgc cttctccaga    60
gtgaaaacat tcttccagac caaggacgag ctggacaacc tgctgctgaa agagtccctg   120
ctggaagatt tcaagggcta cctgggctgt caggccctgt ccgagatgat ccagttctac   180
ctggaagaag tgatgcccca ggccgagaat caggaccccg agatcaagga ccacgtgaac   240
tccctgggcg agaacctgaa aaccctgcgg ctgagactgc ggcggtgcca cagatttctg   300
ccctgcgaga caagtccaa ggcgtggaa cagatcaaga acgccttcaa caagctgcaa    360
gagaagggca tctacaaggc catgagcgag ttcgacatct tcatcaacta catcgaggcc   420
tacatgacca tcaaggccag a                                             441

SEQ ID NO: 18            moltype = AA  length = 567
FEATURE                  Location/Qualifiers
REGION                   1..567
                         note = DV07 Ebo
source                   1..567
                         mol_type = protein
                         organism = synthetic construct
SEQUENCE: 18
```

```
TDQCDNFPQM LRDLRDAFSR VKTFFQTKDE LDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLQQWG AGLLKPSETL   180
SLTCAVYGGS FTTTYWNWIR QPPGKGLEWI GEVNYSGNAN YNPSLKGRVA ISVDTSKNQF   240
SLRLNSVTAA DTAIYYCTSR IRSHIAYSWK GDVWGKGTTV TVGGGGSGGG GSGGGGSEIV   300
MTQSPGTLSL SPGERATLSC RASQSVPRNY IGWFQQKPGQ APRLLIYGAS SRAAGFPDRF   360
SGSGSGTDFT LTITRLEPED FAMYYCHQYD RLPYTFGQGT KLEIKGGGGS GGGGSGGGGS   420
TDQCDNFPQM LRDLRDAFSR VKTFFQTKDE LDNLLLKESL LEDFKGYLGC QALSEMIQFY   480
LEEVMPQAEN QDPEIKDHVN SLGENLKTLR LRLRRCHRFL PCENKSKAVE QIKNAFNKLQ   540
EKGIYKAMSE FDIFINYIEA YMTIKAR                                      567

SEQ ID NO: 19          moltype = AA  length = 561
FEATURE                Location/Qualifiers
REGION                 1..561
                       note = DV07 Ebo EGF
source                 1..561
                       mol_type = protein
                       organism = synthetic construct
SEQUENCE: 19
TDQCDNFPQM LRDLRDAFSR VKTFFQTKDE LDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLQQWG AGLLKPSETL   180
RLTCAVYGGS FTNYGVHWIR QPPGKGLEWI GVIWSGGNTD YNTPFTSRVT ISVDTSKNQF   240
SLQLNSVTAA DTAIYYCTSL TYYDYEFAWG KGTTVTVGGG GSGGGGSGGG GSEIVMTQSP   300
GTLSLSPGER ATLSCRASQS IGTNIHWFQQ KPGQAPRLLI YYASESISGF PDRFSGSGSG   360
TDFTLTITRL EPEDFAMYYC QQNNNWPTTF GQGTKLEIKG GGGSGGGGSG GGGSTDQCDN   420
FPQMLRDLRD AFSRVKTFFQ TKDELDNLLL KESLLEDFKG YLGCQALSEM IQFYLEEVMP   480
QAENQDPEIK DHVNSLGENL KTLRLRLRRC HRFLPCENKS KAVEQIKNAF NKLQEKGIYK   540
AMSEFDIFIN YIEAYMTIKA R                                            561

SEQ ID NO: 20          moltype = AA  length = 581
FEATURE                Location/Qualifiers
REGION                 1..581
                       note = DV06 EboX
VARIANT                193..199
                       note = X can be any amino acid
REGION                 193..199
                       note = This region may encompass 3-7 residues
VARIANT                214..231
                       note = X can be any amino acid
REGION                 214..231
                       note = This region may encompass 14-18 residues
VARIANT                264..274
                       note = X can be any amino acid
REGION                 264..274
                       note = This region may encompass 7-11 residues
VARIANT                329..342
                       note = X can be any amino acid
REGION                 329..342
                       note = This region may encompass 9-14 residues
VARIANT                358..366
                       note = X can be any amino acid
REGION                 358..366
                       note = This region may encompass 5-9 residues
VARIANT                399..409
                       note = X can be any amino acid
REGION                 399..409
                       note = This region may encompass 7-11 residues
REGION                 1..581
                       note = See specification as filed for detailed description
                        of substitutions and preferred embodiments
source                 1..581
                       mol_type = protein
                       organism = synthetic construct
SEQUENCE: 20
TDQCDNFPQM LRDLRDAFSR VKTFFQTKDE VDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLQQWG AGLLKPSETL   180
SLTCAVYGGS FTXXXXXXXW IRQPPGKGLE WIGXXXXXXX XXXXXXXXXX XRVAISVDTS   240
KNQFSLRLNS VTAADTAIYY CTSXXXXXXX XXXXWKGDVW GKGTTVTVSS GGGGSGGGGS   300
GGGGSEIVMT QSPGTLSLSP GERATLSCXX XXXXXXXXXX XXWFQQKPGQ APRLLIYXXX   360
XXXXXXGFPD RFSGSGSGTD FTLTITRLEP EDFAMYYCXX XXXXXXXXXF GQGTKLEIKG   420
GGGSGGGGSG GGGSTDQCDN FPQMLRDLRD AFSRVKTFFQ TKDEVDNLLL KESLLEDFKG   480
YLGCQALSEM IQFYLEEVMP QAENQDPEIK DHVNSLGENL KTLRLRLRRC HRFLPCENKS   540
KAVEQIKNAF NKLQEKGIYK AMSEFDIFIN YIEAYMTIKA R                      581

SEQ ID NO: 21          moltype = AA  length = 569
FEATURE                Location/Qualifiers
REGION                 1..569
```

```
                        note = DV06 Ebo
source                  1..569
                        mol_type = protein
                        organism = synthetic construct
SEQUENCE: 21
TDQCDNFPQM LRDLRDAFSR VKTFFQTKDE VDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLQQWG AGLLKPSETL   180
SLTCAVYGGS FTTTYWNWIR QPPGKGLEWI GEVNYSGNAN YNPSLKGRVA ISVDTSKNQF   240
SLRLNSVTAA DTAIYYCTSR IRSHIAYSWK GDVWGKGTTV TVSSGGGGSG GGGSGGGGSE   300
IVMTQSPGTL SLSPGERATL SCRASQSVPR NYIGWFQQKP GQAPRLLIYG ASSRAAGFPD   360
RFSGSGSGTD FTLTITRLEP EDFAMYYCHQ YDRLPYTFGQ GTKLEIKGGG GSGGGGSGGG   420
GSTDQCDNFP QMLRDLRDAF SRVKTFFQTK DEVDNLLLKE SLLEDFKGYL GCQALSEMIQ   480
FYLEEVMPQA ENQDPEIKDH VNSLGENLKT LRLRRCHR FLPCENKSKA VEQIKNAFNK    540
LQEKGIYKAM SEFDIFINYI EAYMTIKAR                                    569

SEQ ID NO: 22           moltype = AA  length = 575
FEATURE                 Location/Qualifiers
REGION                  1..575
                        note = DV06 MadCam
source                  1..575
                        mol_type = protein
                        organism = synthetic construct
SEQUENCE: 22
TDQCDNFPQM LRDLRDAFSR VKTFFQTKDE VDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLVQSG AEVKKPGASV   180
KVSCKASGYT FTSYGINWVR QAPGQGLEWM GWISVYSGNT NYAQKVQGRV TMTADTSTST   240
AYMDLRSLRS DDTAVYYCAR EGSSSSGDYY YGMDVWGQGT TVTVSSGGGG SGGGGSGGGG   300
SDIVMTQTPL SLSVTPGQPA SISCKSSQSL LHTDGTTYLY WYLQKPGQPP QLLIYEVSNR   360
FSGVPDRFSG SGSGTDFTLK ISRVEAEDVG IYYCMQNIQL PWTFGQGTKV EIKGGGGSGG   420
GGSGGGGSTD QCDNFPQMLR DLRDAFSRVK TFFQTKDEVD NLLLKESLLE DFKGYLGCQA   480
LSEMIQFYLE EVMPQAENQD PEIKDHVNSL GENLKTLRLR LRRCHRFLPC ENKSKAVEQI   540
KNAFNKLQEK GIYKAMSEFD IFINYIEAYM TIKAR                              575

SEQ ID NO: 23           moltype = AA  length = 573
FEATURE                 Location/Qualifiers
REGION                  1..573
                        note = DV07 EboX
VARIANT                 193..199
                        note = X can be any amino acid
REGION                  193..199
                        note = This region may encompass 3-7 residues
VARIANT                 213..230
                        note = X can be any amino acid
REGION                  213..230
                        note = This region may encompass 14-18 residues
VARIANT                 263..273
                        note = X can be any amino acid
REGION                  263..273
                        note = This region may encompass 7-11 residues
VARIANT                 321..334
                        note = X can be any amino acid
REGION                  321..334
                        note = This region may encompass 9-14 residues
VARIANT                 350..358
                        note = X can be any amino acid
REGION                  350..358
                        note = This region may encompass 5-9 residues
VARIANT                 391..401
                        note = X can be any amino acid
REGION                  391..401
                        note = This region may encompass 7-11 residues
REGION                  1..573
                        note = See specification as filed for detailed description
                          of substitutions and preferred embodiments
source                  1..573
                        mol_type = protein
                        organism = synthetic construct
SEQUENCE: 23
TDQCDNFPQM LRDLRDAFSR VKTFFQTKDE LDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLQQWG AGLLKPSETL   180
RLTCAVYGGS FTXXXXXXXW IRQPPGKGLE WIXXXXXXXX XXXXXXXXXX RVTISVDTSK   240
NQFSLQLNSV TAADTAIYYC TSXXXXXXXX XXXWGKGTTV TVGGGGSGGG GSGGGGSEIV   300
MTQSPGTLSL SPGERATLSC XXXXXXXXXX XXXXWFQQKP GQAPRLLIYX XXXXXXXXGF   360
PDRFSGSGSG TDFTLTITRL EPEDFAMYYC XXXXXXXXXX XFGQGTKLEI KGGGGSGGGG   420
SGGGGSTDQC DNFPQMLRDL RDAFSRVKTF FQTKDELDNL LLKESLLEDF KGYLGCQALS   480
EMIQFYLEEV MPQAENQDPE IKDHVNSLGE NLKTLRLRLR RCHRFLPCEN KSKAVEQIKN   540
```

```
AFNKLQEKGI YKAMSEFDIF INYIEAYMTI KAR                               573

SEQ ID NO: 24           moltype = AA  length = 573
FEATURE                 Location/Qualifiers
REGION                  1..573
                        note = DV05 EboX
VARIANT                 193..199
                        note = X can be any amino acid
REGION                  193..199
                        note = This region may encompass 3-7 residues
VARIANT                 213..230
                        note = X can be any amino acid
REGION                  213..230
                        note = This region may encompass 14-18 residues
VARIANT                 263..273
                        note = X can be any amino acid
REGION                  263..273
                        note = This region may encompass 7-11 residues
VARIANT                 321..334
                        note = X can be any amino acid
REGION                  321..334
                        note = This region may encompass 9-14 residues
VARIANT                 350..358
                        note = X can be any amino acid
REGION                  350..358
                        note = This region may encompass 5-9 residues
VARIANT                 391..401
                        note = X can be any amino acid
REGION                  391..401
                        note = This region may encompass 7-11 residues
REGION                  1..573
                        note = See specification as filed for detailed description
                         of substitutions and preferred embodiments
source                  1..573
                        mol_type = protein
                        organism = synthetic construct
SEQUENCE: 24
TDQCDNFPQM LRDLRDAFSR VKTFFQTKDE LDNLLLKESL LEDFKGYLGC QALSEMIQFY   60
LEEVMPQAEN QDPEAKDHVN SLGENLKTLR LRLRRCHRFL PCENKSKAVE QIKNAFNKLQ  120
EKGIYKAMSE FDIFINYIEA YMTIKARGGG GSGGGGSGGG GSQVQLQQWG AGLLKPSETL  180
RLTCAVYGGS FTXXXXXXXW IRQPPGKGLE WIXXXXXXXX XXXXXXXXXX RVTISVDTSK  240
NQFSLQLNSV TAADTAIYYC TSXXXXXXXX XXXWGKGTTV TVGGGGSGGG GSGGGGSEIV  300
MTQSPGTLSL SPGERATLSC XXXXXXXXXX XXXXWFQQKP GQAPRLLIYX XXXXXXXXGF  360
PDRFSGSGSG TDFTLTITRL EPEDFAMYYC XXXXXXXXXX XFGQGTKLEI KGGGGSGGGG  420
SGGGGSTDQC DNFPQMLRDL RDAFSRVKTF FQTKDELDNL LLKESLLEDF KGYLGCQALS  480
EMIQFYLEEV MPQAENQDPE AKDHVNSLGE NLKTLRLRLR RCHRFLPCEN KSKAVEQIKN  540
AFNKLQEKGI YKAMSEFDIF INYIEAYMTI KAR                               573

SEQ ID NO: 25           moltype = AA  length = 569
FEATURE                 Location/Qualifiers
REGION                  1..569
                        note = DV07 EboL3
source                  1..569
                        mol_type = protein
                        organism = synthetic construct
SEQUENCE: 25
TDQCDNFPQM LRDLRDAFSR VKTFFQTKDE LDNLLLKESL LEDFKGYLGC QALSEMIQFY   60
LEEVMPQAEN QDPEIKDHVN SLGENLKTLR LRLRRCHRFL PCENKSKAVE QIKNAFNKLQ  120
EKGIYKAMSE FDIFINYIEA YMTIKARGGG GSGGGGSGGG GSQVQLQQWG AGLLKPSETL  180
SLTCAVYGGS FTTTYWNWIR QPPGKGLEWI GEVNYSGNAN YNPSLKGRVA ISVDTSKNQF  240
SLRLNSVTAA DTAIYYCTSR IRSHIAYSWK GDVWGKGTTV TVSSGGGGSG GGGSGGGGSE  300
IVMTQSPGTL SLSPGERATL SCRASQSVPR NYIGWFQQKP GQAPRLLIYG ASSRAAGFPD  360
RFSGSGSGTD FTLPITITRLEP EDFAMYYCHQ YDRLPYTFGQ GTKLEIKGGG GSGGGGSGG  420
GSTDQCDNFP QMLRDLRDAF SRVKTFFQTK DELDNLLLKE SLLEDFKGYL GCQALSEMIQ  480
FYLEEVMPQA ENQDPEIKDH VNSLGENLKT LRLRLRRCHR FLPCENKSKA VEQIKNAFNK  540
LQEKGIYKAM SEFDIFINYI EAYMTIKAR                                   569

SEQ ID NO: 26           moltype = AA  length = 563
FEATURE                 Location/Qualifiers
REGION                  1..563
                        note = DV07 EboEGFL3
source                  1..563
                        mol_type = protein
                        organism = synthetic construct
SEQUENCE: 26
TDQCDNFPQM LRDLRDAFSR VKTFFQTKDE LDNLLLKESL LEDFKGYLGC QALSEMIQFY   60
LEEVMPQAEN QDPEIKDHVN SLGENLKTLR LRLRRCHRFL PCENKSKAVE QIKNAFNKLQ  120
EKGIYKAMSE FDIFINYIEA YMTIKARGGG GSGGGGSGGG GSQVQLQQWG AGLLKPSETL  180
RLTCAVYGGS FTNYGVHWIR QPPGKGLEWI GVIWSGGNTD YNTPFTSRVT ISVDTSKNQF  240
```

```
SLQLNSVTAA DTAIYYCTSL TYYDYEFAWG KGTTVTVSSG GGGSGGGGSG GGGSEIVMTQ    300
SPGTLSLSPG ERATLSCRAS QSIGTNIHWF QQKPGQAPRL LIYYASESIS GFPDRFSGSG    360
SGTDFTLTIT RLEPEDFAMY YCQQNNNWPT TFGQGTKLEI KGGGGSGGGG SGGGGSTDQC    420
DNFPQMLRDL RDAFSRVKTF FQTKDELDNL LLKESLLEDF KGYLGCQALS EMIQFYLEEV    480
MPQAENQDPE IKDHVNSLGE NLKTLRLRLR RCHRFLPCEN KSKAVEQIKN AFNKLQEKGI    540
YKAMSEFDIF INYIEAYMTI KAR                                           563

SEQ ID NO: 27           moltype = AA  length = 565
FEATURE                 Location/Qualifiers
REGION                  1..565
                        note = DEboegfrDV07 Variant 1 Amino Acid Sequence
source                  1..565
                        mol_type = protein
                        organism = synthetic construct
SEQUENCE: 27
TDQCDNFPQM LRDLRDAFSR VKTFFQTKDE LDNLLLKESL LEDFKGYLGC QALSEMIQFY     60
LEEVMPQAEN QDPEIKDHVN SLGENLKTLR LRLRRCHRFL PCENKSKAVE QIKNAFNKLQ    120
EKGIYKAMSE FDIFINYIEA YMTIKARGGG GSGGGGSGGG GSQVQLQQWG AGLLKPSETL    180
SLTCAVSGFS LTNYGVNWIR QPPGKGLEWI GVIWSGGNTD YNPSLKGRVA ISVDTSKNQF    240
SLRLNSVTAA DTAIYYCARA LTYYDYEFAY WGKGTTVTVS SGGGGSGGGG SGGGGSEIVM    300
TQSPGTLSLS PGERATLSCR ASQSIGTNIG WFQQKPGQAP RLLIKYASER AAGFPDRFSG    360
SGSGTDFTLT ITRLEPEDFA MYYCQQNNNW PTTFGQGTKL EIKGGGGSGG SGGGGSSTD    420
QCDNFPQMLR DLRDAFSRVK TFFQTKDELD NLLLKESLLE DFKGYLGCQA LSEMIQFYLE    480
EVMPQAENQD PEIKDHVNSL GENLKTLRLR LRRCHRFLPC ENKSKAVEQI KNAFNKLQEK    540
GIYKAMSEFD IFINYIEAYM TIKAR                                         565

SEQ ID NO: 28           moltype = DNA  length = 1698
FEATURE                 Location/Qualifiers
misc_feature            1..1698
                        note = DEboegfrDV07 Variant 1 Nucleic Acid Sequence
source                  1..1698
                        mol_type = other DNA
                        organism = synthetic construct
SEQUENCE: 28
accgaccagt gcgacaactt ccctcagatg ctgcgggacc tgagagatgc cttctccaga     60
gtgaaaacat tcttccagac caaggacgag ctggacaacc tgctgctgaa agagtccctg    120
ctggaagatt tcaagggcta cctgggctgt caggccctgt ccgagatgat ccagttctac    180
ctggaagaag tgatgcccca ggccgagaat caggaccccg agatcaagga ccacgtgaac    240
tccctgggcg agaacctgaa aaccctgcgg ctgagactgc ggcggtgcca cagatttctg    300
ccctgcgaga acaagtccaa ggccgtggaa cagatcaaga acgccttcaa caagctgcaa    360
gagaagggca tctacaaggc catgagcgag ttcgacatct tcatcaacta catcgaggcc    420
tacatgacca tcaaggccag aggcggcgga ggatctggcg gaggtggaag cggaggcggt    480
ggatctcagg ttcagttgca gcaatggggc gctggcctgc tgaagcctct tgagacactg    540
tctctgacct gcgccgtgtc cggcttctct ctgaccaatt acggcgtgaa ctggattcgg    600
cagcctcctg gcaagggcct ggaatggatc ggagtgattt ggagcggcgg caacaccgac    660
tacaaccccA gtctgaaggg cagagtggcc atctccgtgg acacctccaa gaaccagttc    720
tccctgagac tgaactccgt gaccgccgct gataccgcca tctactactg tgctagagcc    780
ctgacctact acgactacga gttcgcctat ggggcaaggg gcaccaccgt gactgttagt    840
agtggtggtg gcggtagtgg cggaggcggt tcaggcggtg gtggatctga atcgtgatg    900
acccagtctc ctggcactct gtctctgtct ccgcggagaa gagctaccct gtcttgtaga    960
gcctctcagt ccatcggcac caacatcggc tggttccagc agaagcctgg acaggctccc   1020
cggctgctga ttaagtacgc ctctgagaga gccgctggct tccctgacag attctccggc   1080
tctggctctg gcaccgactt caccctgacc atcaccagac tggaacccga ggacttcgct   1140
atgtactact gccagcagaa caacaactgg cccaccacct ttggccaggg caccaagctg   1200
gaaatcaaag tgtgcggtgg ttcaggtggc ggaggaaggc gcgaaggcgg atctacagat   1260
cagtgtgaca ttttccccca aatgctgagg gatctgcggg acgccttcag ccgggtcaag   1320
acatttttc agacaaagga tgaactcgat aaactcttgc tcaaagagag cctgctcgag   1380
gactttaagg gatatctggg atgccaggct ctgagcgaaa tgattcagtt ttatctcgag   1440
gaagtcatgc ctcaagcaga gaaccaggat ccagagatta aggatcatgt gaatagcctc   1500
ggggagaacc tcaagacact gagactccgg ctgagaagat gccaccggtt tctgccttgt   1560
gaaaacaaaa gcaaggctgt cgagcagatt aagaatgctt ttaacaaact ccaagaaaaa   1620
gggatctata aggctatgtc tgagtttgat atctttatca attatatcga agcttatatg   1680
actattaagg cccggtag                                                1698

SEQ ID NO: 29           moltype = AA  length = 565
FEATURE                 Location/Qualifiers
REGION                  1..565
                        note = DEboegfrDV07 Variant 2 Amino Acid Sequence
source                  1..565
                        mol_type = protein
                        organism = synthetic construct
SEQUENCE: 29
TDQCDNFPQM LRDLRDAFSR VKTFFQTKDE LDNLLLKESL LEDFKGYLGC QALSEMIQFY     60
LEEVMPQAEN QDPEIKDHVN SLGENLKTLR LRLRRCHRFL PCENKSKAVE QIKNAFNKLQ    120
EKGIYKAMSE FDIFINYIEA YMTIKARGGG GSGGGGSGGG GSQVQLQQWG AGLLKPSETL    180
SLTCAVSGFS LTNYGVHWIR QPPGKGLEWI GVIWSGGNTD YNPFTSRVA ISVDTSKNQF     240
SLRLNSVTAA DTAIYYCTSA LTYYDYEFAY WGKGTTVTVS SGGGGSGGGG SGGGGSEIVM    300
TQSPGTLSLS PGERATLSCR ASQSIGTNIH WFQQKPGQAP RLLIYYASES ISGFPDRFSG    360
SGSGTDFTLT ITRLEPEDFA MYYCQQNNNW PTTFGQGTKL EIKGGGGSGG GGSGGGGSTD    420
```

```
QCDNFPQMLR DLRDAFSRVK TFFQTKDELD NLLLKESLLE DFKGYLGCQA LSEMIQFYLE  480
EVMPQAENQD PEIKDHVNSL GENLKTLRLR LRRCHRFLPC ENKSKAVEQI KNAFNKLQEK  540
GIYKAMSEFD IFINYIEAYM TIKAR                                       565

SEQ ID NO: 30            moltype = DNA   length = 1770
FEATURE                  Location/Qualifiers
misc_feature             1..1770
                         note = DEboegfrDV07 Variant 2 Nucleic Acid Sequence
source                   1..1770
                         mol_type = other DNA
                         organism = synthetic construct
SEQUENCE: 30
gctagcgccg ccaccatggg atggtctttg atcctgctgt tcctggtggc cgtggctacc   60
agagtgcatt ctaccgacca gtgcgacaac ttccctcaga tgctgcggga cctgagagat  120
gccttctcca gagtgaaaac attcttccag accaaggacg agctggacaa cctgctgctg  180
aaagagtccc tgctggaaga tttcaagggc tacctgggct gtcaggccct gtccgagatg  240
atccagttct acctggaaga agtgatgccc caggccgaga tcaggaccc cgagatcaag  300
gaccacgtga actccctggg cgagaacctg aaaaccctgc ggctgagact gcggcggtgc  360
cacagatttc tgccctgcga gaacaagtcc aaggccgtgg aacagatcaa gaacgccttc  420
aacaagctgc aagagaaggg catctacaag gccatgagcg agttcgacat cttcatcaac  480
tacatcgagg cctacatgac catcaaggcc agaggcggcg gaggatctgg cggaggtgga  540
agcggaggcg gtggatctca ggttcagttg cagcaatggg gcgctggcct gctgaagcct  600
tctgagacac tgtctctgac ctgcgccgtg tacggcttct ccctgaccaa ttatggcgtg  660
cactggatca gacagcctcc aggcaaaggc ctgaatgga tcggagtgat ttggagcggc  720
ggcaacaccg actacaacac cccttttacc tctagagtgg ccatctccgt ggacacctcc  780
aagaacccag tcagcctgag actgaactcc gtgaccgccg ctgataccgc catctactac  840
tgcacctccg ctctgaccta ctacgactac gagttcgcct actggggcaa gggcaccaca  900
gtgactgtta gtagtggtgg cggaggtagc ggtggtggtg gtagtggcgg tggcggatct  960
gagatcgtga tgacccaatc tcctggcact ctgtctctgt ctcccggcga gagagctacc 1020
ctgtcttgta gagcctctca gtccatcggc accaacatcc actggttcca gcagaagcct 1080
ggacaggccc ctagactgct gatctactac gcctccgaga gcatcagcgg cttccctgac 1140
agattctccg gctctggctc tggcaccgac ttcaccctga caatcaccg gctggaacct 1200
gaggacttcg ctatgtacta ctgccagcag aacaacaact ggcccaccac ctttggccag 1260
ggcaccaagc tggaaatcaa aggcggaggc ggcagtggcg gcggtggctc cggcggaggc 1320
ggatctacag atcagtgtga caatttttccc caaatgctga gggatctgcg ggacgcctcg 1380
agccgggtca agacattttt tcagacaaag gatgaactcg ataacctctt gctcaaagag 1440
agcctgctcg aggacttcaa aggatatctg ggatgccagg ctctgagcga aatgattcag 1500
tttttatctcg aggaagtcat gccacaagca gagaaccagg atccagagat taaggatcat 1560
gtgaatagcc tcggggagaa cctcaagaca ctgagactcc ggctacagac atgccaccgg 1620
tttctgcctt gtgaaaacaa aagcaaggct gtcgagcaga ttaagaatgc ttttaacaaa 1680
ctccaagaaa aagggatcta taaggctatg tctgagtttg atatctttat caattatatc 1740
gaagcttata tgactattaa ggcccggtag                                  1770

SEQ ID NO: 31            moltype = AA   length = 565
FEATURE                  Location/Qualifiers
REGION                   1..565
                         note = DEboegfrDV07 Variant 3 (SLP) Amino Acid Sequence
source                   1..565
                         mol_type = protein
                         organism = synthetic construct
SEQUENCE: 31
TDQCDNFPQM LRDLRDAFSR VKTFFQTKDE LDNLLLKESL LEDFKGYLGC QALSEMIQFY   60
LEEVMPQAEN QDPEIKDHVN SLGENLKTLR LRLRRCHRFL PCENKSKAVE QIKNAFNKLQ  120
EKGIYKAMSE FDIFINYIEA YMTIKARGGG GSGGGGSGGG GSQVQLQQWG AGLLKPSETL  180
SLTCAVYGFS LTNYGVHWIR QPPGKGLEWL GVIWSGGNTD YNTPFTSRVA ISKDNSKNQV  240
SLRLNSVTAA DTAIYYCARA LTYYDYEFAY WGKGTTVTVS SGGGGSGGGG SGGGGSEIVL  300
TQSPGTLSLS PGERATLSCR ASQSIGTNIH WYQQKPGQAP RLLIKYASES ISGFPDRFSG  360
SGSGTDFTLT ITRLEPEDFA MYYCQQNNNW PTTFGQGTKL EIKGGGGSGG GGSGGGGSTD  420
QCDNFPQMLR DLRDAFSRVK TFFQTKDELD NLLLKESLLE DFKGYLGCQA LSEMIQFYLE  480
EVMPQAENQD PEIKDHVNSL GENLKTLRLR LRRCHRFLPC ENKSKAVEQI KNAFNKLQEK  540
GIYKAMSEFD IFINYIEAYM TIKAR                                       565

SEQ ID NO: 32            moltype = DNA   length = 1698
FEATURE                  Location/Qualifiers
misc_feature             1..1698
                         note = DEboegfrDV07 Variant 3 (SLP) Nucleic Acid Sequence
source                   1..1698
                         mol_type = other DNA
                         organism = synthetic construct
SEQUENCE: 32
accgaccagt gcgacaactt ccctcagatg ctgcgggacc tgagagatgc cttctccaga   60
gtgaaaacat tcttccagac caaggacgag ctggacaacc tgctgctgaa agagtccctg  120
ctggaagatt tcaagggcta cctgggctgt caggccctgt ccgagatgat ccagttctac  180
ctggaagaag tgatgcccca ggccgagaat caggaccccg agatcaagga ccacgtgaac  240
tccctgggcg agaacctgaa aaccctgcgg ctgagactgc ggcggtgcca cagatttctg  300
ccctgcgaga acaagtccaa ggccgtggaa cagatcaaga acgccttcaa caagctgcaa  360
gagaagggca tctacaaggc catgagcgag ttcgacatct tcatcaacta catcgaggcc  420
tacatgacca tcaaggccag aggcggcgga ggatctggcg gaggtggaag cggaggcggt  480
ggatctcagg ttcagttgca gcaatggggc gctggcctgc tgaagccttc tgagacactg  540
```

```
tctctgacct gcgccgtgta cggcttctcc ctgaccaatt atggcgtgca ctggatcaga    600
cagcctccag gcaaaggcct ggaatggctg ggagtgattt ggagcggcgg caacaccgac    660
tacaacaccc ctttcacctc tagagtggcc atctccaagg acaactccaa gaaccaggtg    720
tccctgagac tgaactccgt gaccgctgcc gataccgcca tctactactg tgctagagcc    780
ctgacctact acgactacga gttcgcctat tggggcaagg caccaccgt gactgttagt    840
agtggtggtg gcggtagtgg cggaggcggc tcaggcggtg gtggatctga aattgtgctg    900
acccagtctc ctggcactct gtctttgagc cctggcgaga gagctaccct gtcctgtaga    960
gcctctcagt ccatcggcac caacatccac tggtatcagc agaagcctgg acaggcccct   1020
cggctgctga ttaagtacgc ctccgagtcc atcagcggct ccctgacag attctccggc   1080
tctggctctg gcaccgactt caccctgaca atcacccggc tggaacctga ggacttcgct   1140
atgtactact gccagcagaa caacaactgg cccaccacct ttggccaggg caccaagctg   1200
gaaatcaaag gtggcggtgg ttcaggtggc ggaggaagcg gcggaggcgg atctacagat   1260
cagtgtgaca atttccccca aatgctgagg gatctgcggg acgccttcag ccgggtcaag   1320
acatttttttc agacaaagga tgaactcgat aacctcttgc tcaaagagag cctgctcgag   1380
gacttcaaag gatatctggg atgccaggct ctgagcgaaa tgattcagtt ttatctcgag   1440
gaagtcatgc ctcaagcaga gaaccaggat ccagagatta aggatcatgt gaatagcctc   1500
ggggagaacc tcaagacact gagactccgg ctgagaagat gccaccggtt tctgccttgt   1560
gaaaacaaaa gcaaggctgt cgagcagatt aagaatgctt taacaaatt gcaagaaaaa   1620
gggatctata aggctatgtc tgagtttgat atctttatca attatatcga agcttatatg   1680
actattaagg cccggtag                                                  1698

SEQ ID NO: 33           moltype = AA   length = 565
FEATURE                 Location/Qualifiers
REGION                  1..565
                        note = DEboegfrDV07 Variant 4 Amino Acid Sequence
source                  1..565
                        mol_type = protein
                        organism = synthetic construct
SEQUENCE: 33
TDQCDNFPQM LRDLRDAFSR VKTFFQTKDE LDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLQQWG AGLLKPSETL   180
SLTCTVSGFS LTNYGVHWVR QPPGKGLEWL GVIWSGGNTD YNTPFTSRVA ISKDNSKNQV   240
SLRLNSVTAA DTAIYYCARA LTYYDYEFAY WGKGTTVTVS SGGGGSGGGG SGGGGSEIVL   300
TQSPGTLSLS PGERATLSCR ASQSIGTNIH WYQQKPGQAP RLLIKYASES ISGIPDRFSG   360
SGSGTDFTLT ITRLEPEDFA DYYCQQNNNW PTTFGQGTKL EIKGGGGSGG GGSGGGGSTD   420
QCDNFPQMLR DLRDAFSRVK TFFQTKDELD NLLLKESLLE DFKGYLGCQA LSEMIQFYLE   480
EVMPQAENQD PEIKDHVNSL GENLKTLRLR LRRCHRFLPC ENKSKAVEQI KNAFNKLQEK   540
GIYKAMSEFD IFINYIEAYM TIKAR                                         565

SEQ ID NO: 34           moltype = DNA   length = 1695
FEATURE                 Location/Qualifiers
misc_feature            1..1695
                        note = DEboegfrDV07 Variant 4 Nucleic Acid Sequence
source                  1..1695
                        mol_type = other DNA
                        organism = synthetic construct
SEQUENCE: 34
accgaccagt gcgacaactt ccctcagatg ctgcgggacc tgagagatgc cttctccaga    60
gtgaaaacat tcttccagac caaggacgag ctggacaacc tgctgctgaa agagtccctg   120
ctggaagatt tcaagggcta cctgggctgt caggcccctgt ccgagatgat ccagttctac   180
ctggaagaag tgatgcccca ggccgagaat caggaccccg agatcaagga ccacgtgaac   240
tccctgggcg agaaccctaa aaccctgcgg ctgagactgc ggcggtgcca cagatttctg   300
ccctgcgaga acaagtccaa ggccgtgaa cagatcaaga acgccttcaa caagctgcaa   360
gagaagggca tctacaaggc catgagcgag ttcgacatct tcatcaacta catcgaggcc   420
tacatgacca tcaaggccag aggcggcgga ggatctggcg gaggtggaag cggaggcggt   480
ggatctcagg ttcagttgca gcaatggggc gctggcctgc tgaagccttc tgagacactg   540
tctctgacct gcaccgtgtc cggcttctcc ctgaccaatt atggcgtgca ctgggtccga   600
cagcctccag gcaaaggatt ggaatggctg ggagtgattt ggagcggcgg caacaccgac   660
tacaacaccc ctttcacctc tagagtggcc atctccaagg acaactccaa gaaccaggtg   720
tccctgagac tgaactccgt gaccgctgcc gataccgcca tctactactg tgctagagcc   780
ctgacctact acgactacga gttcgcctat tggggcaagg caccaccgt gactgttagt   840
agtggtggtg gcggtagtgg cggaggcggc tcaggcggtg gtggatctga aattgtgctg   900
acccagtctc ctggcactct gtctttgagc cctggcgaga gagctaccct gtcctgtaga   960
gcctctcagt ccatcggcac caacatccac tggtatcagc agaagcctgg acaggcccct  1020
cggctgctga ttaagtacgc ctccgagtcc atcagcggca tccctgacag attctccggc  1080
tctggctctg gcaccgactt caccctgaca atcacccggc tggaacctga ggacttcgcc  1140
gactactact gccagcagaa caacaactgg cccaccacct ttggccaggg caccaagctg  1200
gaaatcaaag gtggcggtgg ttcaggtggc ggaggaagcg gcggaggcgg atctacagat  1260
cagtgtgaca atttccccca aatgctgagg gatctgcggg acgccttcag ccgggtcaag  1320
acatttttttc agacaaagga tgaactcgat aacctcttgc tcaaagagag cctgctcgag  1380
gacttcaaag gatatctggg atgccaggct ctgagcgaaa tgattcagtt ttatctcgag  1440
gaagtcatgc ctcaagcaga gaaccaggat ccagagatta aggatcatgt gaatagcctc  1500
ggggagaacc tcaagacact gagactccgg ctgagaagat gccaccggtt tctgccttgt  1560
gaaaacaaaa gcaaggctgt cgagcagatt aagaatgctt taacaaatt gcaagaaaaa  1620
gggatctata aggctatgtc tgagtttgat atctttatca attatatcga agcttatatg  1680
actattaagg cccgg                                                    1695

SEQ ID NO: 35           moltype = AA   length = 713
```

| | | |
|---|---|---|
| FEATURE | Location/Qualifiers | |
| REGION | 1..713 | |
| | note = DK210egfr Amino Acid Sequence | |
| source | 1..713 | |
| | mol_type = protein | |
| | organism = synthetic construct | |

SEQUENCE: 35
```
TDQCDNFPQM LRDLRDAFSR VKTFFQTKDE LDNLLLKESL LEDFKGYLGC QALSEMIQFY    60
LEEVMPQAEN QDPEIKDHVN SLGENLKTLR LRLRRCHRFL PCENKSKAVE QIKNAFNKLQ   120
EKGIYKAMSE FDIFINYIEA YMTIKARGGG GSGGGGSGGG GSQVQLQQWG AGLLKPSETL   180
SLTCAVYGFS LTNYGVHWIR QPPGKGLEWL GVIWSGGNTD YNTPFTSRVA ISKDNSKNQV   240
SLRLNSVTAA DTAIYYCARA LTYYDYEFAY WGKGTTVTVS SGGGGSGGGG SGGGGSAPTS   300
SSTKKTQLQL EHLLLDLQMI LNGINNYKNP KLTRMLTFKF YMPKKATELK HLQCLEEELK   360
PLEEVLNLAQ SKNFHLRPRD LISNINVIVL ELKGSETTFM CEYADETATI VEFLNRWITF   420
CQSIISTLTG GGGSGGGGSG GGGSEIVLTQ SPGTLSLSPG ERATLSCRAS QSIGTNIHWY   480
QQKPGQAPRL LIKYASESIS GFPDRFSGSG SGTDFTLTIT RLEPEDFAMY YCQQNNNWPT   540
TFGQGTKLEI KGGGGSGGGG SGGGGSTDQC DNFPQMLRDL RDAFSRVKTF FQTKDELDNL   600
LLKESLLEDF KGYLGCQALS EMIQFYLEEV MPQAENQDPE IKDHVNSLGE NLKTLRLRLR   660
RCHRFLPCEN KSKAVEQIKN AFNKLQEKGI YKAMSEFDIF INYIEAYMTI KAR          713
```

| | | |
|---|---|---|
| SEQ ID NO: 36 | moltype = AA length = 133 | |
| FEATURE | Location/Qualifiers | |
| REGION | 1..133 | |
| | note = Human IL-2 Amino Acid Sequence | |
| source | 1..133 | |
| | mol_type = protein | |
| | organism = Homo sapiens | |

SEQUENCE: 36
```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133
```

| | | |
|---|---|---|
| SEQ ID NO: 37 | moltype = AA length = 119 | |
| FEATURE | Location/Qualifiers | |
| REGION | 1..119 | |
| | note = Modified VH region of anti-EGFR antibody | |
| source | 1..119 | |
| | mol_type = protein | |
| | organism = synthetic construct | |

SEQUENCE: 37
```
QVQLQQWGAG LLKPSETLSL TCAVYGFSLT NYGVHWIRQP PGKGLEWLGV IWSGGNTDYN    60
TPFTSRVAIS KDNSKNQVSL RLNSVTAADT AIYYCARALT YYDYEFAYWG KGTTVTVSS   119
```

| | | |
|---|---|---|
| SEQ ID NO: 38 | moltype = AA length = 107 | |
| FEATURE | Location/Qualifiers | |
| REGION | 1..107 | |
| | note = Modified VL region of anti-EGFR antibody | |
| source | 1..107 | |
| | mol_type = protein | |
| | organism = synthetic construct | |

SEQUENCE: 38
```
EIVLTQSPGT LSLSPGERAT LSCRASQSIG TNIHWYQQKP GQAPRLLIKY ASESISGFPD    60
RFSGSGSGTD FTLTITRLEP EDFAMYYCQQ NNNWPTTFGQ GTKLEIK                107
```

| | | |
|---|---|---|
| SEQ ID NO: 39 | moltype = AA length = 7 | |
| FEATURE | Location/Qualifiers | |
| REGION | 1..7 | |
| | note = Artificial Sequence Linker 1 | |
| source | 1..7 | |
| | mol_type = protein | |
| | organism = synthetic construct | |

SEQUENCE: 39
```
SSGGGGS                                                              7
```

| | | |
|---|---|---|
| SEQ ID NO: 40 | moltype = AA length = 15 | |
| FEATURE | Location/Qualifiers | |
| REGION | 1..15 | |
| | note = Artificial Sequence Linker 2 | |
| source | 1..15 | |
| | mol_type = protein | |
| | organism = synthetic construct | |

SEQUENCE: 40
```
GGGGSGGGGS GGGGS                                                    15
```

| | | |
|---|---|---|
| SEQ ID NO: 41 | moltype = AA length = 17 | |
| FEATURE | Location/Qualifiers | |
| REGION | 1..17 | |
| | note = Artificial Sequence Linker 3 | |
| source | 1..17 | |

```
                        mol_type = protein
                        organism = synthetic construct
SEQUENCE: 41
SSGGGGSGGG GSGGGGS                                                       17

SEQ ID NO: 42           moltype = AA  length = 6
FEATURE                 Location/Qualifiers
REGION                  1..6
                        note = Artificial Sequence 6xHis tag
source                  1..6
                        mol_type = protein
                        organism = synthetic construct
SEQUENCE: 42
HHHHHH                                                                    6

SEQ ID NO: 43           moltype = AA  length = 129
FEATURE                 Location/Qualifiers
REGION                  1..129
                        note = Human IL-4 Amino Acid Sequence
source                  1..129
                        mol_type = protein
                        organism = Homo sapiens
SEQUENCE: 43
HKCDITLQEI IKTLNSLTEQ KTLCTELTVT DIFAASKNTT EKETFCRAAT VLRQFYSHHE        60
KDTRCLGATA QQFHRHKQLI RFLKRLDRNL WGLAGLNSCP VKEANQSTLE NFLERLKTIM       120
REKYSKCSS                                                               129

SEQ ID NO: 44           moltype = AA  length = 129
FEATURE                 Location/Qualifiers
REGION                  1..129
                        note = hIL4 (N38A)
source                  1..129
                        mol_type = protein
                        organism = synthetic construct
SEQUENCE: 44
HKCDITLQEI IKTLNSLTEQ KTLCTELTVT DIFAASKATT EKETFCRAAT VLRQFYSHHE        60
KDTRCLGATA QQFHRHKQLI RFLKRLDRNL WGLAGLNSCP VKEANQSTLE NFLERLKTIM       120
REKYSKCSS                                                               129

SEQ ID NO: 45           moltype = AA  length = 129
FEATURE                 Location/Qualifiers
REGION                  1..129
                        note = hIL4 (T13D)
source                  1..129
                        mol_type = protein
                        organism = synthetic construct
SEQUENCE: 45
HKCDITLQEI IKDLNSLTEQ KTLCTELTVT DIFAASKATT EKETFCRAAT VLRQFYSHHE        60
KDTRCLGATA QQFHRHKQLI RFLKRLDRNL WGLAGLNSCP VKEANQSTLE NFLERLKTIM       120
REKYSKCSS                                                               129

SEQ ID NO: 46           moltype = AA  length = 713
FEATURE                 Location/Qualifiers
REGION                  1..713
                        note = DK410DV06 (non targeting)
source                  1..713
                        mol_type = protein
                        organism = synthetic construct
SEQUENCE: 46
TDQCDNFPQM LRDLRDAFSR VKTFFQTKDE VDNLLLKESL LEDFKGYLGC QALSEMIQFY        60
LEEVMPQAEN QDPEIKDHVN SLGENLKTLR LRLRRCHRFL PCENKSKAVE QIKNAFNKLQ       120
EKGIYKAMSE FDIFINYIEA YMTIKARGGG GSGGGGSGGG GSQVQLQQWG AGLLKPSETL       180
SLTCAVYGGS FTTTYWNWIR QPPGKGLEWI GEVNYSGNAN YNPSLKGRVA ISVDTSKNQF       240
SLRLNSVTAA DTAIYYCTSR IRSHIAYSWK GDVWGKGTTV TVSSGGGGSG GGGSGGGGSH       300
KCDITLQEII KTLNSLTEQK TLCTELTVTD IFAASKNTTE KETFCRAATV LRQFYSHHEK       360
DTRCLGATAQ QFHRHKQLIR FLKRLDRNLW GLAGLNSCPV KEANQSTLEN FLERLKTIMR       420
EKYSKCSSGG GGSGGGGSGG GGSEIVMTQS PGTLSLSPGE RATLSCRASQ SVPRNYIGWF       480
QQKPGQAPRL LIYGASSRAA GFPDRFSGSG SGTDFTLTIT RLEPEDFAMY YCHQYDRLPY       540
TFGQGTKLEI KGGGGSGGGG SGGGGSTDQC DNFPQMLRDL RDAFSRVKTF FQTKDEVDNL       600
LLKESLLEDF KGYLGCQALS EMIQFYLEEV MPQAENQDPE IKDHVNSLGE NLKTLRLRLR       660
RCHRFLPCEN KSKAVEQIKN AFNKLQEKGI YKAMSEFDIF INYIEAYMTI KAR              713

SEQ ID NO: 47           moltype = AA  length = 729
FEATURE                 Location/Qualifiers
REGION                  1..729
                        note = DK410HADeglyDV06mCD14
source                  1..729
                        mol_type = protein
                        organism = synthetic construct
```

```
SEQUENCE: 47
MGWSLILLFL VAVATRVHST DQCDNFPQML RDLRDAFSRV KTFFQTKDEV DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCAVSGFSL TTYYMNWIRQ PPGKGLEWIG FIRSGGSTEY   240
NPSLKGRVAI SVDTSKNQFS LRLNSVTAAD TAIYYCARGD YYNFDYWGKG TTVTVSSGGG   300
GSGGGGSGGG GSHKCDITLQ EIIKDLNSLT EQKTLCTELT VTDIFAASKA TTEKETFCRA   360
ATVLRQFYSH HEKDTRCLGA TAQQFHRHKQ LIRFLKRLDR NLWGLAGLNS CPVKEANQST   420
LENFLERLKT IMREKYSKCS SGGGGSGGGG SGGGGSEIVM TQSPGTLSLS PGERATLSCR   480
ASQSLVHSNG KTYVGWFQQK PGQAPRLLIY RVSNRAAGFP DRFSGSGSGT DFTLTITRLE   540
PEDFAMYYCL QSTHFPRTFG QGTKLEIKGG GGSGGGGSGG GGSTDQCDNF PQMLRDLRDA   600
FSRVKTFFQT KDEVNLLLKE SLLEDFKGYL GCQALSEMIQ FYLEEVMPQA ENQDPEIKDH   660
VNSLGENLKT LRLRLRRCHR FLPCENKSKA VEQIKNAFNK LQEKGIYKAM SEFDIFINYI   720
EAYMTIKAR                                                          729

SEQ ID NO: 48         moltype = AA  length = 729
FEATURE               Location/Qualifiers
REGION                1..729
                      note = DK410HADeglyDV07mCD14
source                1..729
                      mol_type = protein
                      organism = synthetic construct
SEQUENCE: 48
MGWSLILLFL VAVATRVHST DQCDNFPQML RDLRDAFSRV KTFFQTKDEL DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCAVSGFSL TTYYMNWIRQ PPGKGLEWIG FIRSGGSTEY   240
NPSLKGRVAI SVDTSKNQFS LRLNSVTAAD TAIYYCARGD YYNFDYWGKG TTVTVSSGGG   300
GSGGGGSGGG GSHKCDITLQ EIIKDLNSLT EQKTLCTELT VTDIFAASKA TTEKETFCRA   360
ATVLRQFYSH HEKDTRCLGA TAQQFHRHKQ LIRFLKRLDR NLWGLAGLNS CPVKEANQST   420
LENFLERLKT IMREKYSKCS SGGGGSGGGG SGGGGSEIVM TQSPGTLSLS PGERATLSCR   480
ASQSLVHSNG KTYVGWFQQK PGQAPRLLIY RVSNRAAGFP DRFSGSGSGT DFTLTITRLE   540
PEDFAMYYCL QSTHFPRTFG QGTKLEIKGG GGSGGGGSGG GGSTDQCDNF PQMLRDLRDA   600
FSRVKTFFQT KDELNLLLKE SLLEDFKGYL GCQALSEMIQ FYLEEVMPQA ENQDPEIKDH   660
VNSLGENLKT LRLRLRRCHR FLPCENKSKA VEQIKNAFNK LQEKGIYKAM SEFDIFINYI   720
EAYMTIKAR                                                          729

SEQ ID NO: 49         moltype = AA  length = 729
FEATURE               Location/Qualifiers
REGION                1..729
                      note = DK410ngDV06CmD14
source                1..729
                      mol_type = protein
                      organism = synthetic construct
SEQUENCE: 49
MGWSLILLFL VAVATRVHST DQCDNFPQML RDLRDAFSRV KTFFQTKDEV DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCAVSGFSL TTYYMNWIRQ PPGKGLEWIG FIRSGGSTEY   240
NPSLKGRVAI SVDTSKNQFS LRLNSVTAAD TAIYYCARGD YYNFDYWGKG TTVTVSSGGG   300
GSGGGGSGGG GSHKCDITLQ EIIKTLNSLT EQKTLCTELT VTDIFAASKA TTEKETFCRA   360
ATVLRQFYSH HEKDTRCLGA TAQQFHRHKQ LIRFLKRLDR NLWGLAGLNS CPVKEANQST   420
LENFLERLKT IMREKYSKCS SGGGGSGGGG SGGGGSEIVM TQSPGTLSLS PGERATLSCR   480
ASQSLVHSNG KTYVGWFQQK PGQAPRLLIY RVSNRAAGFP DRFSGSGSGT DFTLTITRLE   540
PEDFAMYYCL QSTHFPRTFG QGTKLEIKGG GGSGGGGSGG GGSTDQCDNF PQMLRDLRDA   600
FSRVKTFFQT KDEVNLLLKE SLLEDFKGYL GCQALSEMIQ FYLEEVMPQA ENQDPEIKDH   660
VNSLGENLKT LRLRLRRCHR FLPCENKSKA VEQIKNAFNK LQEKGIYKAM SEFDIFINYI   720
EAYMTIKAR                                                          729

SEQ ID NO: 50         moltype = AA  length = 729
FEATURE               Location/Qualifiers
REGION                1..729
                      note = DK410ngDV07CmD14
source                1..729
                      mol_type = protein
                      organism = synthetic construct
SEQUENCE: 50
MGWSLILLFL VAVATRVHST DQCDNFPQML RDLRDAFSRV KTFFQTKDEL DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCAVSGFSL TTYYMNWIRQ PPGKGLEWIG FIRSGGSTEY   240
NPSLKGRVAI SVDTSKNQFS LRLNSVTAAD TAIYYCARGD YYNFDYWGKG TTVTVSSGGG   300
GSGGGGSGGG GSHKCDITLQ EIIKTLNSLT EQKTLCTELT VTDIFAASKA TTEKETFCRA   360
ATVLRQFYSH HEKDTRCLGA TAQQFHRHKQ LIRFLKRLDR NLWGLAGLNS CPVKEANQST   420
LENFLERLKT IMREKYSKCS SGGGGSGGGG SGGGGSEIVM TQSPGTLSLS PGERATLSCR   480
ASQSLVHSNG KTYVGWFQQK PGQAPRLLIY RVSNRAAGFP DRFSGSGSGT DFTLTITRLE   540
PEDFAMYYCL QSTHFPRTFG QGTKLEIKGG GGSGGGGSGG GGSTDQCDNF PQMLRDLRDA   600
FSRVKTFFQT KDELNLLLKE SLLEDFKGYL GCQALSEMIQ FYLEEVMPQA ENQDPEIKDH   660
VNSLGENLKT LRLRLRRCHR FLPCENKSKA VEQIKNAFNK LQEKGIYKAM SEFDIFINYI   720
```

```
EAYMTIKAR                                                            729

SEQ ID NO: 51           moltype = AA  length = 729
FEATURE                 Location/Qualifiers
REGION                  1..729
                        note = DK410ngDV06mMAdCAM
source                  1..729
                        mol_type = protein
                        organism = synthetic construct
SEQUENCE: 51
MGWSLILLFL VAVATRVHST DQCDNFPQML RDLRDAFSRV KTFFQTKDEV DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCAVYGFTF TDFYMNWIRQ PPGKGLEWIG LIRNKANAYT   240
TEYNPSVKGR VAISVDTSKN QFSLRLNSVT AADTAIYYCT SDDHWGKGTT VTVSSGGGGS   300
GGGGSGGGGS HKCDITLQEI IKTLNSLTEQ KTLCTELTVT DIFAASKATT EKETFCRAAT   360
VLRQFYSHHE KDTRCLGATA QQFHRHKQLI RFLKRLDRNL WGLAGLNSCP VKEANQSTLE   420
NFLERLKTIM REKYSKCSSG GGGSGGGGSG GGGSEIVMTQ SPGTLSLSPG ERATLSCKSS   480
QSLLYNENKK NYLAWFQQKP GQAPRLLIYW ASTRESGFPD RFSGSGSTD  FTLTITRLEP   540
EDFAMYYCQQ YYNFPYTFGQ GTKLEIKGGG SGGGGGSGGG GSTDQCDNFP QMLRDLRDAF   600
SRVKTFFQTK DEVDNLLLKE SLLEDFKGYL GCQALSEMIQ FYLEEVMPQA ENQDPEIKDH   660
VNSLGENLKT LRLRLRRCHR FLPCENKSKA VEQIKNAFNK LQEKGIYKAM SEFDIFINYI   720
EAYMTIKAR                                                           729

SEQ ID NO: 52           moltype = AA  length = 733
FEATURE                 Location/Qualifiers
REGION                  1..733
                        note = DK210her2 (Variant 2)
source                  1..733
                        mol_type = protein
                        organism = synthetic construct
SEQUENCE: 52
MGWSLILLFL VAVATRVHST DQCDNFPQML RDLRDAFSRV KTFFQTKDEL DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCAVYGFNI KDTYIHWIRQ PPGKGLEWIG RIYPTNGYTR   240
YADSVKGRVA ISVDTSKNQF SLRLNSVTAA DTAIYYCTSW GGDGFYAMDY WGKGTTVTVS   300
SGGGGSGGGG SGGGGSAPTS SSTKKTQLQL EHLLLDLQMI LNGINNYKNP KLTRMLTFKF   360
YMPKKATELK HLQCLEEELK PLEEVLNLAQ SKNFHLRPRD LISNINVIVL ELKGSETTFM   420
CEYADETATI VEFLNRWITF CQSIISTLTG GGGSGGGGSG GGGSEIVMTQ SPGTLSLSPG   480
ERATLSCRAS QDVNTAVAWF QQKPGQAPRL LIYSASFLYS GFPDRFSGSG SGTDFTLTIT   540
RLEPEDFAMY YCQQHYTTPP TFGQGTKLEI KGGGSGGGG  SGGGGSTDQC DNFPQMLRDL   600
RDAFSRVKTF FQTKDELDNL LLKESLLEDF KGYLGCQALS EMIQFYLEEV MPQAENQDPE   660
IKDHVNSLGE NLKTLRLRLR RCHRFLPCEN KSKAVEQIKN AFNKLQEKGI YKAMSEFDIF   720
INYIEAYMTI KAR                                                      733

SEQ ID NO: 53           moltype = AA  length = 733
FEATURE                 Location/Qualifiers
REGION                  1..733
                        note = DK210her2 (Variant 3)
source                  1..733
                        mol_type = protein
                        organism = synthetic construct
SEQUENCE: 53
MGWSLILLFL VAVATRVHST DQCDNFPQML RDLRDAFSRV KTFFQTKDEL DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCAVYGFNI KDTYIHWIRQ PPGKGLEWVA RIYPTNGYTR   240
YADSVKGRFA ISADTSKNQA SLRLNSVTAA DTAIYYCSRW GGDGFYAMDY WGKGTTVTVS   300
SGGGGSGGGG SGGGGSAPTS SSTKKTQLQL EHLLLDLQMI LNGINNYKNP KLTRMLTFKF   360
YMPKKATELK HLQCLEEELK PLEEVLNLAQ SKNFHLRPRD LISNINVIVL ELKGSETTFM   420
CEYADETATI VEFLNRWITF CQSIISTLTG GGGSGGGGSG GGGSEIVMTQ SPGTLSLSPG   480
ERATLSCRAS QDVNTAVAWY QQKPGQAPRL LIYSASFLYS GFPDRFSGSR SGTDFTLTIT   540
RLEPEDFAMY YCQQHYTTPP TFGQGTKLEI KGGGSGGGG  SGGGGSTDQC DNFPQMLRDL   600
RDAFSRVKTF FQTKDELDNL LLKESLLEDF KGYLGCQALS EMIQFYLEEV MPQAENQDPE   660
IKDHVNSLGE NLKTLRLRLR RCHRFLPCEN KSKAVEQIKN AFNKLQEKGI YKAMSEFDIF   720
INYIEAYMTI KAR                                                      733

SEQ ID NO: 54           moltype = AA  length = 733
FEATURE                 Location/Qualifiers
REGION                  1..733
                        note = DK210her2 (Variant 4)
source                  1..733
                        mol_type = protein
                        organism = synthetic construct
SEQUENCE: 54
MGWSLILLFL VAVATRVHST DQCDNFPQML RDLRDAFSRV KTFFQTKDEL DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
```

```
SQVQLQEWGA GLLKPSETLS LTCAASGFNI KDTYIHWVRQ PPGKGLEWVA RIYPTNGYTR    240
YADSVKGRFA ISADTSKNQA SLRLNSVTAA DTAVYYCSRW GGDGFYAMDY WGKGTTVTVS    300
SGGGGSGGGG SGGGGSAPTS SSTKKTQLQL EHLLLDLQMI LNGINNYKNP KLTRMLTFKF    360
YMPKKATELK HLQCLEEELK PLEEVLNLAQ SKNFHLRPRD LISNINVIVL ELKGSETTFM    420
CEYADETATI VEFLNRWITF CQSIISTLTG GGGSGGGGSG GGGSEIVMTQ SPGTLSLSPG    480
ERATLSCRAS QDVNTAVAWY QQKPGQAPRL LIYSASFLYS GVPDRFSGSR SGTDFTLTIT    540
RLEPEDFATY YCQQHYTTPP TFGQGTKLEI KGGGGSGGGG SGGGGSTDQC DNFPQMLRDL    600
RDAFSRVKTF FQTKDELDNL LLKESLLEDF KGYLGCQALS EMIQFYLEEV MPQAENQDPE    660
IKDHVNSLGE NLKTLRLRLR RCHRFLPCEN KSKAVEQIKN AFNKLQEKGI YKAMSEFDIF    720
INYIEAYMTI KAR                                                      733

SEQ ID NO: 55           moltype = AA  length = 733
FEATURE                 Location/Qualifiers
REGION                  1..733
                        note = DK210her2 (Variant 5)
source                  1..733
                        mol_type = protein
                        organism = synthetic construct
SEQUENCE: 55
MGWSLILLFL VAVATRVHST DQCDNFPQML RDLRDAFSRV KTFFQTKDEL DNLLLKESLL     60
EDFKGYLGCQ ALSEMIQFYL EEVMPQAENQ DPEIKDHVNS LGENLKTLRL RLRRCHRFLP    120
CENKSKAVEQ IKNAFNKLQE KGIYKAMSEF DIFINYIEAY MTIKARGGGG SGGGGSGGGG    180
SQVQLQEWGA GLLKPSETLS LTCAASGFNI KDTYIHWVRQ PPGKGLEWVA RIYPTNGYTR    240
YADSVKGRFA ISADTSKNQA SLQMNSLRAE DTAVYYCSRW GGDGFYAMDY WGKGTTVTVS    300
SGGGGSGGGG SGGGGSAPTS SSTKKTQLQL EHLLLDLQMI LNGINNYKNP KLTRMLTFKF    360
YMPKKATELK HLQCLEEELK PLEEVLNLAQ SKNFHLRPRD LISNINVIVL ELKGSETTFM    420
CEYADETATI VEFLNRWITF CQSIISTLTG GGGSGGGGSG GGGSEIQMTQ SPSSLSLSPG    480
ERATLSCRAS QDVNTAVAWY QQKPGQAPRL LIYSASFLYS GVPDRFSGSR SGTDFTLTIS    540
SLQPEDFATY YCQQHYTTPP TFGQGTKLEI KGGGGSGGGG SGGGGSTDQC DNFPQMLRDL    600
RDAFSRVKTF FQTKDELDNL LLKESLLEDF KGYLGCQALS EMIQFYLEEV MPQAENQDPE    660
IKDHVNSLGE NLKTLRLRLR RCHRFLPCEN KSKAVEQIKN AFNKLQEKGI YKAMSEFDIF    720
INYIEAYMTI KAR                                                      733

SEQ ID NO: 56           moltype = AA  length = 728
FEATURE                 Location/Qualifiers
REGION                  1..728
                        note = DK410ngDV06CD14 (Variant 2)
source                  1..728
                        mol_type = protein
                        organism = synthetic construct
SEQUENCE: 56
MGWSLILLFL VAVATRVHST DQCDNFPQML RDLRDAFSRV KTFFQTKDEV DNLLLKESLL     60
EDFKGYLGCQ ALSEMIQFYL EEVMPQAENQ DPEIKDHVNS LGENLKTLRL RLRRCHRFLP    120
CENKSKAVEQ IKNAFNKLQE KGIYKAMSEF DIFINYIEAY MTIKARGGGG SGGGGSGGGG    180
SQVQLQQWGA GLLKPSETLS LTCAVYGYSI TSDSAWNWIR QPPGKGLEWI GYISYSGSTS    240
YNPSLKSRVA ISVDTSKNQF SLRLNSVTAA DTAIYYCTSG LRFAYWGKGT TVTVSSGGGG    300
SGGGGSGGGG SHKCDITLQE IIKTLNSLTE QKTLCTELTV TDIFAASKAT TEKETFCRAA    360
TVLRQFYSHH EKDTRCLGAT AQQFHRHKQL IRFLKRLDRN LWGLAGLNSC PVKEANQSTL    420
ENFLERLKTI MREKYSKCSS GGGGSGGGGS GGGGSEIVMT QSPGTLSLSP GERATLSCRA    480
SESVDSYVNS FLHWFQQKPG QAPRLLIYRA SNLQSGFPDR FSGSGSGTDF TLTITRLEPE    540
DFAMYYCQQS NEDPTTFGQG TKLEIKGGGG SGGGGSGGGG STDQCDNFPQ MLRDLRDAFS    600
RVKTFFQTKD EVDNLLLKES LLEDFKGYLG CQALSEMIQF YLEEVMPQAE NQDPEIKDHV    660
NSLGENLKTL RLRLRRCHRF LPCENKSKAV EQIKNAFNKL QEKGIYKAMS EFDIFINYIE    720
AYMTIKAR                                                            728

SEQ ID NO: 57           moltype = AA  length = 728
FEATURE                 Location/Qualifiers
REGION                  1..728
                        note = DK410ngDV06CD14 (Variant 3)
source                  1..728
                        mol_type = protein
                        organism = synthetic construct
SEQUENCE: 57
MGWSLILLFL VAVATRVHST DQCDNFPQML RDLRDAFSRV KTFFQTKDEV DNLLLKESLL     60
EDFKGYLGCQ ALSEMIQFYL EEVMPQAENQ DPEIKDHVNS LGENLKTLRL RLRRCHRFLP    120
CENKSKAVEQ IKNAFNKLQE KGIYKAMSEF DIFINYIEAY MTIKARGGGG SGGGGSGGGG    180
SQVQLQQWGA GLLKPSETLS LTCAVYGYSI TSDSAWNWIR QPPGKGLEWM GYISYSGSTS    240
YNPSLKSRIA ISRDTSKNQF SLRLNSVTAA DTAIYYCVRG LRFAYWGKGT TVTVSSGGGG    300
SGGGGSGGGG SHKCDITLQE IIKTLNSLTE QKTLCTELTV TDIFAASKAT TEKETFCRAA    360
TVLRQFYSHH EKDTRCLGAT AQQFHRHKQL IRFLKRLDRN LWGLAGLNSC PVKEANQSTL    420
ENFLERLKTI MREKYSKCSS GGGGSGGGGS GGGGSEIVLT QSPGTLSLSP GERATLSCRA    480
SESVDSYVNS FLHWYQQKPG QAPRLLIYRA SNLQSGFPDR FSGSGSRTDF TLTITRLEPE    540
DFAMYYCQQS NEDPTTFGQG TKLEIKGGGG SGGGGSGGGG STDQCDNFPQ MLRDLRDAFS    600
RVKTFFQTKD EVDNLLLKES LLEDFKGYLG CQALSEMIQF YLEEVMPQAE NQDPEIKDHV    660
NSLGENLKTL RLRLRRCHRF LPCENKSKAV EQIKNAFNKL QEKGIYKAMS EFDIFINYIE    720
AYMTIKAR                                                            728

SEQ ID NO: 58           moltype = AA  length = 728
FEATURE                 Location/Qualifiers
```

```
REGION                         1..728
                               note = DK410ngDV06CD14 (Variant 4)
source                         1..728
                               mol_type = protein
                               organism = synthetic construct
SEQUENCE: 58
MGWSLILLFL VAVATRVHST DQCDNFPQML RDLRDAFSRV KTFFQTKDEV DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCTVTGYSI TSDSAWNWIR QPPGKGLEWM GYISYSGSTS   240
YNPSLKSRIA ISRDTSKNQF SLRLNSVTAA DTATYYCVRG LRFAYWGKGT TVTVSSGGGG   300
SGGGGSGGGG SHKCDITLQE IIKTLNSLTE QKTLCTELTV TDIFAASKAT TEKETFCRAA   360
TVLRQFYSHH EKDTRCLGAT AQQFHRHKQL IRFLKRLDRN LWGLAGLNSC PVKEANQSTL   420
ENFLERLKTI MREKYSKCSS GGGGSGGGGS GGGGSEIVLT QSPGTLSLSP GERATLSCRA   480
SESVDSYVNS FLHWYQQKPG QAPRLLIYRA SNLQSGIPDR FSGSGSRTDF TLTITRLEPE   540
DFATYYCQQS NEDPTTFGQG TKLEIKGGGG SGGGGSGGGG STDQCDNFPQ MLRDLRDAFS   600
RVKTFFQTKD EVDNLLLKES LLEDFKGYLG CQALSEMIQF YLEEVMPQAE NQDPEIKDHV   660
NSLGENLKTL RLRLRRCHRF LPCENKSKAV EQIKNAFNKL QEKGIYKAMS EFDIFINYIE   720
AYMTIKAR                                                            728

SEQ ID NO: 59                  moltype = AA  length = 728
FEATURE                        Location/Qualifiers
REGION                         1..728
                               note = DK410ngDV06CD14 (Variant 5)
source                         1..728
                               mol_type = protein
                               organism = synthetic construct
SEQUENCE: 59
MGWSLILLFL VAVATRVHST DQCDNFPQML RDLRDAFSRV KTFFQTKDEV DNLLLKESLL    60
EDFKGYLGCQ ALSEMIQFYL EEVMPQAENQ DPEIKDHVNS LGENLKTLRL RLRRCHRFLP   120
CENKSKAVEQ IKNAFNKLQE KGIYKAMSEF DIFINYIEAY MTIKARGGGG SGGGGSGGGG   180
SQVQLQQWGA GLLKPSETLS LTCTVTGYSI TSDSAWNWIR QPPGKGLEWM GYISYSGSTS   240
YNPSLKSRIA ISRDTSKNQF SLQLNSVTTE DTATYYCVRG LRFAYWGKGT TVTVSSGGGG   300
SGGGGSGGGG SHKCDITLQE IIKTLNSLTE QKTLCTELTV TDIFAASKAT TEKETFCRAA   360
TVLRQFYSHH EKDTRCLGAT AQQFHRHKQL IRFLKRLDRN LWGLAGLNSC PVKEANQSTL   420
ENFLERLKTI MREKYSKCSS GGGGSGGGGS GGGGSEIVLT QSPGTLSLSP GERATLSCRA   480
SESVDSYVNS FLHWYQQKPG QAPRLLIYRA SNLQSGIPDR FSGSGSRTDF TLTINRVEPE   540
DFATYYCQQS NEDPTTFGQG TKLEIKGGGG SGGGGSGGGG STDQCDNFPQ MLRDLRDAFS   600
RVKTFFQTKD EVDNLLLKES LLEDFKGYLG CQALSEMIQF YLEEVMPQAE NQDPEIKDHV   660
NSLGENLKTL RLRLRRCHRF LPCENKSKAV EQIKNAFNKL QEKGIYKAMS EFDIFINYIE   720
AYMTIKAR                                                            728

SEQ ID NO: 60                  moltype = DNA  length = 2208
FEATURE                        Location/Qualifiers
misc_feature                   1..2208
                               note = DK210egfr Nucleic Acid Sequence
source                         1..2208
                               mol_type = other DNA
                               organism = synthetic construct
SEQUENCE: 60
gccgccacca tgggatggtc tttgatcctg ctgttcctgg tggccgtggc taccagagtg     60
cattctaccg accagtgcga caacttccct cagatgctgc gggacctgag ggacgccttc    120
tccagagtga aacattctt ccagaccaag acgagctgg acaacctgct gctgaaagag    180
tccctgctgg aagatttcaa gggctacctg gctgtcagg cctgtccga gatgatccag    240
ttctacctgg aagaagtgat gccccaggcc gagaatcagg accctgagat caaggaccat    300
gtgaactccc tgggcgagaa cctgaaaacc ctgcggctga ctgcggcg tgtcacaga    360
tttctgccct gcgagaacaa gtccaaggcc gtgaacaga tcaagaacgc cttcaacaag    420
ctgcaagaga gggcatcta caaggccatg agcgagttcg acatcttcat caactacatc    480
gaggcctaca tgaccatcaa ggctagaggt ggcggaggat ctggcggtgg tggttctggc    540
ggaggcggat ctcaggttca gttgcaacaa tggggcgctg cctgctgga gccttctgga    600
acactgtctc tgacctgcgc cgtgtacggc ttctctctga ccaattacgg cgtgcactgg    660
atccggcagc cacctggaaa aggactgaa tggctgggag tgatttggag cggcggcaac    720
accgactaca acaccccttt tacctctaga gtggccatct ccaaggacaa ctccaagaac    780
caggtgtccc tgaactgaa ctctgtgacc gccgctgata ccgccatcta ctactgtgct    840
agagccctga cctactacga ctacgagttc gcttattggg gcaagggcac caccgtgaca    900
gtttcatctg gcggcggagg aagcggtggc ggcgtagcg gaggtggtgg atctgctcct    960
acctcctcca gcaccaagaa acccagctg agttggagc atctgctgct ggacctccag   1020
atgatcctga acggcatcaa caactacaag atcccaagc tgccggat gctgaccttc   1080
aagttctaca tgcccaagaa ggcaccgag tgaaacatc tgcagtgcct ggaagaggaa   1140
ctgaagcccc tcgaggaagt gctgaatctg gcccagtcca gaacttcca cctgaggcct   1200
agggacctga tctccaacat caacgtgatc gtgctcgagc tgaagggctc cgagacaacc   1260
tttatgtgcg agtacgccga cgagacagcc accatcgtgg aatttctgaa ccggtggatc   1320
accttctgcc agtccatcat ctctacattg accggtggtg gcggatcagg cggtggcgga   1380
agcggaggcg gtggctctga aattgtgctg accagtccc tgcacactct gtctttgagt   1440
cctggcgaga gagctaccct gtcctgcaga gcttctcagt ccatcggcac aacatccac   1500
tggtatcagc agaagcctgg acaggcccct cggctgctga ttaagtacgc ctctgagtcc   1560
atcagcggct ccctgacag attctctggc tctggatctg caccgactt caccctgacc   1620
atcaccgac tggaacccga ggacttcgct atgtactact gccagcagaa caacaactgg   1680
cccaccacct ttggccaggg caccaagttg gaaatcaaag gtggcggtgg aagtggcggc   1740
```

```
ggtggctcag gcggcggtgg atctacagac cagtgtgata attttccaca gatgctcagg   1800
gatctccgcg acgcctttag ccgggtcaag acatttttc agacaaagga tgaactcgat    1860
aatctcctgc tcaaagagag cctgctcgag gactttaaag gatacctggg atgccaggct   1920
ctcagcgaaa tgattcagtt ttatttggag gaagtcatgc tcaagctga aaaccaggat    1980
ccagagatta aggatcacgt caacagcctc ggcgagaagt caagacact gcgcctgagg    2040
ctgagaagat gccaccggtt tctgccttgt gaaaacaaga gcaaggctgt cgagcagatt   2100
aagaatgctt ttaacaaatt gcaagaaaaa gggatctata aggctatgtc tgagtttgat   2160
atctttatca attatatcga agcttatatg actattaagg cccggtga               2208

SEQ ID NO: 61             moltype = DNA  length = 2288
FEATURE                   Location/Qualifiers
misc_feature              1..2288
                          note = DK410ngDV06CD14 Variant 2 Nucleic Acid Sequence
source                    1..2288
                          mol_type = other DNA
                          organism = synthetic construct
SEQUENCE: 61
atcgaaatta atacgactca ctatagggag acccaagctg gctagcgccg ccaccatggg   60
atggtctttg atcctgctgt tcctggtggc cgtggctacc agagtgcatt ctaccgacca   120
gtgcgacaac ttccctcaga tgctgcggga cctgagagat gccttctcca gagtgaaaac   180
attcttccag accaaggacg aggtggacaa cctgctgctg aaagagtccc tgctggaaga   240
tttcaagggc tacctgggct gtcaggccct gtccgagatg atccagttct acctggaaga   300
agtgatgccc caggccgaga tcaggaccc cgagatcaag gaccacgtga actccctggg   360
cgagaacctg aaaaccctgc ggctgagact gcggcggtgc acagatttc tgccctgcga   420
gaacaagtcc aaggccgtgg aacagatcaa gaacgccttc aacaagctgc agagaagggg   480
catctacaag gccatgagcg agttcgacat cttcatcaag cctacatgac                540
catcaaggcc agaggcggcg aggatctgg cggaggtgga agcggaggcg gtggatctca   600
ggttcagttg cagcaatggg gcgctggcct gctgaagcct tctgagacac tgtctctgac   660
ctgcgccgtg tacggctact ccatcacctc tgactctgcc tggaattgga tccggcagcc   720
tcctggcaaa ggactggaat ggatcggcta catctcctac tccggctcca ccagctacaa   780
cccccagcctg aagtctagag tggccatctc cgtggacacc tccaagaacc agttctccct   840
gagactgaac tccgtgaccg ccgctgatac cgccatctac tactgcacct ccggcctgag   900
atttgcctac tggggcaagg gcaccaccgt gactgttagt agtggtggtg gcggtagtgg   960
cggaggcggc tcaggcggtg gcggatctca taagtgcgac atcaccctgc aagaaatcat   1020
caagaccctg aacagcctga ccgagcagaa aactctgtgc accgagctga ccgtgaccga   1080
tatctttgcc gcctcaagg ccacaaccga gaaagagaca ttctgcagag ccgccaccgt    1140
gctgcggcag ttttactctc accacgaaa ggacaccaga tgcctgggcg ctaccgctca   1200
gcagttccac agacacaagc agctgatccg gttcctgaag cggctggaca gaaacctgtg   1260
gggactcgcc ggcctgaact cttgccctgt gaaaagatgc aaccagtcta acctggaaaa   1320
cttcctggaa cggctcaaga ccatcatgcg cgagaagtac tccaagtgct ccagcggtgg   1380
cggtggttca ggtggcggtg gctctggcgg cggaggtagt gaaattgtga tgacccagtc   1440
tcctggcact ctgtctctgt ctcccggcga gagagctacc ctgtcttgta gagcctccga   1500
gtccgtggac tcctacgtga acagcttcct gcactggttc cagcagaagc ctggacaggc   1560
tcccagactg ctgatctaca gagcctccaa cctgcagagc ggcttccctg acagattttc   1620
cggctctggc tccggcaccg acttcaccct gacaatcacc agactggaac ccgaggactt   1680
cgctatgtac tactgccagc agtccaacga ggacccccac acatttggcc agggcaccaa   1740
gctggaaatc aaaggtggcg gaggaagtgg tcggagggc tccggcggag ggggttctac   1800
agatcagtgt gataattttc cacagatgct ccgcgatctg cgggacgcct ttagccgggt   1860
caagacattt tttcagacaa aggatgaagt cgataaccte ttgctcaaag agaggcctgct   1920
cgaggacttt aagggatatc tgggatgcca ggctctgagc gaaatgattc agttttatct   1980
cgaggaagtc atgcctcaag cagagaacca ggatcagtc attaaggctc atgtgaatag   2040
cctcggggag aacctcaaga cactgagact ccggctgaga agatgccacc ggtttctgcc   2100
ttgtgaaaac aaaagcaagg ctgtcgagca gattaagaat gcttttaaca aactccaaga   2160
aaaagggatc tataaggcta tgtctgagtt tgatatcttt atcaattata tcgaagctta   2220
tatgactatt aaggctcgct aggggcccgt taaacccgc tgatcagcct cgactgtgcc   2280
ttctagtt                                                            2288

SEQ ID NO: 62             moltype = DNA  length = 2303
FEATURE                   Location/Qualifiers
misc_feature              1..2303
                          note = DK210her2 Variant 4 Nucleic Acid Sequence
source                    1..2303
                          mol_type = other DNA
                          organism = synthetic construct
SEQUENCE: 62
atcgaaatta atacgactca ctatagggag acccaagctg gctagcgccg ccaccatggg   60
atggtctttg atcctgctgt tcctggtggc cgtggctacc agagtgcatt ctaccgacca   120
gtgcgacaac ttccctcaga tgctgcggga cctgagagat gccttctcca gagtgaaaac   180
attcttccag accaaggacg agctggacaa cctgctgctg aaagagtccc tgctggaaga   240
tttcaagggc tacctgggct gtcaggccct gtccgagatg atccagttct acctggaaga   300
agtgatgccc caggccgaga tcaggaccc cgagatcaag gaccacgtga actccctggg   360
cgagaacctg aaaaccctgc ggctgagact gcggcggtgc acagatttc tgccctgcga   420
gaacaagtcc aaggccgtgg aacagatcaa gaacgccttc aacaagctgc agagaagggg   480
catctacaag gccatgagcg agttcgacat cttcatcaag cctacatgac                540
catcaaggcc agaggcggcg aggatctgg cggaggtgga agcggaggcg gtggatctca   600
ggttcagttg caagaatggg gcgctggcct gctgaagcct tcgaaacac tgtctctgac   660
ctgcgccgcc agcggcttca acatcaagga cacctacatc cactgggtcc acagcctcc   720
aggcaaagga ctggaatggg tcgccagaat ctaccccacc aacggctaca ccagatacgc   780
cgactctgtg aaggggcagat tcgccatctc tgccgacacc tccaagaacc aggccagcct   840
```

```
gagactgaac tctgtgaccg ctgctgacac cgccgtgtac tactgctcta gatggggcgg    900
agatggcttc tacgccatgg actattgggg caagggcacc accgtgacag ttagtagtgg    960
tggtggcggt agtggcggag gcggctcagg cggtggtgga tctgctccta catcctccag   1020
caccaagaaa acccagctgc agttggagca tctgctgctg gacctccaga tgatcctgaa   1080
cggcatcaac aactacaaga accccaagct gacccggatg ctgaccttca agttctacat   1140
gcccaagaag gccaccgagc tgaaacatct gcagtgcctg gaagaggaac tgaagcccct   1200
cgaggaagtg ctgaatctgg cccagtccaa gaacttccac ctgaggccta gggacctgat   1260
ctccaacatc aacgtgatcg tgctcgagct gaagggctcc gagacaacct tcatgtgcga   1320
gtacgccgac gagacagcta ccatcgtgga atttctgaac cggtggatca ccttctgcca   1380
gtccatcatc tctaccctga ctggtggcgg aggaagcggc ggaggcggat ctggcggcgg   1440
aggctctgaa attgtgatga cccagtctcc tggcactctg tctctgtctc ccggcgagag   1500
agctaccctg tcttgtagag ccagccagga cgtgaacacc gctgtggctt ggtatcagca   1560
gaagcctgga caggcccctc ggctgctgat ctactctgcc tcctttctgt actccggcgt   1620
gcccgacaga ttctccggct ctagatctgg caccgacttc accctgacca tcaccagact   1680
ggaacccgag gacttcgcca cctactactg ccagcagcac tacaccacac acctaccctt   1740
tggccagggc accaagctgg aaatcaaagg tggtggcgga tcaggcggtg gcggtagcgg   1800
tggcggaggt tctacagacc agtgtgataa ttttcccaa atgctgaggg atctgcggga   1860
cgccttctct agggtcaaga cattttttca gacaaaggat gaactcgata acctcttgct   1920
caaagagagc ctgctcgagg actttaaggg atatctggga tgccaggctc tgagcgaaat   1980
gattcagttt tatttggagg aagtcatgcc tcaagcagaa aaccaggatc agagattaa    2040
ggatcatgtc aacagcctcg gcgagaatct caagacactg cgcctgaggc tgagaagatg   2100
ccaccggttt ctgccttgtg aaaacaaaag caaggctgtc gagcagatta agaatgcttt   2160
taacaaactc caagaaaaag ggatcctataa ggctatgtct gagtttgata tctttatcaa   2220
ttatatcgaa gcttatatga ctattaaggc tcgctagggg cccgtttaaa cccgctgatc   2280
agcctcgact gtgccttcta gtt                                            2303

SEQ ID NO: 63        moltype = DNA  length = 2303
FEATURE              Location/Qualifiers
misc_feature         1..2303
                     note = DK210her2 Variant 5 Nucleic Acid Sequence
source               1..2303
                     mol_type = other DNA
                     organism = synthetic construct
SEQUENCE: 63
atcgaaatta atacgactca ctataggag acccaagctg gctagcgccg ccaccatggg    60
atggtctttg atcctgctgt tcctggtggc cgtggctacc agagtgcatt ctaccgacca   120
gtgcgacaac ttccctcaga tgctgcggga cctgagagat gccttctcca gagtgaaaac   180
attcttccag accaaggacg agctggacaa cctgctgctg aaagagtccc tgctggaaga   240
tttcaagggc tacctgggct gtcaggccct gtccgagatg atccagttct acctggaaga   300
agtgatgccc caggccgaga tcaggaccc gagatcaag gaccacgtga actccctggg   360
cgagaacctg aaaaccctgc ggctgagact gcggcggtgc cacagattc tgccctgcga   420
gaacaagtcc aaggccgtgg aacagatcaa gaacgccttc aacaagctgc agagaaggg   480
catctacaag gccatgagcg agttcgacat cttcatcaac tatatcgagg cctacatgac   540
catcaaggcc agaggcggcg gaggatctgg cggaggtgga agcggaggcg gtggatctca   600
ggtgcagttg caagaatggg gcgctggcct gctgaagcct tccgaaacac tgtctctgac   660
ctgcgccgcc agcggcttca acatcaagga cacctacatc cactgggtcc gacaggctcc   720
aggcaaagga ctggaatggg tcgccagaat ctaccccacc aacggctaca ccagatacgc   780
cgactctgtc aagggcagat cgccatctc tgccgacacc tccaagaacc aggccagcct   840
gcagatgaac agcctgagag tgaggacac cgccgtgtac tactgctcta gatggggcgg   900
agatggcttc tacgccatgg actattgggg caagggcacc accgtgacag ttagtagtgg   960
tggtggcggt agtggcggag gcggctcagg cggtggtgga tctgctccta catcctccag  1020
caccaagaaa acccagctgc agttggagca tctgctgctg gacctccaga tgatcctgaa  1080
cggcatcaac aactacaaga accccaagct gacccggatg ctgaccttca agttctacat  1140
gcccaagaag gccaccgagc tgaaacatct gcagtgcctg gaagaggaac tgaagcccct  1200
cgaggaagtg ctgaatctgg cccagtccaa gaacttccac ctgaggccta gggacctgat  1260
ctccaacatc aacgtgatcg tgctcgagct gaagggctcc gagacaacct tcatgtgcga  1320
gtacgccgac gagacagcta ccatcgtgga atttctgaac cggtggatca ccttctgcca  1380
gtccatcatc tctaccctga ctggtggcgg aggaagcggc ggaggcggat ctggcggcgg  1440
aggctctgaa attcagatga cccagtctcc ttccagctcc tctctgtccc ctggcgagag  1500
agctaccctg tcttgtagag ccagccagga cgtgaacacc gctgtggctt ggtatcagca  1560
gaagcctgga caggcccctc ggctgctgat ctactctgcc tcctttctgt actccggcgt  1620
gcccgacaga ttctccggct ctagatctgg caccgacttt accctgacaa tcagctccct  1680
gcagcctgag gacttcgcca cctactactg ccagcagcac tacaccacac acctaccctt  1740
tggccagggc accaagctgg aaatcaaagg tggtggcgga tcaggcggtg gcggtagcgg  1800
tggcggaggt tctacagacc agtgtgataa ttttcccaa atgctgaggg atctgcggga  1860
cgccttctct agggtcaaga cattttttca gacaaaggat gaactcgata acctcttgct  1920
caaagagagc ctgctcgagg actttaaagg atatctggga tgccaggctc tgagcgaaat  1980
gattcagttt tatttggagg aagtcatgcc tcaagcagaa aaccaggatc agagattaa    2040
ggatcatgtc aacagcctcg gcgagaatct caagacactg agactgaggc tgcggagatg  2100
ccaccggttt ctgccttgtg aaaacaagag caaggctgtc gagcagatta agaatgcttt  2160
taacaaactc caagaaaaag ggatcctataa ggctatgtct gagtttgata tctttatcaa  2220
ttatatcgaa gcttatatga ctattaaggc tcgctagggg cccgtttaaa cccgctgatc  2280
agcctcgact gtgccttcta gtt                                            2303
```